United States Patent
Boisart et al.

(10) Patent No.: US 12,018,300 B2
(45) Date of Patent: Jun. 25, 2024

(54) GENETICALLY OPTIMISED MICROORGANISM FOR PRODUCING MOLECULES OF INTEREST

(71) Applicant: ENOBRAQ, Ramonville Saint-Agne (FR)

(72) Inventors: Cedric Boisart, Belberaud (FR); Nicolas Morin, Toulouse (FR)

(73) Assignee: EPPEN EUROPE, Paris (FR)

( * ) Notice: Subject to any disclaimer, the term of this patent is extended or adjusted under 35 U.S.C. 154(b) by 0 days.

(21) Appl. No.: 17/573,877

(22) Filed: Jan. 12, 2022

(65) Prior Publication Data

US 2022/0348897 A1    Nov. 3, 2022

Related U.S. Application Data

(63) Continuation of application No. 16/480,569, filed as application No. PCT/EP2018/052005 on Jan. 26, 2018, now abandoned.

(30) Foreign Application Priority Data

Jan. 27, 2017 (FR) ........................ 1750694

(51) Int. Cl.
   *C12N 9/88* (2006.01)
   *C12N 9/12* (2006.01)
   *C12P 7/42* (2006.01)
   *C12P 7/62* (2022.01)
   *C12P 7/625* (2022.01)
   *C12P 13/00* (2006.01)
   *C12P 13/14* (2006.01)

(52) U.S. Cl.
   CPC ............ *C12N 9/88* (2013.01); *C12N 9/1205* (2013.01); *C12P 7/42* (2013.01); *C12P 7/62* (2013.01); *C12P 7/625* (2013.01); *C12P 13/001* (2013.01); *C12P 13/14* (2013.01); *C12Y 207/01019* (2013.01); *C12Y 401/01039* (2013.01)

(58) Field of Classification Search
   CPC ........ C12N 9/88; C12N 9/1205; C12N 15/52; C12N 9/0006; C12N 9/0008; C12N 9/1217; C12N 9/18; C12P 7/42; C12P 7/62; C12P 7/625; C12P 13/001; C12P 13/14; C12Y 207/01019; C12Y 401/01039; C12Y 101/01044; C12Y 301/01031; C12Y 101/01049; C12Y 102/01012; C12Y 207/02003
   See application file for complete search history.

(56) References Cited

U.S. PATENT DOCUMENTS

2005/0079482 A1    4/2005  Maranas et al.

FOREIGN PATENT DOCUMENTS

| FR | 3016371 A1 | 7/2015 |
| WO | 2015107496 A1 | 7/2015 |
| WO | 2015177800 A2 | 11/2015 |

OTHER PUBLICATIONS

Chen et al., The Entner-Doudoroff pathway is an overlooked glycolytic route in cyanobacteria and plants, PNAS, 2016, 113(19) 5441-5446.
Li et al., The coupling of glycolysis and the Rubisco-based pathway through the non-oxidative pentose phosphate to achieve low carbon dioxide emission fermentation, Biousource Technology, 2015, 187: 189-197.
Li et al., Engineered yeast with a CO2-fixation pathway to improve the bio-ethanol production from xylose-mixed sugars, Scientific Reports, 2017, 7:43875: 1-9.
Whisstock et al., "Quarterly Reviews of Biophysics, 2003, Prediction of protein function from protein sequence and structure", 36(3):307-340.
Witkowski et al., "Conversion of a beta-ketoacyl synthase to a malonyl decarboxylase by replacement of the active-site cysteine with glutamine", Biochemistry, Sep. 7, 1999, 38(36): pp. 11643-11650.
Kisselev., Polypeptide release factors in prokaryotes and eurakaryotes: same function, different structure. Structure, 2002, vol. 10: 8-9.
Mueller-Cajar et al., Directing the evolution of Rubisco and Rubisco activase: first impressions of a new tool for photosynthesis research. Photosynth Res (2008) 98: 667-675.
Linck et al., On the role of GAPDH isoenzymes during pentose fermentation in engineered *Saccharomyces cerevisiae*. FEMS Yeast Res 14 (2014), 389-398.
Datsenko et al., One-step inactivation of chromosomal genes in *Escherichia coli* K-12 using PCR products, Proc Natl Acad Sci, 2000, 97(12):6640-6645.
Lodish et al., Section 12.5 Recombination between Homologous DNA Sites, Molecular Cell Biology 4th ed, 2000, New York:W. H. Freeman and Company, 1-9.
Thomas et al., Site-Directed Mutagenesis by Gene Targeting in Mouse Embryo-Derived Stem Cells, Cell, 1987, 51:503-512.

(Continued)

Primary Examiner — Iqbal H Chowdhury
(74) Attorney, Agent, or Firm — BCF LLP

(57) ABSTRACT

The invention concerns a genetically modified microorganism expressing a functional type I or II RuBisCO enzyme and a functional phosphoribulokinase (PRK), and in which the glycolysis pathway is at least partially inhibited, said microorganism being genetically modified so as to produce an exogenous molecule and/or to overproduce an endogenous molecule. According to the invention, the oxidative branch of the pentose phosphate pathway may also be at least partially inhibited. The invention also concerns the use of such a genetically modified microorganism for the production or overproduction of a molecule of interest and processes for the synthesis or bioconversion of molecules of interest.

11 Claims, 3 Drawing Sheets

Specification includes a Sequence Listing.

(56) References Cited

OTHER PUBLICATIONS

Kaufmann et al., Genomic Promoter Replacement Cassettes to Alter Gene Expression in the Yeast *Saccharomyces cerevisiae*, Chapter 16, Williams (ed.), Strain Engineering: Methods and Protocols, Methods Molecular Biology, 2011, 765:275-294.

Daneholt, RNA Interference, Advanced Information on the Nobel Prize in Physiology or Medecine, 2006, Karolinska Institutet, 1-10.

Kim et al., Hybrid restriction enzymes: Zinc finger fusions to Fok I, Proc. Natl. Acad. Sci. USA, 1996, 93:1156-1160.

Ousterout et al., The Development of TALE Nucleases for Biotechnology, Methods Mol Biol, 2016, 1338:27-42.

Mali et al., Cas9 as a versatile tool for engineering biology, Nat Methods, Oct. 2013, 10(10): 957-963.

Daboussi et al., Chromosomal context and epigenetic mechanisms control the efficacy of genome editing by rare-cutting designer endonucleases, Nucleic Acids Res, 2012, 40 (13):6367-79.

Tabita et al., Distinct form I, II, III, and IV Rubisco proteins from the three kingdoms of life provide clues about Rubisco evolution and structure/function relationships, Journal of Experimental Botany, 2008, 59(7):1515-1524.

Liu et al., Coupled chaperone action in folding and assembly of hexadecameric Rubisco, Nature, 2010, 463(14):197-202.

Verduyn et al., Effect of Benzoic Acid on Metabolic Fluxes in Yeasts: A Continuous-Culture Study on the Regulation of Respiration and Alcoholic Fermentation, Yeast, 1992, 8:501-517.

Visser et al., Rapid Sampling for Analysis of In Vivo Kinetics Using the BioScope: A System for Continuous-Pulse Experiments, Biotechnology and Bioengineering, 2002, 79(6):674-681.

Koller et al., Microbial PHA Production from Waste Raw Materials, Chen (ed.), Plastics from Bacteria: Natural Functions and Applications, Microbiology Monographs, 2010, 14:85-119.

Alfenore et al., Improving ethanol production and viability of *Saccharomyces cerevisiae* by a vitamin feeding strategy during fed-batch process, Appl Microbiol Biotechnol. 2002. 60:67-72.

Orth et al., What is flux balance analysis?, Nature Biotechnology, 2010, 28(3): 245-248.

Rocha et al., SOofptwtarFe lux: an open-source software platform for in silico metabolic engineering, BMC Systems Biology, 2010, 4(45): 1-12.

Mo et al., Connecting extracellular metabolomic measurements to intracellular flux states in yeast, BMC Systems Biology, 2009, 3:37:1-17.

Adams et al., Methods in Yeast Genetics, Cold Spring Harbor Laboratory Course Manual, 1997, 98-102.

Gietz et al., Transforming yeast with DNA, Methods in Molecular and Cellular Biology , 1995, 5:225-269.

Tippmann et al., Production of Farnesene and Santalene by *Saccharomyces cerevisiae* Using Fed-Batch Cultivations With RQ-Controlled Feed, Biotechnology and Bioengineering, 2016, 113(1):72-81.

Tippmann et al., Improved quantification of farnesene during microbial production from *Saccharomyces cerevisiae* in two-liquid-phase fermentations, Talanta, 2016, 146:100-106.

Usuda et al., Dynamic modeling of *Escherichia coli* metabolic and regulatory systems for amino-acid production, Journal of Biotechnoligy, 2010, 147:17-30.

Baba et al., Construction of *Escherichia coli* K-12 in-frame, single-gene knockout mutants: the Keio collection, Mol Syst Biol. 2006: 1-11.

Rodriguez et al., ATP citrate lyase mediated cytosolic acetyl-CoA biosynthesis increases mevalonate production in *Saccharomyces cerevisiae*, 2016, 15(48): 1-12.

Levin-Karp et al., Quantifying Translational Coupling in *E. coli* Synthetic Operons Using RBS Modulation and Fluorescent Reporters, ACS Synthetic Biology, 2013, 2:327-336.

Quandt et al., Versatile suicide vectors which allow direct selection for gene replacement in Gram-negative bacteria, Gene, 1993, 127(1):15-21.

Lindenkamp et al., Impact of Multiple β-Ketothiolase Deletion Mutations in Ralstonia eutropha H16 on the Composition of 3-Mercaptopropionic Acid-Containing Copolymers, Applied Environmental Microbiology, 2010, 76(16):5373-5382.

Lindenkamp et al., Genetically Modified Strains of Ralstonia eutropha H16 with β-Ketothiolase Gene Deletions for Production of Copolyesters with Defined 3-Hydroxyvaleric Acid Contents, Applied Environmental Microbiology, 2012, 78(15):5375-5383.

Srinivasan et al., A Novel High-Cell-Density Protein Expression System Based on Ralstonia eutropha, Applied and Environmental Microbiology, 2002, 68(12):5925-5932.

Hogrefe et al., Alcaligenes eutrophus Hydrogenase Genes (Hox), Journal of Bacteriology, Apr. 1984, 158(1):43-48.

Shimizu et al., New Insight into the Role of the Calvin Cycle: Reutilization of CO2 Emitted through Sugar Degradation. Scientific Reports, 2015, 6:27961: 1-2.

Brandl et al., Pseudomonas oleovorans as a Source of Poly(P-Hydroxyalkanoates) for Potential Applications as Biodegradable Polyesters, Appl Environ Microbiol. Aug. 1988, 54(8):1977-1982.

Muller et al., Engineering of Ralstonia eutropha H16 for Autotrophic and Heterotrophic Production of Methyl Ketones, Applied and Environmental Microbiology, 2013,79(14):4433-4439.

Zelbuch et al., Spanning high-dimensional expression space using ribosome-binding site combinatorics, Nucleic Acids Research, 2013, 41(9): 1-8.

Yang et al., Metabolic engineering of *Escherichia coli* and in silico comparing of carboxylation pathways for high succinate productivity under aerobic conditions, Microbiological Research, 2014, 169 :432-40.

Sarkari et al., An efficient tool for metabolic pathway construction and gene integration for Aspergillus niger, Bioresource Technology, 2017, 245:1327-1333.

Bekker et al., An enzyme cocktail for efficient protoplast formation in Aspergillus niger, J Microbiol Methods. 2009, 76:305-306.

Kusters-Van Someren et al., Structure of the Aspergillus niger pelA gene and its expression in Aspergillus niger and Aspergillus nidulans, Current Genetics, 1991, 20:293-299.

Blumhoff et al., Six novel constitutive promoters for metabolic engineering of Aspergillus niger, Applied Genetics and Molecular Biotechnology, 2013, 97:259-267.

Blumhoff et al., Targeting enzymes to the right compartment: Metabolic engineering for itaconic acid production by Aspergillus niger, Metabolic Engineering, 2013, 19:26-32.

Steiger et al.,Characterizing MttA as a mitochondrial cis-aconitic acid transporter by metabolic engineering, Metabolic Engineering, 2016, 35: 95-104.

Hevekerl et al., Filamentous fungi in microtiter plates-an easy way to optimize itaconic acid production with Aspergillus terreus, Appl Microbiol Biotechnol, 2014, 98:6983-6989.

Rubin et al., The essential gene set of a photosynthetic organism, CrossMark, PNAS, Oct. 27, 2015, E6634-E6643.

Karakaya et al., Mutagenesis of the tal gene-encoding Transaldolase in the Cyanobacteriwn,Anabaenasp. PCC7120, Turk J Biol, 2008, 32:135-141.

Oliver et al., A carbon sink pathway increases carbon productivity in cyanobacteria, Metabolic Engineering, 2015, 29: 106-112.

Osanai et al., Positive Regulation of Sugar Catabolic Pathways in the *Cyanobacterium synechocystis* sp. PCC 6803 by the Group 2 o Factor SigE, the Journal of Biological Chemistry, 2005, 280(35): 30653-30659.

Xia et al., Recycling Carbon Dioxide during Xylose Fermentation by Engineered *Saccharomyces cerevisiae*, ACS Synthetic Biology, 2017, 6:276-283.

Guadalupe-Medina et al., Carbon dioxide fixation by Calvin-Cycle enzymes improves ethanol yield in yeast, Biotechnology for Biofuels, 2013, 6(125): 1-12.

Xiong et al., Phosphoketolase pathway contributes to carbon metabolism in cyanobacteria, Nature Plants, 2016, 2: 1-8.

GENETICALLY OPTIMISED MICROORGANISM FOR PRODUCING MOLECULES OF INTEREST

CROSS-REFERENCE TO RELATED APPLICATIONS

The present Application is a continuation of U.S. application Ser. No. 17/573,877, filed on Jul. 14, 2022, which is a United States National Stage Patent Application under 35 U.S.C. 371 of International Application No. PCT/EP2018/052005, filed on Jan. 26, 2018, which claims benefit of priority from French Patent Application No. 1750694, files Jan. 27, 2017, the contents of each of which are herein incorporated by reference in their entirety.

Genetically optimised microorganism for producing molecules of interest

FIELD OF THE INVENTION

The invention concerns a genetically modified microorganism, capable of using carbon dioxide as an at least partial carbon source, for the production of molecules of interest. More specifically, the invention relates to a microorganism in which at least the glycolysis pathway is at least partially inhibited. The invention also relates to processes for the production of at least one molecule of interest using such a microorganism.

STATE OF THE ART

Over the past few years, a number of microbiological processes have been developed to enable the production of molecules of interest in large quantities.

For example, fermentation processes are used to produce molecules by a microorganism from a fermentable carbon source, such as glucose.

Bioconversion processes have also been developed to allow a microorganism to convert a co-substrate, not assimilable by said microorganism, into a molecule of interest. Here again, a carbon source is required, not for the actual production of the molecule of interest, but for the production of cofactors, and more particularly NADPH, that may be necessary for bioconversion. In general, the production yield of such microbiological processes is low, mainly due to the need for cofactors and the difficulty of balancing redox metabolic reactions. There is also the problem of the cost price of such molecules, since a source of carbon assimilable by the microorganism is still necessary. In other words, currently, in order to produce a molecule of interest with a microbiological process, it is necessary to provide a molecule (glucose, or other), certainly of lower industrial value, but which is sufficient to make the production of certain molecules not economically attractive.

At the same time, carbon dioxide ($CO_2$), whose emissions into the atmosphere are constantly increasing, is used little, if at all, in current microbiological processes, while its consumption by microorganisms for the production of molecules of interest would not only reduce production costs, but also address certain ecological issues.

There is therefore still a need for microbiological processes to enable the production of molecules of interest in large quantities and with lower cost prices than with current processes.

SUMMARY OF THE INVENTION

The advantage of using non-photosynthetic microorganisms genetically modified to capture $CO_2$ and use it as the main carbon source, in the same way as plants and photosynthetic microorganisms, has already been demonstrated. For example, microorganisms modified to express a functional RuBisCO (ribulose-1,5-bisphosphate carboxylase/oxygenase—EC 4.1.1.39) and a functional PRK (phosphoribulokinase—EC 2.7.1.19) to reproduce a partial Calvin cycle and convert ribulose-5-phosphate into two 3-phosphoglycerate molecules by capturing a carbon dioxide molecule have been developed.

By working on the solutions provided by the Calvin cycle to produce molecules of interest using $CO_2$ as carbon source, the inventors discovered that it is possible to increase the production yield of molecules of interest by coupling part of the Calvin cycle (PRK/RuBisCO) to at least partial inhibition of glycolysis. The inventors have also discovered that it is possible to increase the consumption of exogenous $CO_2$ during the production of molecules of interest, by also at least partially inhibiting the oxidative branch of the pentose phosphate pathway. The microorganisms thus developed make it possible to produce on a large scale and with an industrially attractive yield a large number of molecules of interest, such as amino acids, organic acids, terpenes, terpenoids, peptides, fatty acids, polyols, etc.

The invention thus relates to a genetically modified microorganism expressing a functional RuBisCO enzyme and a functional phosphoribulokinase (PRK), and in which the glycolysis pathway is at least partially inhibited, said microorganism being genetically modified so as to produce an exogenous molecule of interest and/or to overproduce an endogenous molecule of interest, other than a RuBisCO or phosphoribulokinase enzyme.

In one particular embodiment, the genetically modified microorganism has an oxidative branch of the pentose phosphate pathway that is also at least partially inhibited.

The invention also concerns the use of a genetically modified microorganism according to the invention, for the production or overproduction of a molecule of interest, preferentially selected from amino acids, peptides, proteins, vitamins, sterols, flavonoids, terpenes, terpenoids, fatty acids, polyols and organic acids.

The present invention also concerns a biotechnological process for producing or overproducing at least one molecule of interest, characterized in that it comprises a step of culturing a genetically modified microorganism according to the invention, under conditions allowing the synthesis or bioconversion, by said microorganism, of said molecule of interest, and optionally a step of recovering and/or purifying said molecule of interest.

It also concerns a process for producing a molecule of interest comprising (i) inserting at least one sequence encoding an enzyme involved in the synthesis or bioconversion of said molecule of interest into a recombinant microorganism according to the invention, (ii) culturing said microorganism under conditions allowing the expression of said enzyme and optionally (iii) recovering and/or purifying said molecule of interest.

DETAILED DESCRIPTION OF THE INVENTION

Definitions

Figure 1:
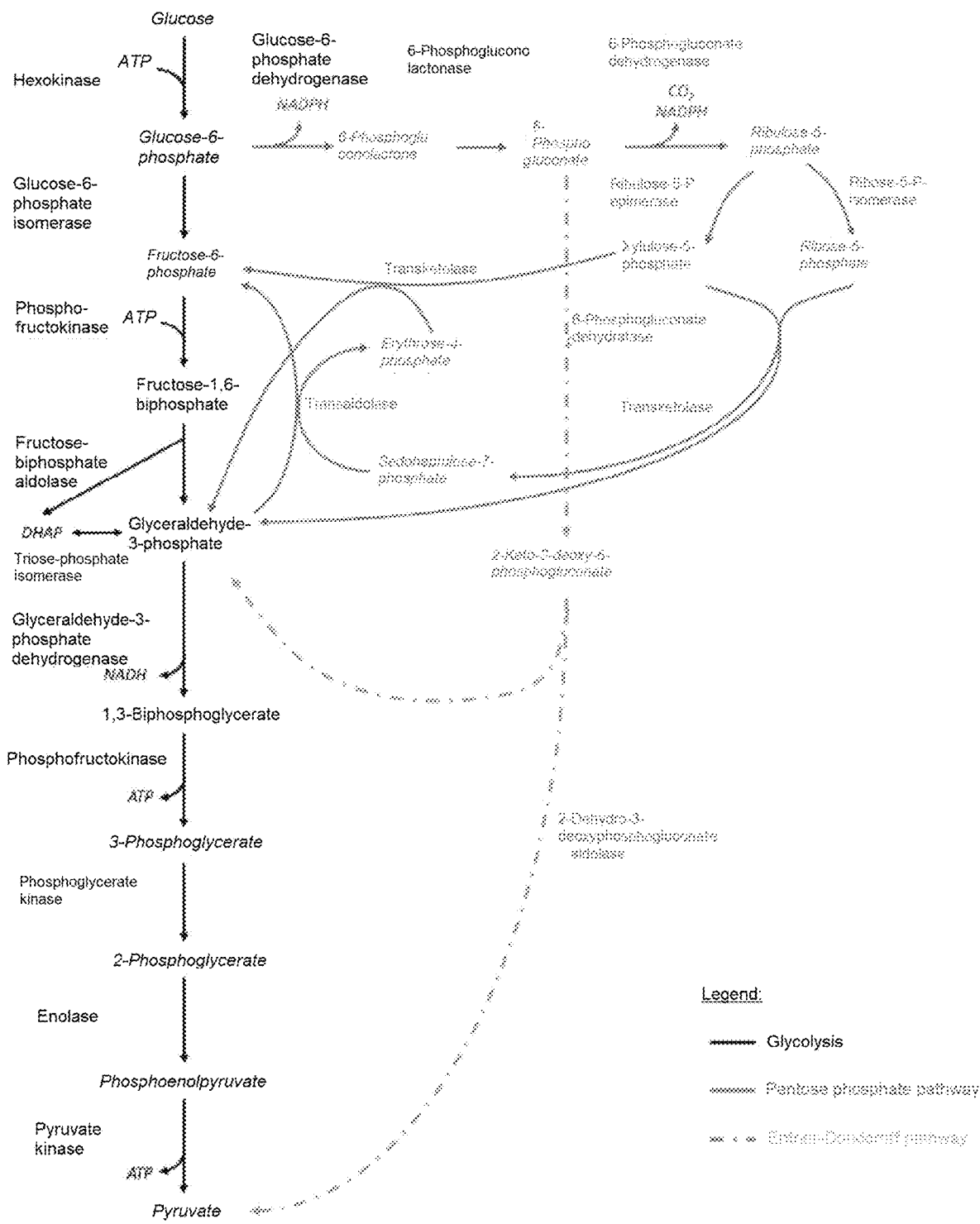
FIG. 1: General diagram of glycolysis, the pentose phosphate pathway and the Entner-Doudoroff pathway.

The terms "recombinant microorganism", "modified microorganism" and "recombinant host cell" are used herein interchangeably and refer to microorganisms that have been genetically modified to express or overexpress endogenous nucleotide sequences, to express heterologous nucleotide sequences, or that have an altered expression of an endogenous gene. "Alteration" means that the expression of the gene, or level of an RNA molecule or equivalent RNA molecules encoding one or more polypeptides or polypeptide subunits, or the activity of one or more polypeptides or polypeptide subunits is regulated, so that the expression, the level or the activity is higher or lower than that observed in the absence of modification.

It is understood that the terms "recombinant microorganism", "modified microorganism" and "recombinant host cell" refer not only to the particular recombinant microorganism but to the progeny or the potential progeny of such a microorganism. As some modifications may occur in subsequent generations, due to mutation or environmental influences, these offspring may not be identical to the mother cell, but they are still understood within the scope of the term as used here.

In the context of the invention, an at least partially "inhibited" or "inactivated" metabolic pathway refers to an altered metabolic pathway that can no longer function properly in the microorganism considered, compared with the same wild-type microorganism (not genetically modified to inhibit said metabolic pathway). In particular, the metabolic pathway may be interrupted, leading to the accumulation of an intermediate metabolite. Such an interruption may be achieved, for example, by inhibiting the enzyme necessary for the degradation of an intermediate metabolite of the metabolic pathway considered and/or by inhibiting the expression of the gene encoding that enzyme. The metabolic pathway may also be attenuated, i.e. slowed down. Such attenuation may be achieved, for example, by partially inhibiting one or more enzymes involved in the metabolic pathway considered and/or partially inhibiting the expression of a gene encoding at least one of these enzymes and/or by exploiting the cofactors required for certain reactions. The expression "at least partially inhibited metabolic pathway" means that the level of the metabolic pathway considered is reduced by at least 20%, more preferentially at least 30%, 40%, 50%, or more, compared with the level in a wild-type microorganism. The reduction may be greater, and in particular be at least greater than 60%, 70%, 80%, 90%. According to the invention, inhibition may be total, in the sense that the metabolic pathway considered is no longer used at all by said microorganism. According to the invention, such inhibition may be temporary or permanent.

According to the invention, "inhibition of gene expression" means that the gene is no longer expressed in the microorganism considered or that its expression is reduced, compared with wild-type microorganisms (not genetically modified to inhibit gene expression), leading to the absence of production of the corresponding protein or to a significant decrease in its production, and in particular to a decrease of more than 20%, more preferentially 30%, 40%, 50%, 60%, 70%, 80%, 90%. In one embodiment, inhibition can be total, i.e. the protein encoded by said gene is no longer produced at all. Inhibition of gene expression can be achieved by deletion, mutation, insertion and/or substitution of one or more nucleotides in the gene considered. Preferentially, inhibition of gene expression is achieved by total deletion of the corresponding nucleotide sequence. According to the invention, any method of gene inhibition, known per se by the skilled person and applicable to a microorganism, may be used. For example, inhibition of gene expression can be achieved by homologous recombination (Datsenko et al., Proc Natl Acad Sci USA. 2000; 97:6640-5; Lodish et al., Molecular Cell Biology $4^{th}$ ed. 2000. W. H. Freeman and Company. ISBN 0-7167-3136-3); random or directed mutagenesis to modify gene expression and/or encoded protein activity (Thomas et al., Cell. 1987; 51:503-12); modification of a promoter sequence of the gene to alter its expression (Kaufmann et al., Methods Mol Biol. 2011; 765:275-94. doi: 10.1007/978-1-61779-197-0_16); targeting induced local lesions in genomes (TILLING); conjugation, etc. Another particular approach is gene inactivation by insertion of a foreign sequence, for example by transposon mutagenesis using mobile genetic elements (transposons), of natural or artificial origin. According to another preferred embodiment, inhibition of gene expression is achieved by knock-out techniques. Inhibition of gene expression can also be achieved by extinguishing the gene using interfering, ribozyme or antisense RNA (Daneholt, 2006. Nobel Prize in Physiology or Medicine). In the context of the present invention, the term "interfering RNA" or "iRNA" refers to any iRNA molecule (for example single-stranded RNA or double-stranded RNA) that can block the expression of a target gene and/or facilitate the degradation of the corresponding mRNA. Gene inhibition can also be achieved by genome editing methods that allow direct genetic modification of a given genome, through the use of zinc finger nucleases (Kim et al., PNAS; 93: 1156-1160), transcription activator-like effector nucleases, or "TALEN" (Ousterout et al., Methods Mol Biol. 2016; 1338:27-42. doi: 10.1007/978-1-4939-2932-0_3), a system combining Cas9 nucleases with clustered regularly interspaced short palindromic repeats, or "CRISPR" (Mali et al., Nat Methods. 2013 October; 10(10): 957-63. doi: 10.1038/nmeth.2649), or meganucleases (Daboussi et al., Nucleic Acids Res. 2012. 40:6367-79). Inhibition of gene expression can also be achieved by inactivating the protein encoded by said gene.

In the context of the invention, "NADPH-dependent" or "NADPH-consuming" biosynthesis or bioconversion means all biosynthesis or bioconversion pathways in which one or more enzymes require the concomitant supply of electrons obtained by the oxidation of an NADPH cofactor. "NADPH-dependent" biosynthesis or bioconversion pathways notably concern the synthesis of amino acids (e.g. arginine, lysine, methionine, threonine, proline, glutamate, homoscrine, isoleucine, valine) γ-aminobutyric acid, terpenoids and terpenes (e.g. farnesene), vitamins and precursors (e.g. pantoate, pantothenate, transneurosporene, phylloquinone, tocopherols), sterols (e.g. squalene, cholesterol, testosterone, progesterone, cortisone), flavonoids (e.g. frambinone, vestinone), organic acids (e.g. citric acid, succinic acid, oxalic acid, itaconic acid, coumaric acid, 3-hydroxypropionic acid), polyols (e.g. sorbitol, xylitol, glycerol), polyamines (e.g. spermidine), aromatic molecules from stereospecific hydroxylation, via an NADP-dependent cytochrome p450 (e.g. phenylpropanoids, terpenes, lipids, tannins, fragrances, hormones).

The term "exogenous" as used here in reference to various molecules (nucleotide sequences, peptides, enzymes, etc.) refers to molecules that are not normally or naturally found in and/or produced by the microorganism considered. Conversely, the term "endogenous" or "native" refers to various molecules (nucleotide sequences, peptides, enzymes, etc.), designating molecules that are normally or naturally found in and/or produced by the microorganism considered.

Microorganisms

The invention proposes genetically modified microorganisms for the production of a molecule of interest, endogenous or exogenous.

"Genetically modified" microorganism means that the genome of the microorganism has been modified to incorporate a nucleic sequence encoding an enzyme involved in the biosynthesis or bioconversion pathway of a molecule of interest, or encoding a biologically active fragment thereof. Said nucleic sequence may have been introduced into the genome of said microorganism or one of its ancestors, by any suitable molecular cloning method. In the context of the invention, the genome of the microorganism refers to all genetic material contained in the microorganism, including extrachromosomal genetic material contained, for example, in plasmids, episomes, synthetic chromosomes, etc. The introduced nucleic sequence may be a heterologous sequence, i.e. one that does not naturally exist in said microorganism, or a homologous sequence. Advantageously, a transcriptional unit with the nucleic sequence of interest is introduced into the genome of the microorganism, under the control of one or more promoters. Such a transcriptional unit also includes, advantageously, the usual sequences such as transcriptional terminators, and, if necessary, other transcription regulatory elements.

Promoters usable in the present invention include constitutive promoters, i.e. promoters that are active in most cellular states and environmental conditions, as well as inducible promoters that are activated or suppressed by exogenous physical or chemical stimuli, and therefore induce a variable state of expression depending on the presence or absence of these stimuli. For example, when the microorganism is a yeast, it is possible to use a constitutive promoter, such as that of a gene among TEF1, TDH3, PGI1, PGK, ADH1. Examples of inducible promoters that can be used in yeast are tetO-2, GAL10, GAL10-CYC1, PHO5.

In general, the genetically modified microorganism according to the invention has the following features:
- Expression of a functional RuBisCO (EC 4.1.1.39);
- Expression of a functional PRK (EC 2.7.1.19);
- At least partial inhibition of glycolysis; and
- Expression of at least one gene involved in the synthesis and/or bioconversion of a molecule of interest, and/or inhibition of at least one gene encoding activity competing with the synthesis and/or bioconversion of a molecule of interest.

According to the invention, any microorganism can be used. Preferentially the microorganism is a eukaryotic cell, preferentially selected from yeasts, fungi, microalgae or a prokaryotic cell, preferentially a bacterium or cyanobacterium.

In one embodiment, the genetically modified microorganism according to the invention is a yeast, preferentially selected from among the ascomycetes (Spermophthoraceae and Saccharomycesceae), basidiomycetes (*Leucosporidium, Rhodosporidium, Sporidiobolus, Filobasidium*, and *Filobasidiella*) and deuteromycetes yeasts belonging to Fungi imperfecti (Sporobolomycetaceae, and Cryptococcaceae). Preferentially, the genetically modified yeast according to the invention belongs to the genus *Pichia, Kluyveromyces, Saccharomyces, Schizosaccharomyces, Candida, Lipomyces, Rhodotorula, Rhodosporidium, Yarrowia*, or *Debaryomyces*. More preferentially, the genetically modified yeast according to the invention is selected from *Pichia pastoris, Kluyveromyces lactis, Kluyveromyces marxianus, Saccharomyces cerevisiae, Saccharomyces carlsbergensis, Saccharomyces diastaticus, Saccharomyces douglasii, Saccharomyces kluyveri, Saccharomyces norbensis, Saccharomyces oviformis, Schizosaccharomyces pombe, Candida albicans, Candida tropicalis, Rhodotorula glutinis, Rhodosporidium toruloides, Yarrowia lipolytica, Debaryomyces hansenii* and *Lipomyces starkeyi*.

In another embodiment, the genetically modified microorganism according to the invention is a fungus, and more particularly a "filamentous" fungus. In the context of the invention, "filamentous fungi" refers to all filamentous forms of subdivision Eumycotina. For example, the genetically modified fungus according to the invention belongs to the genus *Aspergillus, Trichoderma, Neurospora, Podospora, Endothia, Mucor, Cochliobolus* or *Pyricularia*. Preferentially, the genetically modified fungus according to the invention is selected from *Aspergillus nidulans, Aspergillus niger, Aspergillus awomari, Aspergillus oryzae, Aspergillus terreus, Neurospora crassa, Trichoderma reesei*, and *Trichoderma viride*.

In another embodiment, the genetically modified microorganism according to the invention is a microalga. In the context of the invention, "microalga" refers to all eukaryotic microscopic algae, preferentially belonging to the classes or superclasses Chlorophyceae, Chrysophyceae, Prymnesiophyceae, Diatomac or Bacillariophyta, Euglenophyceae, Rhodophyceae, or Trebouxiophyceae. Preferentially, the genetically modified microalgae according to the invention are selected from *Nannochloropsis* sp. (e.g. *Nannochloropsis oculata, Nannochloropsis gaditana, Nannochloropsis salina*), *Tetraselmis* sp. (e.g. *Tetraselmis suecica, Tetraselmis chuii*), *Chlorella* sp. (e.g. *Chlorella salina, Chlorella protothecoides, Chlorella ellipsoidea, Chlorella emersonii, Chlorella minutissima, Chlorella pyrenoidosa, Chlorella sorokiniana, Chlorella vulgaris*), *Chlamydomonas* sp. (e.g. *Chlamydomonas reinhardtii*) *Dunaliella* sp. (e.g. *Dunaliella tertiolecta, Dunaliella salina*), Phaeodactulum *tricornutum, Botrycoccus braunii, Chroomonas salina, cyclotella cryptica, cyclotella* sp., Ettlia *texensis, Euglena gracilis, Gymnodinium nelsoni, Haematococcus pluvialis, Isochrysis galbana, Monoraphidium minutum*, Monoraphidium sp, *Neochloris oleoabundans, Nitzschia laevis, Onoraphidium sp., pavlova lutheri, Phaeodactylum tricornutum, Porphyridium cruentum, Scenedesmus* sp. (e.g. *Scenedesmus obliquuus, Scenedesmus* quadricaulaula, *Scenedesmus* sp.), Stichococcus *bacillaris, Spirulina platensis, Thalassiosira* sp.

In one embodiment, the genetically modified microorganism according to the invention is a bacterium, preferentially selected from phyla Acidobacteria, Actinobacteria, Aquificae, Bacterioidetes, *Chlamydia*, Chlorobi, Chloroflexi, Chrysiogenetes, Cyanobacteria, Deferribacteres, Deinococcus-*Thermus*, Dictyoglomi, Fibrobacteres, Firmicutes, Fusobacteria, Gemmatimonadetes, Nitrospirae, Planctomycetes, Proteobacteria, Spirochaetes, Thermodesulfobacteria, Thermomicrobia, Thermotogac, or Verrucomicrobia. Preferably, the genetically modified bacterium according to the invention belongs to the genus Acaryochloris, *Acetobacter, Actinobacillus, Agrobacterium, Alicyclobacillus, Anabaena, Anacystis, Anaerobiospirillum, Aquifex, Arthrobacter, Arthrospira*, Azobacter, *Bacillus, Brevibacterium, Burkholderia, Chlorobium, Chromatium, Chlorobaculum, Clostridium, Corynebacterium, Cupriavidus, Cyanothece, Enterobacter, Deinococcus, Erwinia, Escherichia, Geobacter*, Gloeobacter, *Gluconobacter, Hydrogenobacter, Klebsiella, Lactobacillus, Lactococcus, Mannheimia, Mesorhizobium, Methylobacterium, Microbacterium,*

*Microcystis, Nitrobacter, Nitrosomonas, Nitrospina, Nitrospira, Nostoc, Phormidium, Prochlorococcus, Pseudomonas, Ralstonia, Rhizobium, Rhodobacter, Rhodococcus, Rhodopseudomonas, Rhodospirillum, Salmonella, Scenedesmun, Serratia, Shigella, Staphylococcus, Streptomyces, Synechoccus, Synechocystis, Thermosynechococcus, Trichodesmium,* or *Zymomonas*. Also preferably, the genetically modified bacterium according to the invention is selected from the species *Agrobacterium tumefaciens, Anaerobiospirillum succiniciproducens, Actinobacillus succinogenes, Aquifex aeolicus, Aquifex pyrophilus, Bacillus subtilis, Bacillus amyloliquefacines, Brevibacterium ammoniagenes, Brevibacterium immariophilum, Clostridium pasteurianum, Clostridium ljungdahlii, Clostridium acetobutylicum, Clostridium beigerinckii, Corynebacterium glutamicum, Cupriavidus necator, Cupriavidus metallidurans, Enterobacter sakazakii, Escherichia coli, Gluconobacter oxydans, Hydrogenobacter thermophilus, Klebsiella oxytoca, Lactococcus lactis, Lactobacillus plantarum, Mannheimia succiniciproducens, Mesorhizobium loti, Pseudomonas aeruginosa, Pseudomonas mevalonii, Pseudomonas pudica, Pseudomonas putida, Pseudomonas fluorescens, Rhizobium etli, Rhodobacter capsulatus, Rhodobacter sphaeroides, Rhodospirillum rubrum, Salmonella enterica, Salmonella enterica, Salmonella typhi, Salmonella typhimurium, Shigella dysenteriae, Shigella flexneri, Shigella sonnei, Staphylococcus aureus, Streptomyces coelicolor, Zymomonas mobilis, Acaryochloris marina, Anabaena variabilis, Arthrospira platensis, Arthrospira maxa, Chlorobium tepidum, Chlorobaculum sp., Cyanothece sp., Gloeobacter violaceus, Microcystis aeruginosa, Nostoc punctiforme, Prochlorococcus marinus, Synechococcus elongatus, Synechocystis sp., Thermosynechococcus elongatus, Trichodesmium erythraeum,* and *Rhodopseudomonas palustris*.

Expression of a Functional RuBisCO and a Functional PRK

According to the invention, the microorganism can naturally express a functional RuBisCO and a functional PRK. This is the case, for example, for photosynthetic microorganisms such as microalgae and cyanobacteria.

There are several forms of RuBisCO in nature (Tabita et al., J Exp Bot. 2008; 59(7): 1515-24. doi: 10.1093/jxb/erm361). Forms I, II and III catalyze the carboxylation and oxygenation reactions of ribulose-1,5-biphosphate. Form I is present in eukaryotes and bacteria. It consists of two types of subunits: large subunits (RbcL.) and small subunits (RbcS). The functional enzyme complex is a hexadecamer consisting of eight L subunits and eight S subunits. The correct assembly of these subunits also requires the intervention of at least one specific chaperone: RbcX (Liu et al., Nature. 2010 Jan. 14; 463(7278):197-202. doi: 10.1038/nature08651). Form II is mainly found in proteobacteria, archaea (Archaea or archaebacteria) and dinoflagellate algae. Its structure is much simpler: it is a homodimer (formed by two identical RbcL subunits). Depending on the organism, the genes encoding a type I RuBisCO may be called rbcL/rbcS (for example *Synechococcus elongatus*), or cbxLC/cbxSC, cfxLC/cfxSC, cbbL/cbbS (for example *Cupriavidus necator*). Depending on the organism, the genes encoding a type II RuBisCO are generally called cbbM (for example *Rhodospirillum rubrum*). Form III is present in the archaea. It is generally found in the form of dimers of the RbcL subunit, or in pentamers of dimers. Depending on the organism, the genes encoding a type III RuBisCO may be called rbcL (for example *Thermococcus kodakarensis*), cbbL (for example *Haloferax* sp.).

Two classes of PRKs are known: class I enzymes found in proteobacteria are octamers, while class II enzymes found in cyanobacteria and plants are tetramers or dimers. Depending on the organism, the genes encoding a PRK may be called prk (for example *Synechococcus elongatus*), prkA (for example *Chlamydomonas reinhardtii*), prkB (for example *Escherichia coli*), prk1, prk2 (for example *Leptolyngbya* sp.), cbbP (for example *Nitrobacter vulgaris*) or cfxP (for example *Cupriavidus necator*).

In the case where the microorganism used does not naturally express a functional RuBisCO and a functional PRK, said microorganism is genetically modified to express heterologous RuBisCO and PRK. Advantageously, in such a case, the microorganism is transformed so as to integrate into its genome one or more expression cassettes integrating the sequences encoding said proteins, and advantageously the appropriate transcription factors. Depending on the type of RuBisCO to be expressed, it may also be necessary to have one or more chaperone proteins expressed by the microorganism, in order to promote the proper assembly of the subunits forming the RuBisCO. This is particularly the case for type I RuBisCO, where the introduction and expression of genes encoding a specific chaperone (Rbcx) and generalist chaperones (GroES and GroEL, for example) are necessary to obtain a functional RuBisCO. Application WO2015/107496 describes in detail how to genetically modify a yeast to express a functional type I RuBisCO and PRK. It is also possible to refer to the method described in GUADALUPE-MEDINA et al. (Biotechnology for Biofuels, 6, 125, 2013).

In one embodiment, the microorganism is genetically modified to express a type I RuBisCO. In another embodiment, the microorganism is genetically modified to express a type II RuBisCO. In another embodiment, the microorganism is genetically modified to express a type III RuBisCO.

Tables 1 and 2 below list, as examples, sequences encoding RuBisCO and PRK that can be used to transform a microorganism to express a functional RuBisCO and a functional PRK.

TABLE 1

Examples of sequences encoding a RuBisCO

| Gene | Gen Bank | GI | Organism |
| --- | --- | --- | --- |
| rbcL | BAD78320.1 | 56685098 | *Synechococcus elongatus* |
| rbcS | BAD78319.1 | 56685097 | *Synechococcus elongatus* |
| cbbL2 | CAJ96184.1 | 113529837 | *Cupriavidus necator* |
| cbbS | P09658.2 | 6093937 | *Cupriavidus necator* |
| cbbM | YP_427487.1 | 132036 | *Rhodospirillum rubrum* |
| cbbM | Q21YM9.1 | 115502580 | *Rhodoferax ferrireducens* |
| cbbM | Q479W5.1 | 115502578 | *Dechloromonas aromatica* |
| rbcL | O93627.5 | 37087684 | *Thermococcus kodakarensis* |
| cbbL | CQR50548.1 | 811260688 | *Haloferax* sp. Arc-Hr |

TABLE 2

Examples of sequences encoding a PRK

| Gene | Gen Bank | GI | Organism |
| --- | --- | --- | --- |
| prk | BAD78757.1 | 56685535 | *Synechococcus elongatus* |
| cfXP | P19923.3 | 125575 | *Cupriavidus necator* |
| PRK | P09559.1 | 125579 | *Spinacia oleracea* |
| cbbP | P37100.1 | 585367 | *Nitrobacter vulgaris* |

Inhibition of Glycolysis

According to the invention, the glycolysis pathway is at least partially inhibited, so that the microorganism is no longer able to use this metabolic pathway normally (FIG. 1—glycolysis). In other words, the microorganism no longer has the ability to assimilate glucose in a similar way to a wild-type microorganism, in which the glycolysis pathway has not been inhibited (independently of any other genetic modification).

In one particular embodiment, the microorganism is genetically modified to inhibit, totally or partially, glycolysis downstream of the production of glyceraldehyde-3-phosphate (G3P).

For example, glycolysis is inhibited upstream of the production of 1,3-biphospho-D-glycerate (1,3-BPG) or upstream of the production of 3-phosphoglycerate (3PG).

Depending on the microorganism, the reactions involved between glyceraldehyde-3-phosphate (G3P) and 3-phosphoglycerate (3PG) can be managed (i) by two enzymes acting concomitantly, glyceraldehyde-3-phosphate dehydrogenase (EC 1.2.1.12, abbreviated GAPDH or more rarely G3PDH) and phosphoglycerate kinase (E.C. 2.7.2.3, abbreviated PGK), or (ii) by a single non-phosphorylating glyceraldehyde 3-phosphate dehydrogenase enzyme (EC 1.2.1.9, abbreviated GAPN).

Glyceraldehyde-3-phosphate dehydrogenase (GAPDH) catalyzes the reversible conversion of G3P to 1,3-biphospho-D-glycerate (1,3-BPG), using the pair $NAD^+$/NADH as electron donor/acceptor in the direction of the reaction. Depending on the organism, the genes encoding GAPDH may be called gapA, gapB, gapC (e.g. *Escherichia coli, Arabidopsis thaliana*), GAPDH, GAPD, G3PD, GAPDHS (e.g. *Homo sapiens*), TDH1, TDH2, TDH3 (e.g. *Saccharomyces cerevisiae*), gap, gap2, gap3 (e.g. *Mycobacterium* sp., *Nostoc* sp.).

Phosphoglycerate kinase (PGK) catalyzes the reversible conversion of 1,3-BPG to 3PG, using the pair ATP/ADP as cofactor. Depending on the organism, the genes encoding PGK may be called PGK, PGK1, PGK1, PGK2, PGK3, pgkA, PGKB, PGKC, cbbK, cbbKC, cbbKP (e.g. *Cupriavidus necator*).

Non-phosphorylating glyceraldehyde-3-phosphate dehydrogenase (GAPN) catalyzes the conversion of G3P to 3PG, without going through 1,3-BPG. This reaction is catalyzed in the presence of the cofactor pair $NADP^+$/NADPH, which acts as an electron acceptor. Depending on the organism, the genes encoding GAPN may be called GAPN (e.g. *Bacillus* sp., *Streptococcus* sp.), GAPN1 (e.g. *Chlamydomonas* sp.).

In one particular example, the microorganism is genetically modified so that the expression of the gene encoding glyceraldehyde 3-phosphate dehydrogenase is at least partially inhibited. Preferentially, gene expression is completely inhibited.

Alternatively or additionally, the expression of the gene encoding phosphoglycerate kinase may also be at least partially inhibited. Preferentially, gene expression is completely inhibited.

Alternatively, the microorganism is genetically modified so that the expression of the gene encoding non-phosphorylating glyceraldehyde 3-phosphate dehydrogenase is at least partially inhibited. Preferentially, gene expression is completely inhibited.

Tables 3, 4 and 5 below list, as examples, the sequences encoding a glyceraldehyde 3-phosphate dehydrogenase, a phosphoglycerate kinase and a non-phosphorylating glyceraldehyde-3-phosphate dehydrogenase that can be inhibited depending on the target microorganism. The skilled person knows which gene corresponds to the enzyme of interest to be inhibited depending on the microorganism.

TABLE 3

Examples of sequences encoding a GAPDH

| Gene | GenBank | GI | Organism |
|---|---|---|---|
| gapA | NP_416293.1 | 947679 | *Escherichia coli* |
| TDH1 | NP_012483.3 | 398364523 | *Saccharomyces cerevisiae* |
| TDH2 | NP_012542.1 | 6322468 | *Saccharomyces cerevisiae* |
| TDH3 | NP_011708.3 | 398366083 | *Saccharomyces cerevisiae* |
| gap | ECC36949.1 | 378544675 | *Mycobacterium tuberculosis* |
| gap2 | P34917.2 | 92090599 | *Nostoc* sp. |

TABLE 4

Examples of sequences encoding a PGK

| Gene | GenBank | GI | Organism |
|---|---|---|---|
| pgk | AKL94701.1 | 831186507 | *Clostridium aceticum* |
| PGK1 | NP_009938.2 | 10383781 | *Saccharomyces cerevisiae* |
| pgk | BAG04189.1 | 166089481 | *Microcystis aeruginosa* |
| PGKA | AAG34561.2 | 22711882 | *Dictyostelium discoideum* |
| PGKB | CAJ03534.1 | 68126221 | *Leishmania major* |
| cbbKC | AAC43444.1 | 976365 | *Cupriavidus necator* |
| pgk | CAK45271.1 | 4982539 | *Aspergillus niger* |
| pgk | EAU38870.1 | 4354973 | *Aspergillus terreus* |

TABLE 5

Examples of sequences encoding a GAPN

| Gene | Gen Bank | GI | Organism |
|---|---|---|---|
| gapN | CUB58597.1 | 924094571 | *Bacillus subtilis* |
| GAPN | NP_358622.1 | 933338 | *Streptococcus pneumoniae* |
| GAPN1 | EDP03116.1 | 542583 | *Chlamydomonas reinhardtii* |

In general, the production of 3-phosphoglycerate (3PG) is no longer possible through glycolysis, or at least significantly reduced, in the genetically modified microorganism according to the invention.

In a particular exemplary embodiment, the microorganism is a yeast of the genus *Saccharomyces cerevisiae* in which the expression of the TDH1 (Gene ID: 853395), TDH2 (Gene ID: 853465) and/or TDH3 gene (Gene ID: 853106) is at least partially inhibited. In another particular exemplary embodiment, the microorganism is a yeast of the genus *Saccharomyces cerevisiae* in which the expression of the PGK1 gene (Gene ID: 5230) is at least partially inhibited.

In another exemplary embodiment, the microorganism is a yeast of the genus *Saccharomyces cerevisiae* in which the expression of the PGK1 gene (Gene ID: 5230), the expression of the TDH1 gene (Gene ID: 853395), TDH2 (Gene ID: 853465) and/or the expression of the TDH3 gene (Gene ID: 853106) are at least partially inhibited.

In a particular exemplary embodiment, the microorganism is an *Escherichia coli* bacterium in which the expression of the gapA gene (Gene ID: 947679) is at least partially inhibited.

In another particular exemplary embodiment, the microorganism is an *Escherichia coli* bacterium in which the expression of the pgk gene (Gene ID: 947414) is at least partially inhibited.

In another exemplary embodiment, the microorganism is an *E. coli* bacterium in which the expression of the pgk gene (Gene ID: 947414), and/or the expression of the gapA gene (Gene ID: 947679) are at least partially inhibited.

Figure 2:
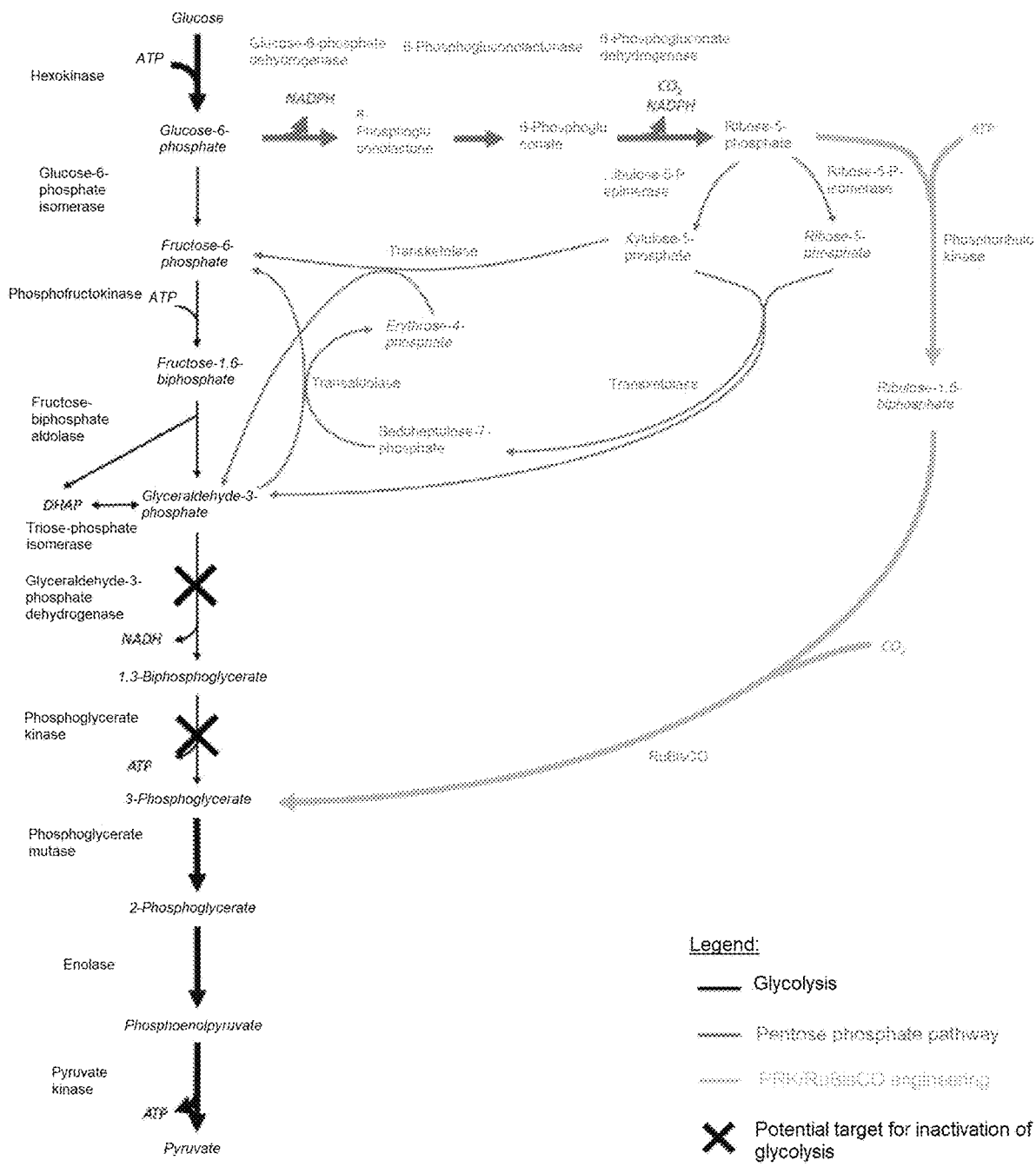
FIG. 2: Schematic representation of inhibition of the glycolysis pathway, according to the invention.

According to the invention, the genetically modified microorganism, which expresses a functional RuBisCO and a functional PRK, is on the other hand capable of producing 3PG by capturing $CO_2$ from ribulose-5-phosphate produced by the pentose phosphate pathway (FIG. 2).

Since the enzymes necessary for the metabolism of 3PG to pyruvate are not inhibited in the microorganism, said microorganism can then metabolize 3PG to produce pyruvate and ATP.

Thus, the genetically modified microorganism is able to produce pyruvate and NADPH cofactors using $CO_2$ as complementary carbon source.

In the context of the invention, "complementary" carbon source means that the microorganism uses $CO_2$ as a partial carbon source, in addition to the carbon atoms provided by fermentable sugars (glucose, galactose, sucrose, fructose, etc.), which constitute the majority or main carbon source for pyruvate production.

Thus, the genetically modified microorganism according to the invention makes it possible to increase carbon yield, by fixing and using the $CO_2$ normally lost during glucose metabolism via the pentose phosphate pathway, for the production of pyruvate (and subsequently molecules of interest).

Inhibition of the Oxidative Branch of the Pentose Phosphate Pathway

In one particular embodiment, the genetically modified microorganism according to the invention is also modified in such a way that the oxidative branch of the pentose phosphate pathway is also at least partially inhibited.

Preferentially, the microorganism is genetically modified to inhibit the oxidative branch of the pentose phosphate pathway upstream of ribulose-5-phosphate production (FIG. 1—pentose phosphate pathway).

The interruption of the oxidative branch of the pentose phosphate pathway upstream of ribulose-5-phosphate (Ru5P) production specifically targets one or more reactions in the Ru5P synthesis process from glucose-6-phosphate (G6P). This synthesis is generally catalyzed by the successive actions of three enzymes: (i) glucose-6-phosphate dehydrogenase (EC. 1.1.1.49, abbreviated G6PDH), (ii) 6-phosphogluconolactonase (E.C. 3.1.1.31, abbreviated PGL), and (iii) 6-phosphogluconate dehydrogenase (EC 1.1.1.44, abbreviated PGD).

Glucose-6-phosphate dehydrogenase (G6PDH) catalyzes the first reaction of the pentose phosphate pathway, i.e. the oxidation of glucose-6-phosphate to 6-phosphogluconolactone (6PGL), with concomitant reduction of one molecule of NADP$^+$ to NADPH. Depending on the organism, the genes encoding G6PDH may be called G6PD (for example in *Homo sapiens*), G6pdx (for example in *Musculus*), gsdA (for example in *Aspergillus nidulans*), zwf (for example in *Escherichia coli*), or ZWF1 (for example in *Saccharomyces cerevisiae*).

6-Phosphogluconolactonase (PGL) is a hydrolase that catalyzes the synthesis of 6-phosphogluconate (6PGA) from 6PGL. Depending on the organism, the genes encoding PGL may be called pgl (for example in *Escherichia coli, Synechocystis* sp.) pgls (for example in Rhodobacteraceae bacterium), or SOL (for example in *Saccharomyces cerevisiae*).

6-Phosphogluconate dehydrogenase (PGD) is an oxidoreductase that catalyzes the synthesis of Ru5P from 6PGA, with concomitant reduction of an NADP$^+$ molecule to NADPH and emission of a $CO_2$ molecule. Depending on the organism, the genes encoding PGD may be called gnd (for example in *Escherichia coli, Saccharomyces cerevisiae*), PGD (for example in *Homo sapiens*), gntZ (for example in *Bacillus subtilis*), or 6-PGDH (for example in *Lactobacillus paracollinoides*).

In one particular example, the microorganism is genetically modified so that the expression of the gene encoding glucose-6-phosphate dehydrogenase is at least partially inhibited. Preferentially, gene expression is completely inhibited.

Alternatively or additionally, the microorganism is genetically modified so that the expression of the gene encoding 6-phosphogluconolactonase is at least partially inhibited. Preferentially, gene expression is completely inhibited.

Alternatively or additionally, the microorganism is genetically modified so that the expression of the gene encoding 6-phosphogluconate dehydrogenase is at least partially inhibited. Preferentially, gene expression is completely inhibited.

Tables 6, 7 and 8 below list, as examples, the sequences encoding a glucose-6-phosphate dehydrogenase, a 6-phosphogluconolactonase and a 6-phosphogluconate dehydrogenase that can be inhibited depending on the target microorganism. The skilled person knows which gene corresponds to the enzyme of interest to be inhibited depending on the microorganism.

TABLE 6

Examples of sequences encoding a G6PDH

| Gene | GenBank | GI | Organism |
|---|---|---|---|
| zwf | BAA15660.1 | 946370 | *Escherichia coli* |
| ZWF1 | NP_014158.1 | 6324088 | *Saccharomyces cerevisiae* |
| gsdA | CAA54841.1 | 1523786 | *Aspergillus nidulans* |
| gsdA | CAK37895.1 | 4979751 | *Aspergillus niger* |
| gsdA | EAU38380.1 | 4316232 | *Aspergillus terreus* |

TABLE 7

Examples of sequences encoding a PGL

| Gene | Gen Bank | GI | Organism |
|---|---|---|---|
| pgl | BAA35431.1 | 4062334 | *Escherichia coli* |
| pgl | BAK51770.1 | 339275283 | *Synechocystis* |
| pgls | KPQ07176.1 | 938272062 | *Rhodobacteraceae bacterium* |
| SOL3 | KZV10901.1 | 1023943655 | *Saccharomyces cerevisiae* |

TABLE 8

Examples of sequences encoding a PGD

| Gene | Gen Bank | GI | Organism |
|---|---|---|---|
| gnd | ALI40222.1 | 937519736 | *Escherichia coli* |
| GND1 | EDN62420.1 | 151944127 | *Saccharomyces cerevisiae* |
| gntZ | NP_391888.1 | 16081060 | *Bacillus subtilis* |
| 6-PGDH | WP_054711110.1 | 938929230 | *Lactobacillus paracollinoides* |

In general, the production of ribulose-5-phosphate (Ru5P) is no longer possible through the pentose phosphate pathway, or at least significantly reduced, in the genetically modified microorganism according to the invention.

In a particular exemplary embodiment, the microorganism is a yeast of the genus *Saccharomyces cerevisiae* in which the expression of the ZWF1 gene is at least partially inhibited.

In one particular example, the yeast of the genus *Saccharomyces cerevisiae* is genetically modified so that the expression of the TDH1, TDH2, TDH3 and/or PGK1 genes, and the expression of the ZWF1 gene are at least partially inhibited.

In another particular exemplary embodiment, the microorganism is a bacterium of the genus *Escherichia coli* in which the expression of the zwf gene is at least partially inhibited.

In one particular example, the bacterium of the genus *Escherichia coli* is genetically modified so that the expression of the gapA and/or pgk genes, and the expression of the zwf gene are at least partially inhibited.

In another example, the microorganism is a filamentous fungus of the genus *Aspergillus*, such as *Aspergillus niger* or *Aspergillus terreus*, genetically modified so that the expression of the pgk and gsdA genes is partially inhibited.

Figure 3:
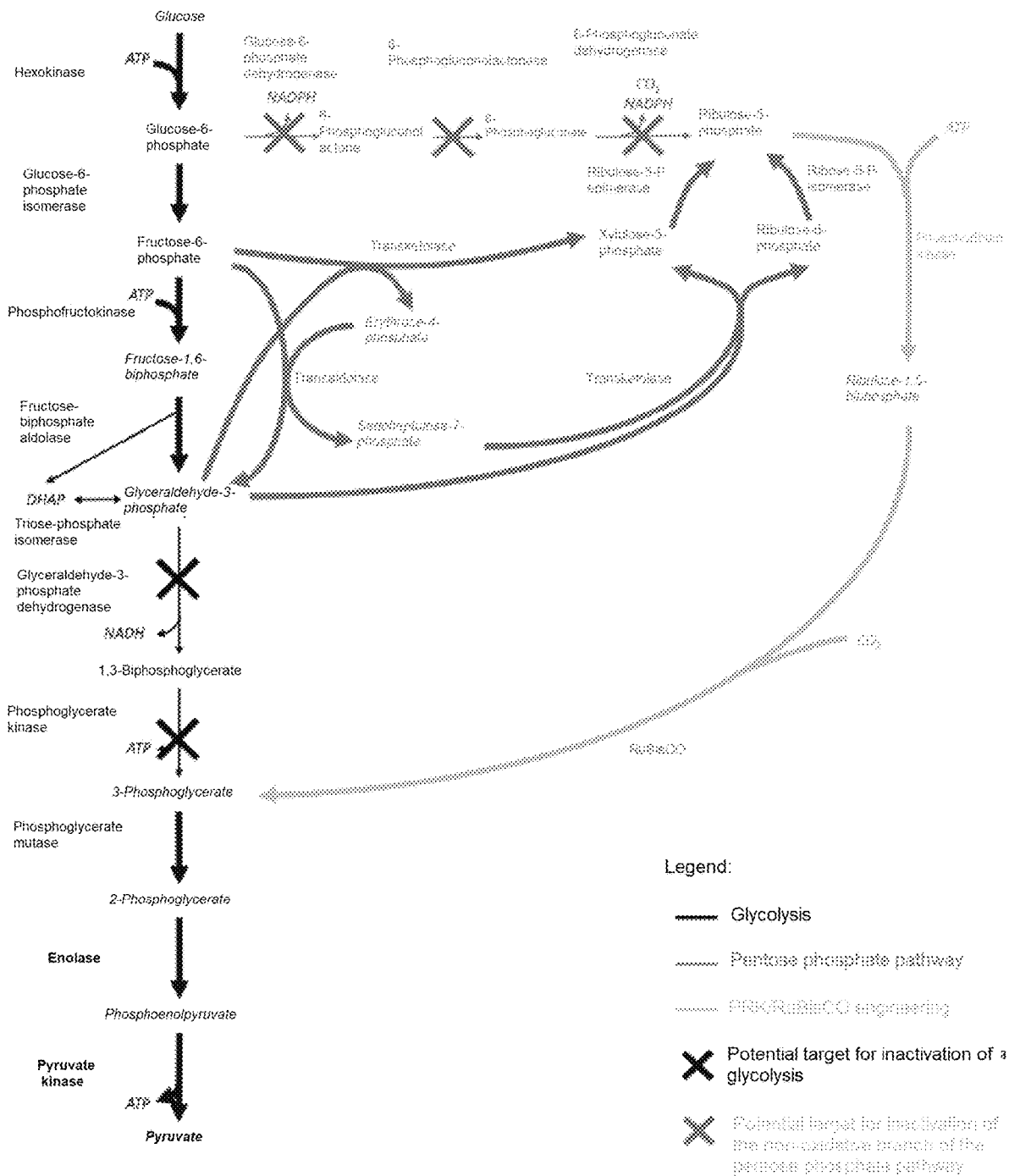
FIG. 3: Schematic representation of inhibition of the glycolysis pathway, combined with inhibition of the oxidative branch of the pentose phosphate pathway, according to the invention.

According to the invention, the genetically modified microorganism, which expresses a functional RuBisCO and a functional PRK, and whose glycolysis pathway and oxidative branch of the pentose phosphate pathway are at least partially inhibited, is no longer capable of producing 3PG via the glycolysis pathway or Ru5P via the oxidative branch of the pentose phosphate pathway. On the other hand, it is capable of producing Ru5P by diverting the production of fructose-6-phosphate (F6P) and/or glyceraldehyde-3-phosphate (G3P), produced at the beginning of glycolysis (upstream of inhibition). This production is possible thanks to the enzymes transketolase (EC 2.2.1.1), transaldolase (EC 2.2.1.2), ribose-5-phosphate isomerase (EC 5.3.1.6), and ribulose-5-phosphate epimerase (EC 5.1.3.1) naturally present and active in the microorganisms (FIG. 3).

Since the enzymes necessary for the metabolism of 3PG to pyruvate are not inhibited in the microorganism according to the invention, said microorganism can then metabolize 3PG to produce pyruvate and ATP.

Thus, the genetically modified microorganism is able to produce pyruvate by using exogenous $CO_2$ as complementary carbon source.

Thus, the genetically modified microorganism according to the invention makes it possible to increase the carbon yield, by fixing and using exogenous $CO_2$, for the production of pyruvate (and subsequently molecules of interest). Here again, there is an increase in carbon yield.

Inhibition of the Entner-Doudoroff Pathway

In one particular embodiment, the genetically modified microorganism according to the invention has an Entner-Doudoroff pathway, and this is at least partially inhibited. This pathway, mainly found in bacteria (especially Gram-negative bacteria), is an alternative to glycolysis and the pentose pathway for the production of pyruvate from glucose. More precisely, this pathway connects to the pentose phosphate pathway at P-gluconate to feed glycolysis, particularly at pyruvate.

Preferentially, the microorganism is genetically modified to inhibit Entner-Doudoroff pathway reactions downstream of 6-phosphogluconate production. This inhibition eliminates a possible competing pathway, and ensures the availability of 6-phosphogluconate as a substrate for PRK/RuBisCO engineering.

The interruption of the Entner-Doudoroff pathway downstream of 6-phosphogluconate production specifically targets one or more reactions in the pyruvate synthesis process from 6-phosphogluconate. This synthesis is initiated by the successive actions of two enzymes: (i) 6-phosphogluconate dehydratase ("EDD"—EC. 4.2.1.12), and (ii) 2-dehydro-3-deoxy-phosphogluconate aldolase ("EDA"—E.C. 4.1.2.14).

6-Phosphogluconate dehydratase catalyzes the dehydration of 6-phosphogluconate to 2-keto-3-deoxy-6-phosphogluconate. Depending on the organism, the genes encoding 6-phosphogluconate dehydratase may be called edd (GenBank NP_416365, for example, in *Escherichia coli*), or ilvD (for example, in *Mycobacterium* sp.).

2-Dehydro-3-deoxy-phosphogluconate aldolase catalyzes the synthesis of a pyruvate molecule and a glyceraldehyde-3-phosphate molecule from the 2-keto-3-deoxy-6-phosphogluconate produced by 6-phosphogluconate dehydratase. Depending on the organism, the genes encoding 2-dehydro-3-deoxy-phosphogluconate aldolase may be called eda (GenBank NP_416364, for example, in *Escherichia coli*), or kdgA (for example in *Thermoproteus tenax*), or dgaF (for example in *Salmonella typhimurium*).

In one particular example, the microorganism is genetically modified so that the expression of the gene encoding 6-phosphogluconate dehydratase is at least partially inhibited. Preferentially, gene expression is completely inhibited.

Alternatively or additionally, the microorganism is genetically modified so that the expression of the gene encoding 2-dehydro-3-deoxy-phosphogluconate aldolase is at least partially inhibited. Preferentially, gene expression is completely inhibited.

Tables 9 and 10 below list, as examples, the sequences encoding a 6-phosphogluconate dehydratase and a 2-dehydro-3-deoxy-phosphogluconate aldolase that can be inhibited depending on the target microorganism. The skilled person knows which gene corresponds to the enzyme of interest to be inhibited depending on the microorganism.

TABLE 9

Examples of sequences encoding an EDD

| Gene | GenBank | GI | Organism |
|---|---|---|---|
| edd | NP_416365.1 | 16129804 | *Escherichia coli* |
| ilvD | CND70554.1 | 893638835 | *Mycobacterium tuberculosis* |
| edd | AJQ65426.1 | 764046652 | *Salmonella enterica* |

TABLE 10

Examples of sequences encoding an EDA

| Gene | GenBank | GI | Organism |
|---|---|---|---|
| eda | AKF72280.1 | 817591701 | *Escherichia coli* |
| kdgA | Q704D1.1 | 74500902 | *Thermoproteus tenax* |
| eda | O68283.2 | 81637643 | *Pseudomonas aeruginosa* |

In general, in this embodiment, pyruvate production is no longer possible via the Entner-Doudoroff pathway, or at least significantly reduced.

In a particular exemplary embodiment, the microorganism is a bacterium of the genus *Escherichia coli* in which the expression of the edd gene is at least partially inhibited.

In one particular example, the bacterium of the genus *Escherichia coli* is genetically modified so that the expression of the gapA, and edd genes are at least partially inhibited.

According to the invention, the genetically modified microorganism, which expresses a functional RuBisCO and a functional PRK, and whose glycolysis pathway and Entner-Doudoroff pathway are at least partially inhibited, is no longer capable of producing 3PG by glycolysis or pyruvate by the Entner-Doudoroff pathway. The carbon flow from glucose is therefore preferably directed towards PRK/RuBisCO engineering.

Production of Molecules of Interest

According to the invention, the genetically modified microorganism is transformed so as to produce an exogenous molecule of interest and/or to overproduce an endogenous molecule of interest.

In the context of the invention, molecule of interest preferentially refers to a small organic molecule with a molecular mass less than or equal to 0.8 kDa.

In general, genetic modifications made to the microorganism, as described above, improve the carbon yield of the synthesis and/or bioconversion pathways of molecules of interest.

In the context of the invention, "improved" yield refers to the quantity of the finished product. In general, in the context of the invention, the carbon yield corresponds to the ratio of quantity of finished product to quantity of fermentable sugar, particularly by weight. According to the invention, the carbon yield is increased in the genetically modified microorganisms according to the invention, compared with wild-type microorganisms, placed under identical culture conditions. Advantageously, the carbon yield is increased by 2%, 5%, 10%, 15%, 18%, 20%, or more. The genetically modified microorganism according to the invention may produce a larger quantity of molecules of interest (finished product) than heterologous molecules produced by a genetically modified microorganism simply to produce or overproduce that molecule. According to the invention, the genetically microorganism may also overproduce an endogenous molecule compared with the wild-type microorganism. The overproduction of an endogenous molecule is mainly understood in terms of quantities. Advantageously, the genetically modified microorganism produces at least 20%, 30%, 40%, 50%, or more by weight of the endogenous molecule than the wild-type microorganism. Advantageously, the microorganism according to the invention is genetically modified so as to produce or overproduce at least one molecule among amino acids, terpenoids, terpenes, vitamins and/or vitamin precursors, sterols, flavonoids, organic acids, polyols, polyamines, aromatic molecules obtained from stereospecific hydroxylation, via an NADP-dependent cytochrome p450, etc.

In one particular example, the microorganism is genetically modified to overproduce at least one amino acid, preferentially selected from arginine, lysine, methionine, threonine, proline, glutamate, homoserine, isoleucine, valine, and γ-aminobutyric acid.

In one particular example, the microorganism is genetically modified to produce or overproduce molecules from the terpenoid pathway, such as farnesene, and from the terpene pathway.

In one particular example, the microorganism is genetically modified to produce or overproduce a vitamin or precursor, preferentially selected from pantoate, pantothenate, transneurosporene, phylloquinone and tocopherols.

In one particular example, the microorganism is genetically modified to produce or overproduce a sterol, preferentially selected from squalene, cholesterol, testosterone, progesterone and cortisone.

In one particular example, the microorganism is genetically modified to produce or overproduce a flavonoid, preferentially selected from frambinone and vestinone.

In one particular example, the microorganism is genetically modified to produce or overproduce an organic acid, preferentially selected from coumaric acid, 3-hydroxypropionic acid, citric acid, oxalic acid, succinic acid, and itaconic acid.

In one particular example, the microorganism is genetically modified to produce or overproduce a polyol, preferentially selected from sorbitol, xylitol and glycerol.

In one particular example, the microorganism is genetically modified to produce or overproduce a polyamine, preferentially spermidine.

In one particular example, the microorganism is genetically modified to produce or overproduce an aromatic molecule from a stereospecific hydroxylation, via an NADP-dependent cytochrome p450, preferentially selected from phenylpropanoids, terpenes, lipids, tannins, fragrances, hormones.

In the case where the molecule of interest is obtained by bioconversion, the genetically modified microorganism is advantageously cultured in a culture medium including the substrate to be converted. In general, the production or overproduction of a molecule of interest by a genetically modified microorganism according to the invention is obtained by culturing said microorganism in an appropriate culture medium known to the skilled person.

The term "appropriate culture medium" generally refers to a sterile culture medium providing essential or beneficial nutrients for the maintenance and/or growth of said microorganism, such as carbon sources; nitrogen sources such as ammonium sulfate; sources of phosphors, for example, potassium phosphate monobasic; trace elements, for example, salts of copper, iodide, iron, magnesium, zinc or molybdate; vitamins and other growth factors such as amino acids or other growth promoters. An antifoam agent can be added as needed. According to the invention, this appropriate culture medium may be chemically defined or complex. The culture medium may thus be identical or similar in composition to a synthetic medium, as defined by Verduyn et al. (Yeast. 1992. 8:501-17), adapted by Visser et al. (Biotechnology and bioengineering. 2002. 79:674-81), or commercially available such as yeast nitrogen base (YNB) medium (MP Biomedicals or Sigma-Aldrich).

In particular, the culture medium may include a simple carbon source, such as glucose, galactose, sucrose, molasses, or the by-products of these sugars, optionally supplemented with $CO_2$ as carbon co-substrate. According to the present invention, the simple carbon source must allow the normal growth of the microorganism of interest. It is also possible, in some cases, to use a complex carbon source, such as lignocellulosic biomass, rice straw, or starch. The use of a complex carbon source usually requires pretreatment before use.

In one particular embodiment, the culture medium contains at least one carbon source among monosaccharides such as glucose, xylose or arabinose, disaccharides such as sucrose, organic acids such as acetate, butyrate, propionate or valerate to promote different kinds of polyhydroxyalkanoate (PHA), treated or untreated glycerol.

Depending on the molecules to be produced and/or overproduced, it is possible to exploit the supply of nutritional factors (N, O, P, S, K, Mg, Fe, Mn, Co, Cu, Ca, Sn; Koller et al., Microbiology Monographs, G.-Q. Chen, 14: 85-119, (2010)). This is particularly the case to promote the synthesis and intracellular accumulation of polyhydroalkanoate (PHA) including polyhydroxybutyrate (PHB).

According to the invention, any culture method allowing the production on an industrial scale of molecules of interest can be considered. Advantageously, the culture is done in bioreactors, especially in batch, fed-batch and/or continuous culture mode. Preferentially, the culture associated with the production of the molecule of interest is in fed-batch mode corresponding to a controlled supply of one or more substrates, for example by adding a concentrated glucose solution whose concentration can be between 200 g/L. and 700 g/L. A controlled supply of vitamins during the process can also be beneficial to productivity (Alfenore et al., Appl Microbiol Biotechnol. 2002. 60:67-72). It is also possible to add an ammonium salt solution to limit the nitrogen supply.

Fermentation is generally carried out in bioreactors, with possible steps of solid and/or liquid precultures in Erlenmeyer flasks, with an appropriate culture medium containing at least a simple carbon source and/or an exogenous $CO_2$ supply, necessary for the production of the molecule of interest.

In general, the culture conditions of the microorganisms according to the invention are easily adaptable by the skilled person, depending on the microorganism and/or the molecule to be produced/overproduced. For example, the culture temperature is between 20° C. and 40° ° C. for yeasts, preferably between 28° C. and 35° C., and more particularly around 30° C., for S. cerevisiae. The culture temperature is between 25° C. and 35°C, preferably 30° C., for Cupriavidus necator.

The invention therefore also relates to the use a genetically modified microorganism according to the invention, for the production or overproduction of a molecule of interest, preferentially selected from amino acids, peptides, proteins, vitamins, sterols, flavonoids, terpenes, terpenoids, fatty acids, polyols and organic acids.

The invention also relates to a biotechnological process for producing at least one molecule of interest, characterized in that it comprises a step of culturing a genetically modified microorganism according to the invention, under conditions allowing the synthesis or bioconversion, by said microorganism, of said molecule of interest, and optionally a step of recovering and/or purifying said molecule of interest.

In one particular embodiment, the microorganism is genetically modified to express at least one enzyme involved in the synthesis of said molecule of interest.

In another particular embodiment, the microorganism is genetically modified to express at least one enzyme involved in the bioconversion of said molecule of interest.

The invention also relates to a process for producing a molecule of interest comprising (i) inserting at least one sequence encoding an enzyme involved in the synthesis or bioconversion of said molecule of interest into a recombinant microorganism according to the invention, (ii) culturing said microorganism under conditions allowing the expression of said enzyme and optionally (iii) recovering and/or purifying said molecule of interest.

For example, it is possible to overproduce citrate by a fungus, particularly a filamentous fungus, such as *Aspergillus niger*, genetically modified to express a functional PRK and a functional type I or II RuBisCO, and in which the expression of the pgk (Gene ID: 4982539) and gsdA (Gene ID: 497979751) genes is at least partially inhibited.

It is also possible to overproduce itaconic acid by a fungus, particularly a filamentous fungus, such as *Aspergillus terreus* or *Aspergillus niger*, genetically modified to express a functional PRK and a functional type I or II RuBisCO, and in which the expression of the pgk (Gene ID: 4354973) and gsdA (Gene ID: 4316232) genes is at least partially inhibited.

Similarly, it is possible to produce farnesene by a yeast such as a yeast of the genus *Saccharomyces cerevisiae* genetically modified to express a functional PRK and a functional type I or II RuBisCO, a farnesene synthase and in which the expression of a PGK1 gene (Gene ID: 5230) is at least partially inhibited.

It is also possible to overproduce glutamate by a bacterium, such as a bacterium of the genus *Escherichia coli*, genetically modified to express a functional PRK and a functional type I or II RuBisCO, and in which the expression of the gapA gene (Gene ID: 947679) is at least partially inhibited. This overproduction can also occur in a strain where at least partial inhibition of the gapA gene is combined with at least partial inhibition of the zwf gene (Gene ID: 946370).

Similarly, it is also possible to overproduce γ-aminobutyric acid by a bacterium, such as a bacterium of the genus *Escherichia coli*, genetically modified to express a functional PRK and a functional type I or II RuBisCO, as well as a glutamate decarboxylase gadB (Gene ID: 946058), and in which the expression of the gapA gene (Gene ID: 947679) is at least partially inhibited. This overproduction can also occur in a strain where at least partial inhibition of the gapA gene is combined with at least partial inhibition of the zwf gene (Gene ID: 946370).

Similarly, it is possible to overproduce succinic acid and oxalic acid by a bacterium, such as a bacterium of the genus *Escherichia coli*, genetically modified to express a functional PRK and a functional type I or II RuBisCO, as well as an enzymatic activity allowing the oxidation of glyoxylate to oxalate, preferentially a glyoxylate dehydrogenase FPGLOXDH1 (mRNA: BAH29964.1), a glyoxylate oxidase GLO (mRNA: AOW73106.1), or a lactate dehydrogenase LDHA (Gene ID: 3939), and in which the expression of the gapA (Gene ID: 947679) and zwf (Gene ID: 946370) genes is at least partially inhibited.

EXAMPLES

Example 1: Bioinformatics Analysis a) Calculation of Theoretical Yields
i) Comparison of Carbon Fixation Yields from Glucose Between a Wild-Type Strain Using the Pentose Phosphate Pathway and Glycolysis and a Modified Strain According to the Invention In order to evaluate the benefit of the modifications described according to the invention, theoretical yield calculations were carried out on the basis of the stoichiometry of the reactions involved.

Two scenarios were analyzed: the improvement provided by PRK-RuBisCO engineering (i) in a strain inhibited for glycolysis on the yield of a NADPH-dependent biosynthetic pathway (for example farnesene synthesis), and (ii) in a strain inhibited for glycolysis and for the oxidative branch of the pentose phosphate pathway on the yield of a biosynthetic pathway of interest (for example citrate synthesis).

In the context of the improvement of NADPH-dependent biosynthetic pathways, the theoretical balance of the formation of NADPH and glyceraldehyde-3-phosphate (G3-P) from glucose via the pentose phosphate pathway was calculated according to the following equation (1):

$$3 \text{ Glucose} + 5 \text{ ATP} + 6 \text{ NADP}^+ + 3 \text{ H}_2\text{O} \rightarrow 5 \text{ G3-P} + 5 \text{ ADP} + 6 \text{ NADPH} + 11 \text{ H}^+ + 3 \text{ CO}_2 \quad (1)$$

Going down to pyruvate formation from G3P, we arrive at the following balance:

$$3 \text{ Glucose} + 5 \text{ ADP} + 6 \text{ NADP}^+ + 5 \text{ NAD}^+ + 5 \text{ P}_i \rightarrow 5 \text{ Pyruvate} + 5 \text{ ATP} + 6 \text{ NADPH} + 5 \text{ NADH} + 11 \text{ H}^+ + 3 \text{ CO}_2 + 2 \text{ H}_2\text{O} \quad (2)$$

If we normalize the balance for one mole of glucose, we obtain the following yield:

$$\text{Glucose} + 1.67\ \text{ADP} + 2\ \text{NADP}^+ + 1.67\ \text{NAD}^+ + 1.67\ P_i \rightarrow 1.67\ \text{Pyruvate} + 1.67\ \text{ATP} + 2\ \text{NADPH} + 1.67\ \text{NADH} + 3.67\ \text{H}^+ + \text{CO}_2 + 0.67\ \text{H}_2\text{O} \quad (3)$$

Thus, by using the pentose phosphate pathway, 1.67 moles of pyruvate and 2 moles of NADPH are produced from one mole of glucose. However, one mole of carbon is lost by decarboxylation when ribulose-5-phosphate is formed by 6-phosphogluconate dehydrogenase (EC 1.1.1.44). In comparison, pyruvate formation by the glycolysis pathway gives the following yield:

$$\text{Glucose} + 2\ \text{ADP} + 2\ \text{NAD}^+ + 2\ P_i \rightarrow 2\ \text{Pyruvate} + 2\ \text{ATP} + 2\ \text{NADH}^+ 2\ \text{H}^+ + 2\ \text{H}_2\text{O} \quad (4)$$

The maximum theoretical yield of pyruvate production by the pentose phosphate pathway is therefore 0.82 $g_{pyruvate}/g_{glucose}$ (g of synthesized pyruvate, per g of glucose consumed), while it is 0.98 $g_{pyruvate}/g_{glucose}$ by the glycolysis pathway.

By integrating PRK/RuBisCO engineering into a strain inhibited for glycolysis (for example ΔPGK1 in *S. cerevisiae* yeast), the carbon fixation flux is redirected to the oxidative branch of the pentose phosphate pathway and then to PRK/RuBisCO engineering (see FIG. 2). This flux is related to the end of the glycolysis pathway, at the level of 3-phosphoglycerate (3PG) formation, with the following yield:

$$\text{Glucose} + 2\ \text{ATP} + 2\ \text{NADP}^+ + 2\ \text{H}_2\text{O} \rightarrow 2\ 3\text{PG} + 2\ \text{ADP} + 2\ \text{NADPH} + 6\ \text{H}^+ \quad (5)$$

Going down to pyruvate formation from 3PG, we arrive at the following balance:

$$\text{Glucose} + 2\ \text{NADP}^+ \rightarrow 2\ \text{Pyruvate} + 2\ \text{NADPH} + 4\ \text{H}^+ \quad (6)$$

The integration of the modifications according to the invention into a microorganism makes it possible to recover the carbon molecule otherwise lost by decarboxylation in the pentose pathway. The maximum theoretical carbon fixation yield is therefore 0.98 $g_{pyruvate}/g_{glucose}$, which improves by 20.5% the yield obtained by the production of pyruvate by the pentose phosphate pathway, while producing NADPH.

In a second case (see FIG. 3), PRK/RuBisCO engineering is integrated into a strain that is both inhibited for glycolysis (for example ΔPGK1 in the case of *S. cerevisiae* yeast) and for the oxidative branch of the pentose phosphate pathway (for example ΔZWF1 in the case of *S. cerevisiae* yeast). The theoretical balance of the formation of NADPH and 3-phosphoglycerate (3PG) from glucose then becomes $$2.5\ \text{Glucose} + 6\ \text{ATP} + 3\ \text{CO}_2 + 3\ \text{H}_2\text{O} \rightarrow 6\ 3\text{PG} + 6\ \text{ADP} + 12\ \text{H}^+ \quad (7)$$

Going down to pyruvate formation from 3PG, we arrive at the following balance $$2.5\ \text{Glucose} + 3\ \text{CO}_2 \rightarrow 6\ \text{Pyruvate} + 3\ \text{H}_2\text{O} + 6\ \text{H}^+ \quad (8)$$

If we normalize the balance for one mole of glucose, we obtain the following yield:

$$\text{Glucose} + 1.2\ \text{CO}_2 \rightarrow 2.4\ \text{Pyruvate} + 1.2\ \text{H}_2\text{O} + 2.4\ \text{H}^+ \quad (9)$$

The integration of the modifications according to the invention makes it possible to fix 1.2 additional carbon molecule per mole of glucose consumed. The corresponding maximum theoretical yield is 1.17 $g_{pyruvate}/g_{glucose}$, which is ~20% improvement compared with the carbon fixation yield of glycolysis.

ii) Application to Citrate Production

In a second case, the calculation is applied to citrate production in *S. cerevisiae* yeast, in a wild-type strain and in a modified strain modified according to the invention incorporating PRK/RuBisCO engineering and deleted for the PGK1 gene so as to inhibit the glycolysis pathway, and for the ZWF1 gene to inhibit the oxidative branch of the pentose pathway.

The production of citrate from pyruvate is summarized by the following balance equation:

$$2\ \text{Pyruvate} + \text{ATP} + \text{NAD}^+ + 2\ \text{H}_2\text{O} \rightarrow \text{Citrate} + \text{ADP} + \text{NADH} + P_i + 3\ \text{H}_+ \quad (11)$$

This synthesis does not require NADPH, but 2 moles of pyruvate. Optimally, a wild-type strain obtains these 2 moles of pyruvate by glycolysis, from one mole of glucose according to equation (4), with the following balance:

$$\text{Glucose} + \text{ADP} + 3\ \text{NAD}^+ + P_i \rightarrow \text{Citrate} + \text{ATP} + 3\ \text{NADH} + 5\ \text{H}^+ \quad (12)$$

The corresponding $g_{citrate}/g_{glucose}$ yield is 1.07

In the context of a modified strain according to the invention, inhibited for the glycolysis pathway and the pentose phosphate pathway, the 2 pyruvates required are obtained with only 0.83 mole of glucose (see equation 9), with the following balance:

$$0.83\ \text{Glucose} + \text{CO}_2 + \text{ATP} + \text{NAD}^+ + \text{H}^2\text{O} \rightarrow \text{Citrate} + \text{ADP} + \text{NADH} + P_i + 5\ \text{H}^+ \quad (13)$$

The corresponding $g_{citrate}/g_{glucose}$ yield is 1.28, a maximum theoretical increase of about 20% compared with the yield of the wild-type strain.

b) Simulation of Biosynthesis Yields by Flux Balance Analysis

In a bioinformatics approach, flux balance analyses (FBAs) were also performed to simulate the impact of the modifications described according to the invention on the yield of different biosynthetic pathways.

FBAs are based on mathematical models that simulate metabolic networks at the genome scale (Orth et al., Nat Biotechnol. 2010; 28: 245-248). Reconstructed networks contain the known metabolic reactions of a given organism and integrate the needs of the cell, in particular to ensure cell maintenance or growth. FBAs make it possible to calculate the flow of metabolites through these networks, making it possible to predict theoretical growth rates as well as metabolite production yields.

i) Procedure

FBA simulations were performed with the OptFlux software (Rocha et al., BMC Syst Biol. 2010 Apr. 19; 4:45. doi: 10.1186/1752-0509-4-45), and the *Saccharomyces cerevisiae* metabolic model iMM904 (Mo et al., BMC Syst Biol. 2009 Mar. 25; 3:37. doi: 10.1186/1752-0509-37). This model has been modified to include the improvements described according to the invention, including a heterologous $CO_2$ fixation pathway with (i) the addition of a PRK-type reaction, (ii) the addition of a RuBisCO-type reaction.

In particular exemplary embodiments, the reactions necessary to simulate the production of molecules through heterologous pathways have also been added to the model.

In a particular exemplary embodiment, a farnesene synthase reaction (EC 4.2.3.46 or EC 4.2.3.47) has been added for the heterologous production of farnesene.

In a second particular exemplary embodiment, acetoacetyl-CoA reductase (EC 1.1.1.36) and poly-hydroxybutyrate synthase (EC 2.3.1.B2 or 2.3.1.B5) reactions were added to the model to simulate a heterologous production pathway of β-hydroxyburyrate, the monomer of polyhydroxybutyrate.

In another particular exemplary embodiment, a glutamate decarboxylase reaction (EC 4.1.1.15) was added for the heterologous production of γ-aminobutyric acid.

In another particular exemplary embodiment, an aconitate decarboxylase reaction (EC 4.1.1.6) was added for the heterologous production of itaconic acid.

In another particular exemplary embodiment, a lactate dehydrogenase reaction (EC 1.1.1.27) was added for the heterologous production of oxalate The simulations were carried out by applying to the model a set of constraints reproducible by the skilled person, aimed at simulating the in vivo culture conditions of a strain of *S. cerevisiae* under the conditions described according to the invention (for example presence of unrestricted glucose in the medium, aerobic culture condition).

In particular exemplary embodiments, simulations are performed by virtually inactivating the reactions of the enzymes PGK1 (for example glutamate, ß-hydroxybutyric acid, farnesene) and ZWF1 (for example citrate production), in order to simulate the decreases in glycolysis activity and the pentose phosphate pathway, described according to the invention.

Simulations are carried out in parallel on an unmodified "wild-type strain" model in order to evaluate the impact of the improvements described according to the invention on the production yield of the biosynthetic pathways tested.

ii) Results

The theoretical yields obtained and the percentages of improvement provided by the invention are described in Table 11 below.

$CO_2$ loss and thus allow the improvement of alpha-farnesene production from glucose.

a) Inactivation of the Glycolysis Pathway

To that end, the glycolysis pathway was inactivated by deletion of the PGK1 gene. Once glycolysis is inhibited, the resulting yeast strain is no longer able to use glucose as a source of carbon and energy. It is therefore necessary to supply the biomass synthesis pathways with glycerol and the energy pathways with ethanol. The strains in which PGK1 is deleted are grown on YPGE (yeast extract peptone glycerol ethanol) medium.

The deletion of the PGK1 gene was obtained as follows:

The coding phase of the G418 resistance gene, derived from the KanMX cassette contained on plasmid pUG6 (P30114—Euroscarf), was amplified with the oligonucleotides CB101 (SEQ ID NO: 1) and CB102 (SEQ ID NO: 2):

SEQ ID NO: 1: CB101 (forward):
5'-ACAGATCATCAAGGAAGTAATTATCTACTTTTTACAACAAATATAAA

ACAATGGGTAAGGAAAAGACTCACGTTTC-3'

SEQ ID NO: 2: CB102 (reverse):
5'-GGGAAAGAGAAAAGAAAAAAATTGATCTATCGATTTCAATTCAATTC

AATTTAGAAAAACTCATCGAGCATCAAATGAAAC-3'

The underlined portion of the oligonucleotides is perfectly homologous to the Kan sequence and the rest of the sequence corresponds to the regions adjacent to the coding

TABLE 11

Maximum theoretical production yields evaluated by FBA on a wild-type strain and a modified strain according to the modifications of the patent, for the production of different molecules.

| Target molecule | Simulation conditions | Maximum theoretical production yields with a wild-type strain | | | Maximum theoretical production yields with a modified strain according to the invention | | | Percentage improvement in theoretical mass efficiency $g_X/g_{GLUC}$ provided by the invention |
|---|---|---|---|---|---|---|---|---|
| | | $Mol_X/Mol_{GLUC}$ | $CMol_X/CMol_{GLUC}$ | $g_X/g_{GLUC}$ | $Mol_X/Mol_{GLUC}$ | $CMol_X/CMol_{GLUC}$ | $g_X/g_{GLUC}$ | |
| Citrate | ΔPGK1, ΔZWF1, | 1 | 1 | 1.07 | 1.2 | 1.2 | 1.28 | +20% |
| Itaconate | ΔPGK1, ΔZWF1, | 1 | 0.83 | 0.72 | 1.2 | 1 | 0.87 | +20% |
| Glutamate | ΔPGK1 | 0.92 | 0.77 | 0.75 | 1.09 | 0.91 | 0.89 | +18.7% |
| | ΔPGK1, ΔZWF1, | 1 | 0.83 | 0.82 | 1.2 | 1 | 0.98 | +20% |
| GABA | ΔPGK1, ΔZWF1, | 1 | 0.67 | 0.57 | 1.2 | 0.8 | 0.69 | +20% |
| β-Hydroxy-butyric acid | ΔPGK1 | 0.92 | 0.61 | 0.53 | 1.09 | 0.73 | 0.63 | +18.2% |
| Farnesene Co-production | ΔPGK1 | 0.21 | 0.54 | 0.24 | 0.24 | 0.59 | 0.27 | +12.5% |
| Succinate | ΔPGK1, | 1 | 0.67 | 0.66 | 1.2 | 0.8 | 0.79 | +20% |
| Oxalate | ΔZWF1, | 1 | 0.33 | 0.5 | 1.2 | 0.4 | 0.6 | +20% |

$Mol_X/Mol_{GLUC}$: moles of molecule X produced, in relation to the moles of glucose consumed
$CMol_X/CMol_{GLUC}$: moles of carbon of molecule X produced, in relation to the moles of carbon of glucose consumed
$g_X/g_{GLUC}$: g of molecule X produced, in relation to the g of glucose consumed.

Example 2: Improvement of Farnesene Production in *S. cerevisiae*

A *Saccharomyces cerevisiae* yeast strain, CEN.PK 1605 (Mat a HIS3 leu2-3.112 trp1-289 ura3-52 MAL.28c) derived from the commercial strain CEN.PK 113-7D (GenBank: JRIV00000000 is engineered to produce NADPH without phase of the PGK1 gene on the *Saccharomyces cerevisiae* genome so as to generate a PCR amplicon containing at its ends homologous recombination sequences of the PGK1 gene locus.

For the transformation reaction according to the skilled man (Methods in Yeast Genetics, Cold Spring Harbor lab course manual, 1997; Gietz and Schiest, 1995, Methods in Molecular and Cellular Biology 5[5]:225-269), strain CEN.PK 1605 was grown in a volume of 50 mL of complex rich medium YPD (yeast extract peptone dextrose) at 30° C. to an optical density at 600 nm of 0.8. The cells were centrifuged for 5 minutes at 2,500 rpm at room temperature. The supernatant was removed and the cells were resuspended in 25 mL of sterile water and centrifuged again for 5 minutes at 2,500 rpm at room temperature. After removing the supernatant, the cells were resuspended in 400 µL of 100 mM sterile lithium acetate.

At the same time, a transformation mix was prepared in a 2 mL tube as follows: 250 µL of 50% PEG, 10 µL of "carrier" DNA at 5 mg/mL, 36 µL of 1 M lithium acetate, 5 or 10 µL of purified PCR reaction (deletion cassette) and 350 µL of water.

The resuspended cells (50 µL) were added to the transformation mixture and incubated at 42° ° C. for 40 minutes in a water bath.

After incubation, the tube was centrifuged for 1 minute at 5,000 rpm at room temperature and the supernatant was discarded. The cells were resuspended in 2 mL of YPGE (yeast extract peptone glycerol ethanol) medium, transferred to a 14 mL tube and incubated for 2 hours at 30° C. at 200 rpm. The cells were then centrifuged for 1 minute at 5,000 rpm at room temperature. The supernatant was removed and the cells were resuspended in 1 mL of sterile water and centrifuged again for 1 minute and resuspended in 100 µL of sterile water and spread over 180 µg/mL YPGE+G418.

The colonies obtained were genotyped for the validation of the deletion of the PGK1 gene and referenced EQ-0134 (CEN.PK1605 Δpgk1::kan).

b) Introduction of PRK—RuBisCO—Alpha-Farnesene Synthase Enzymes

In order to reconstitute an alternative pathway to glycolysis and allow the Δpgk1 strain to grow on glucose, said strain has been modified to allow combinatorial expression of:
- a gene encoding a phosphoribulokinase PRK which is grafted onto the pentose phosphate pathway by consuming ribulose-5P to give ribulose-1.5bisP and
- a type I RuBisCO (with the structural genes RbcL and RbcS and the chaperones RbcX, GroES and GroEL). RuBisCO consumes ribulose-1.5bisP and one mole of $CO_2$ to form 3-phosphoglycerate downstream of the PGK1 deletion in the glycolysis pathway.

This alternative pathway once again allows the strain to consume glucose as its main source of carbon and energy.

To produce apha-farnesene, the yeast lacks the alpha-farnesene synthase gene (AFS1; SEQ ID NO: 71; GenBank accession number AY182241).

Also, the seven genes required for PRK-RuBisCO engineering (Table 12) were cloned on four plasmid vectors capable of autonomous replication, with compatible origins of replication and each carrying a different gene for complementation of auxotrophy or of antibiotic resistance, allowing the selection of strains containing the three or four plasmid constructs.

Two of these plasmids are single-copy, with an Ars/CEN origin of replication and the third is multicopy with a 2µ origin.

TABLE 12

Description of expression cassettes and plasmid composition

|  | GenBank | Codon optimization | Promoter | Terminator | ori | Auxotrophic marker | Plasmids |
|---|---|---|---|---|---|---|---|
| RbcL | BAD78320.1 | Yes | TDH3p | ADH1t | 2 µ | URA3 | pFPP45 |
| RbcS | BAD78319.1 | Yes | TEF1p | PGK1t | 2 µ | URA3 | pFPP45 |
| RbcX | BAD80711.1 | Yes | TEF1p | PGK1t | ARS-CEN6 | LEU2 | pFPP56 |
| GroES | U00096 | No | PGI1p | CYC1t | ARS-CEN6 | LEU2 | pFPP56 |
| GroEL | AP009048 | No | TDH3p | ADH1t | ARS-CEN6 | LEU2 | pFPP56 |
| PRK | BAD78757.1 | Yes | Tet-OFF | CYC1t | ARS416-CEN4 | TRP1 | pFPP20 |
| alpha-farnesene synthase (AFS1) | AY182241 | Yes | TEF1p | PGK1t | 2 µ | NatMX | pL4 |
| Empty |  |  | Tet-OFF | CYC1t | ARS416-CEN4 | TRP1 | pCM185 |
| Empty |  |  |  |  | ARS-CEN6 | LEU2 | pFL36 |
| Empty |  |  | TEF1p | PGK1t | 2 µ | URA3 | pV51TEF |

Genes from *Synechococcus elongatus* such as rbcL, rbcS, rbcX and prk (as described in WO) 2015107496 A1) and *Malus domestica* alpha-farnesene synthase (Tippmann et al., Biotechnol Bioeng. 2016 January; 113(1):72-81) have been optimized for the use of codons in *Saccharomyces cerevisiae* yeast.

According to the protocol previously described for yeast transformation, strain EQ-0134 was grown in a volume of 50 mL of complex rich medium YPGE (yeast extract peptone glycerol ethanol) at 30° C. The cells are centrifuged for 5 minutes at 2,500 rpm at room temperature. The supernatant is removed and the cells are resuspended in 25 mL of sterile water and centrifuged again for 5 minutes at 2,500 rpm at room temperature. After removing the supernatant, the cells are resuspended in 400 µL of 100 mM sterile lithium acetate.

At the same time, the following transformation mix is prepared: 250 µL of 50% PEG, 10 µL of "carrier" DNA at 5 mg/mL, 36 µL of 1 M lithium acetate, 10 µL (3 µg of one of the following combinations, pFPP45+pFPP56+pFPP20 or pL4+pFPP45+pFPP56+pFPP20) and 350 µL of water.

The resuspended cells (50 µL) were added to the transformation mixture and incubated at 42° C. for 40 minutes in a water bath. After incubation, the tube was centrifuged for 1 minute at 5,000 rpm at room temperature and the supernatant was discarded. The cells were resuspended in 2 mL YNB (yeast nitrogen base including ammonium sulfate) with glycerol and ethanol, transferred to a 14 mL tube and incubated for 2 hours at 30° C. under atmosphere enriched with 10% $CO_2$. The final mix is spread on YNB agar medium including ammonium sulfate+CSM without LUW (leucine uracil, tryptophan)+nourseothricin if applicable, with glycerol and ethanol as carbon sources.

According to the previously described protocol, strain CEN.PK 1605 is transformed with the following plasmid combination: pL4+pFL36+pCM185+pV51TEF.

The clones obtained were genotyped for all engineering genes and then adapted on liquid medium YNB ammonium sulfate and glucose.

EQ-0153 (CEN.PK1605 Δpgk1::kan) (pFPP45+pFPP56+ pFPP20)

EQ-0253 (CEN.PK1605 Δpgk1::kan) (pL4+pFPP56+ pFPP20+pFPP45)

EQ-0353 (CEN.PK1605) (pL4+pFL36+pCM185+ pV51TEF)

c) Adaptation of Strains EQ-0153 and EQ-0253 to Growth in Liquid Medium with Glucose and $Co_2$.

Batch-mode cultures in Erlenmeyer flasks are carried out with the appropriate culture medium and a 10% exogenous $CO_2$ supply, in a shaking incubator (120 rpm, 30° C.), with inoculation at 0.05 OD 600 nm measured using an EON spectrophotometer (BioTek Instruments). The strain of interest is grown on YNB+CSM-LUW medium with 10 g/L glycerol and 7.5 g/L ethanol, under conditions where PRK expression is not induced, and in the presence of nourseothricin if appropriate. Under these conditions, it is necessary to feed the strain before and after the deletion of the PGK1 gene.

After obtaining a sufficient quantity of biomass, cultures with a volume greater than or equal to 50 mL in Erlenmeyer flasks of at least 250 ml are inoculated in order to adapt the strain to the use of the PRK/RuBisCO engineering. This adaptation is carried out on YNB+CSM-LUW culture medium with 20 g/L glucose, in the presence of nourseothricin if necessary and an exogenous $CO_2$ supply as described above.

After observation of a significant growth start, the strains are adapted to a minimum mineral medium free of the amino acids and nitrogenous bases included in the CSM-LUW, i.e. only YNB with 20 g/L glucose, nourseothricin if necessary and an exogenous $CO_2$ supply as described above.

d) Production of Farnesene in Erlenmeyer Flasks

*Saccharomyces cerevisiae* strain EQ-0253, with a deletion in the glycolytic pathway at the PGK1 gene, is grown to produce farnesene while overproducing NADPH without $CO_2$ loss, using a PRK and a RuBisCO.

This strain of interest is compared with a reference strain EQ-0353 producing farnesene following the introduction of a heterologous alpha-farnesene synthase, without deletion of PGK1 or addition of PRK and RuBisCO.

Strains EQ-0253 (CEN.PK1605 Δpgk1::kan) (pL4+ pFPP56+pFPP20+pFPP45) and EQ-0353 (CEN.PK1605) (pL4+pFL36+pCM185+pV51TEF) were grown in a YNB medium with 20 g/L D-glucose, to which 100 µg/L nourseothricin was added. A pre-culture containing 20 mL of culture medium was inoculated at 0.05 $OD_{600nm}$ into a 250 mL baffled Erlenmeyer flask, shaken at 120 rpm for 24 h at 30° C. in a Minitron incubator with an atmosphere regulated at 10% $CO_2$. From the first pre-culture, 50 mL of medium was inoculated at 0.05 $OD_{600nm}$ into a 250 mL Erlenmeyer and shaken at 120 rpm for 24 h at 30° C., 10% $CO_2$. The culture, also conducted in Erlenmeyer flasks (500 mL, baffled) from the second pre-culture, was inoculated at 0.05 $OD_{600nm}$ into 100 mL of the same culture medium, to which 50 g/mL ampicillin, 10 µL antifoam (Antifoam 204, Sigma, A6426) and 10% (v/v) dodecane were added (Tippman et al., Talanta (2016), 146: 100-106). The cultures were shaken at 120 rpm at 30° C. in the presence of 10% $CO_2$. Growth was monitored by measuring turbidity at 600 nm.

To extract farnesene, 500 µL of organic phase was collected and centrifuged at 5,000 g for 5 min for complete separation of the two phases. The organic phase was stored at 4° C. until GC-MS analysis. The detection and quantification of α-farnesene was performed by single quadrupole mass spectrometry. A Zebron ZB-FFAP column was used with hydrogen as the carrier gas at a fixed rate of 2.95 mL/min. The inlet temperature was 260° C., 1 µL of sample was injected in splitless mode. The initial oven temperature was 70° ° C. (4 min) then it was gradually increased to 160°C (7°C/min) then to 240° C. (40° C./min) where it was maintained for 1.05 min. For mass spectrometric detection, the transfer line and source temperatures were 250° C. and 200° C. respectively. The mass acquisition was made between t=10 min and t=20 min. An external calibration including seven points was performed using the farnesene isomer mix (Sigma, W383902) for the quantification of α-farnesene produced by the strains.

To quantify the glucose consumed by the strains, 500 µL of culture medium was collected at the same farnesene extraction OD, centrifuged at 5,000 g, 5 min at 4° C. The supernatant was filtered (Minicart RC4, Sartorius 0.45 µm) and stored in a flask at −20° C. The glucose contained in this sample was quantified by UltiMate 3000 HPLC-UV (Thermo Scientific) equipped with a pump, an 8° C. refrigerated autosampler and a refractive index (RI) detector (Precision Instruments IOTA 2). A Rezex ROA-Organic Acid H$^+$ column (8%) 150×7.8 mm, 8 µm particle size (Phenomenex, 00H-0138-KO) was used with a Carbo-H pre-column 4×3.0 mm. The temperature of the column was 35° ° C. and the flow rate was set at 0.5 mL/min. Isocratic elution was performed with an aqueous mobile phase at 5 mM $H_2SO_4$ and lasted 30 min. A volume of 20 µL was injected for each sample. The identification of compounds was based on the comparison of retention times with standards. The external calibration includes 10 points of variable glucose concentration (0-20 g/L).

The carbon yield $Y_{\alpha-farnesene/Glc}$ is calculated in grams of farnesene produced per gram of glucose consumed for both strains EQ-0253 and EQ-0353, $$Y_{\alpha-farnesene/Glc} = \frac{\text{farnesene (mg/L aqueous)}}{\text{glucose (mg/L aqueous)}}.$$

TABLE 13

Mass yield of α-farnesene to D-glucose

| Strains | $Y_{\alpha-farnesene/glucose}$ (×10$^4$)(g/g) | Yield improvement |
|---|---|---|
| EQ-0253 | 12.5 | +9.6% |
| EQ-0353 | 11.4 | |

The increase in the mass yield of α-farnesene to D-glucose observed was 9.6% for strain EQ-0253, compared with control strain EQ-0353.

Example 3: Improvement of Citrate Production in *S. cerevisiae* a) Inactivation of the ZWF1 Gene and the IDH1 Gene in a Haploid Strain of Mating Type MAT a Inactivation of the ZWF1 gene The coding phase of the hygromycin B resistance gene, derived from the hphMX cassette (loxP-pAgTEF1-hph-tAgTEF1-loxP) and contained on plasmid pUG75 (P30671)—Euroscarf), is amplified with the oligonucleotides Sdzwf1 and Rdzwf1 (Table 14). This makes it possible to generate a Δzwf1 PCR amplicon containing at its ends homologous recombination sequences of the glucose-6-phosphate dehydrogenase ZWF1 gene locus.

TABLE 14

Oligonucleotides

| Name | Sequence |
|---|---|
| Sdzwf1 (SEQ ID NO: 3) | AAGAGTAAATCCAATAGAATAGAAAACCACATAAGG CAAG<u>ATGGGTAAAAAGCCTGAACTCACCG</u> |
| Rdzwf1 (SEQ ID NO: 4) | ATTTCAGTGACTTAGCCGATAAATGAATGTGCTTGC ATTTTTTTATTCCTTTGCCCTCGGACG |
| Sdpgk1 (SEQ ID NO: 5) | ACAGATCATCAAGGAAGTAATTATCTACTTTTTACA ACAAATATAAAAC<u>AATGGGTAAGGAAAAGACTCACG TTTC</u> |
| Rdpgk1 (SEQ ID NO: 6) | GGGAAAGAGAAAAGAAAAAAATTGATCTATCGATTT CAATTCAATTCAAT<u>TTAGAAAAACTCATCGAGCATC AAATGAAAC</u> |
| Sdidh1 (SEQ ID NO: 7) | TCTCCCTATCCTCATTCTTCTCCCTTTTCCTCCATA ATTGTAAGAGAAAA<u>ATGGGTACCACTCTTGACGACA CGG</u> |
| Rdidh1 (SEQ ID NO: 8) | AATTTGAACACACTTAAGTTGCAGAACAAAAAAAAG GGGAATTGTTTTCAT<u>TAGGGGCAGGGCATGCTCATG TAGAGC</u> |

The underlined portion of the oligonucleotides corresponds to the portion perfectly homologous to the sequence of the selection gene, the rest of the sequence corresponding to the regions adjacent to the coding phase of the target gene to be deleted on the *Saccharomyces cerevisiae* genome.

The previously described strain CEN.PK 1605 (Mat a HIS3 leu2-3.112 trp1-289 ura3-52 MAL.28c) derived from the commercial strain CEN.PK 113-7D (GenBank: JRIV00000000) is transformed with the Δzwf1 PCR fragment described above.

For the transformation reaction, strain CEN.PK 1605 is grown in a volume of 50 mL of complex rich medium YPD (yeast extract peptone dextrose, here 20 g/L glucose) at 30° C. to an optical density at 600 nm of 0.8. The cells are centrifuged for 5 minutes at 2,500 rpm at room temperature. The supernatant is removed and the cells are resuspended in 25 mL of sterile water and centrifuged again for 5 minutes at 2,500 rpm at room temperature. After removing the supernatant, the cells are resuspended in 400 µL of 100 mM sterile lithium acetate.

At the same time, a transformation mix is prepared in a 2 mL tube as follows: 250 µL of 50% PEG, 10 µL of "carrier" DNA at 5 mg/mL, 36 µL of 1 M lithium acetate, 10 µL of purified PCR reaction (deletion cassette) and 350 µL of water.

The resuspended cells (50 µL) are added to the transformation mixture and incubated at 42° C. for 40 minutes in a water bath. After incubation, the tube is centrifuged for 1 minute at 5,000 rpm at room temperature and the supernatant is discarded. The cells are resuspended in 2 mL of YPD (yeast extract peptone dextrose) medium, transferred to a 14 mL tube and incubated for 2 hours at 30° C. at 200 rpm. The cells are then centrifuged for 1 minute at 5,000 rpm at room temperature. The supernatant is removed and the cells are resuspended in 1 mL of sterile water and centrifuged again for 1 minute and resuspended in 100 µL of sterile water and spread on YPD+HygromycinB (200 µg/mL).

The colonies obtained were genotyped for the validation of the deletion of the ZWF1 gene and referenced EQSC-002 (CEN.PK 1605 Δzwf1::hph).

Inactivation of the IDH1 gene

Inactivation of this gene allows citrate to accumulate (Rodriguez et al., Microb Cell Fact. 2016 Mar. 3; 15:48).

The coding phase of the nourseothricin resistance gene, derived from the natMX cassette (loxP-pAgTEF1-nat-tAgTEF1-loxP) contained on the plasmid (pUG74 (P30670)—Euroscarf) is amplified with the oligonucleotides Sdidh1 and Rdidh1 (Table 13). This makes it possible to generate a Δidh1 PCR amplicon containing at its ends homologous recombination sequences of the isocitrate dehydrogenase IDH1 subunit gene locus.

The strains previously described, EQSC-002 (CEN.PK 1605 Δzwf1::hph) and CEN.PK 1605 (Mat a HIS3 leu2-3.112 trp1-289 ura3-52 MAL.28c) derived from the commercial strain CEN.PK 113-7D (GenBank: JRIV00000000) are transformed with the PCR fragment for inactivation of the IDH1 gene.

For the transformation reaction, strains EQSC-002 and CEN.PK1605 are grown in a volume of 50 mL of complex rich medium YPD (yeast extract peptone dextrose, here 20 g/L glucose) at 30° C. to an optical density at 600 nm of 0.8. The cells are centrifuged for 5 minutes at 2,500 rpm at room temperature. The supernatant is removed and the cells are resuspended in 25 mL of sterile water and centrifuged again for 5 minutes at 2,500 rpm at room temperature. After removing the supernatant, the cells are resuspended in 400 µL of 100 mM sterile lithium acetate.

At the same time, a transformation mix is prepared in a 2 mL tube as follows: 250 µL of 50% PEG, 10 µL of "carrier" DNA at 5 mg/mL, 36 µL of 1 M lithium acetate, 10 µL of purified PCR reaction (deletion cassette) and 350 µL of water.

The resuspended cells (50 µL) are added to the transformation mixture and incubated at 42° C. for 40 minutes in a water bath. After incubation, the tube is centrifuged for 1 minute at 5,000 rpm at room temperature and the supernatant is discarded. The cells are resuspended in 2 mL of YPD (yeast extract peptone dextrose), transferred to a 14 mL tube and incubated for 2 hours at 30° C. at 200 rpm. The cells are then centrifuged for 1 minute at 5,000 rpm at room temperature. The supernatant is removed and the cells are resuspended in 1 mL of sterile water and centrifuged again for 1 minute and resuspended in 100 µL of sterile water and spread on YPD+HygromycinB 200 µg/mL, 50 µg/mL nourseothricin.

The colonies obtained were genotyped for the validation of the deletion of the IDH1 gene and are called EQSC-003 (CEN.PK 1605 Δzwf1::hph, Δidh1::nat) and EQSC-005 (CEN.PK 1605 Δidh1::nat)

b) Inactivation of the PGK1 Gene in a Haploid Strain of Mating Type MAT Alpha

The coding phase of the G418 resistance gene from the KanMX cassette (loxP-pAgTEF1-kanMX-tAgTEF1-loxP) contained on plasmid pUG6 (P30114)—Euroscarf is amplified with the oligonucleotides Sdpgk1 and Rdpgk1 (Table 13) to generate a Δpgk1 PCR amplicon containing at its ends homologous recombination sequences of the 3-phosphoglycerate kinase PGK1 gene locus.

Strain CEN.PK 1606 (Mat alpha HIS3 leu2-3.112 trp1-289 ura3-52 MAL.28c) derived from the commercial strain CEN.PK 113-7D (GenBank: JRIV00000000) is transformed with the PCR fragment for inactivation of the PGK1 gene.

For the transformation reaction, strain CEN.PK 1606 is grown in a volume of 50 mL of complex rich medium YPD (yeast extract peptone dextrose, here 20 g/L glucose) at 30° C. to an optical density at 600 nm of 0.8. The cells are centrifuged for 5 minutes at 2,500 rpm at room temperature. The supernatant is removed and the cells are resuspended in 25 mL of sterile water and centrifuged again for 5 minutes at 2,500 rpm at room temperature. After removing the supernatant, the cells are resuspended in 400 μL of 100 mM sterile lithium acetate.

At the same time, a transformation mix is prepared in a 2 mL tube as follows: 250 μL of 50% PEG, 10 μL of "carrier" DNA at 5 mg/mL, 36 μL of 1 M lithium acetate, 10 μL of purified PCR reaction (deletion cassette) and 350 μL of water.

The resuspended cells (50 μL) are added to the transformation mixture and incubated at 42° ° C. for 40 minutes in a water bath. After incubation, the tube is centrifuged for 1 minute at 5,000 rpm at room temperature and the supernatant is discarded. The cells are resuspended in 2 mL of YPGE (yeast extract peptone 20 g/L glycerol, 30 g/L ethanol), transferred to a 14 mL tube and incubated for 2 hours at 30° ° C. at 200 rpm. The cells are then centrifuged for 1 minute at 5,000 rpm at room temperature. The supernatant is removed and the cells are resuspended in 1 mL of sterile water and centrifuged again for 1 minute and resuspended in 100 μL of sterile water and spread over YPGE+150 μg/mL G418.

The colonies obtained were genotyped for the validation of the deletion of the PGK1 gene and referenced EQSC-008 (CEN.PK 1605, Δpgk1::kan).

c) Construction of a Strain in which IDH1, ZWF1 and PGK1 have been Inactivated by Crossing The haploid strains of opposite mating types EQSC-003 (CEN.PK 1605 Δzwf1::hph, Δidh1::nat) and EQSC-008 (CEN.PK 1606 Δpgk1::kan) are grown overnight on agar medium:YPD (yeast extract peptone dextrose) for strain EQSC-008 and YPGE (yeast extract peptone glycerol ethanol) for strain EQSC003, at 30° C. Then the two strains are crossed by direct contact on YPGE (yeast extract peptone glycerol ethanol) agar medium+150 μg/mL G418+200 μg/mL hygromycin B. The G418 and hygromycin B double selection eliminates the two parental strains, only the MAT α/MAT alpha, ZWF1/Δzwf1::hph, IDH1/Δidh1::nat, PGK1/Δpgk1::kan diploid strains grow on this medium. An isolated diploid clone from this crossing is collected. The presence of the three cassettes Δzwf1::hph, Δidh1::nat, Δpgk1::kan is validated by growth tests on YPGE (yeast extract peptone glycerol ethanol) agar medium supplemented with 150 μg/mL G418 or 200 μg/mL hygromycin B or 50 μg/mL nourscothricin. The strain obtained is referenced EQSC-009 (CEN.PK 1607, MAT α/MAT alpha, ZWF1/Δzwf1::hph, IDH1/Δidh1::nat, PGK1/Δpgk1::kan).

The previously described strain EQSC-009 (CEN.PK 1607, MAT α/MAT alpha, ZWF1/Δzwf1::hph, IDH1/Δidh1::nat, PGK1/Δpgk1::kan) is grown on YPGE (yeast extract peptone glycerol ethanol) agar medium overnight at 30° C. The cells are then placed in liquid culture in a deficient medium (Sporulation Medium, 1% potassium acetate+leucine+uracil+tryptophan) to induce meiosis of the diploid cells and thus lead to the formation of tetrads containing four haploid spores. The tetrads are spread on YNB.GE medium (yeast nitrogen base, glycerol, ethanol)+leucine+uracil+tryptophan+1 g/L glutamic acid+20 mg/L methionine+40 mg/L cysteine and immediately dissected (using a microdissector) to isolate the spores on the same medium. The spores are germinated for several days at 30° C. The genetic content of the haploid cells thus obtained is tested by growth on selective media: YPGE (yeast extract peptone glycerol ethanol) supplemented with 150 μg/mL G418 or 200 μg/mL hygromycin B or 50 μg/mL nourseothricin and their mating type is tested by crossing with two tectrix strains of mating type MAT a or MAT alpha. The colonies obtained are genotyped for the validation of the deletion of the PGK1, IDH1, ZWF1 genes and the absence of transcripts corresponding to these genes is validated by real-time PCR after reverse transcription of ribonucleic acids. One of the strains obtained is referenced EQSC-004 (CEN.PK 1606 MAT alpha Δzwf1::hph, Δidh1::nat, Δpgk1::kan)

d) Introduction of PRK-RuBisCO Enzymes

The six genes required for PRK-RuBisCO engineering (Table 15 below) are cloned on three plasmid vectors capable of autonomous replication, with compatible origins of replication and each carrying a different auxotrophic complementation gene, allowing the selection of strains containing the three plasmid constructs (see WO 2015107496). Two of these plasmids are single-copy with an ARS/CEN origin of replication and the third is multicopy with a 2μ origin.

TABLE 15

Description of expression cassettes and plasmid composition

| | GenBank | Codon optimization | Promoter | Terminator | ori | Auxotrophic marker | Plasmids |
|---|---|---|---|---|---|---|---|
| RbcL | BAD78320.1 | Yes | TDH3p | ADH1t | 2 μ | URA3 | pFPP45 |
| RbcS | BAD78319.1 | Yes | TEF1p | PGK1t | 2 μ | URA3 | pFPP45 |
| RbcX | BAD80711.1 | Yes | TEF1p | PGK1t | ARS-CEN6 | LEU2 | pFPP56 |
| GroES | U00096 | No | PGI1p | CYC1t | ARS-CEN6 | LEU2 | pFPP56 |
| GroEL | AP009048 | No | TDH3p | ADH1t | ARS-CEN6 | LEU2 | pFPP56 |
| PRK | BAD78757.1 | Yes | Tet-OFF | CYC1t | ARS416-CEN4 | TRP1 | pFPP20 |
| Empty | | | Tet-OFF | | ARS416-CEN4 | TRP1 | pCM185 |
| Empty | | | TEF1p | PGK1t | 2 μ | URA3 | pV51TEF |
| Empty | | | | | ARS-CEN6 | LEU2 | pFL36 |

According to the transformation protocol previously described, strain EQSC-004 (CEN.PK 1606 Δzwf1::hph, Δidh1::nat, Δpgk1::kan) was grown in a volume of 50 mL of complex rich medium YPGE (yeast extract peptone glycerol ethanol) at 30° C. to an optical density at 600 nm of 0.8. The cells are centrifuged for 5 minutes at 2,500 rpm at room temperature. The supernatant is removed and the cells are resuspended in 25 mL of sterile water and centrifuged again for 5 minutes at 2,500 rpm at room temperature. After removing the supernatant, the cells are resuspended in 400 µL of 100 mM sterile lithium acetate.

At the same time, a transformation mix is prepared in a 2 mL tube as follows: 250 µL of 50% PEG, 10 µL of "carrier" DNA at 5 mg/mL, 36 µL of 1 M lithium acetate, 10 µL (3 µg) of a combination of pFPP45+pFPP56+pFPP20 and 350 µL of water.

The resuspended cells (50 µL) are added to the transformation mixture and incubated at 42° C. for 40 minutes in a water bath. After incubation, the tube is centrifuged for 1 minute at 5,000 rpm at room temperature and the supernatant is discarded. The cells are resuspended in 2 mL of YPGE (yeast extract peptone glycerol ethanol)+2 mg/L doxycycline, transferred into a 14 mL tube and incubated for 2 hours at 30° C. at 200 rpm. The cells are then centrifuged for 1 minute at 5,000 rpm at room temperature. The supernatant is removed and the cells are resuspended in 1 mL of sterile water and centrifuged again for 1 minute and resuspended in 100 µL of sterile water and spread over YNB.GE (yeast nitrogen base, glycerol, ethanol)+1 g/L glutamic acid+20 mg/L methionine+40 mg/L cysteine+2 mg/L doxycycline. The strain obtained is referenced: EQSC-006 (CEN.PK 1606 Δzwf1::hph, Δidh1::nat, Δpgk1::kan) (pFPP45+pFPP56+pFPP20).

According to the transformation protocol previously described, strain EQSC-005 (CEN.PK 1605 Δidh1::nat) was grown in a volume of 50 mL of complex rich medium YPGE (yeast extract peptone glycerol ethanol) at 30° ° C. to an optical density at 600 nm of 0.8. The cells are centrifuged for 5 minutes at 2,500 rpm at room temperature. The supernatant is removed and the cells are resuspended in 25 mL of sterile water and centrifuged again for 5 minutes at 2,500 rpm at room temperature. After removing the supernatant, the cells are resuspended in 400 µL of 100 mM sterile lithium acetate.

At the same time, a transformation mix is prepared in a 2 mL tube as follows: 250 µL of 50% PEG, 10 µL of "carrier" DNA at 5 mg/mL, 36 µL of 1 M lithium acetate, 10 µL (3 µg) of a combination of pV51TEF+pFL36+pCM185 and 350 µL of water.

The resuspended cells (50 µL) are added to the transformation mixture and incubated at 42° ° C. for 40 minutes in a water bath. After incubation, the tube is centrifuged for 1 minute at 5,000 rpm at room temperature and the supernatant is discarded. The cells are resuspended in 2 mL of YPD (yeast extract peptone dextrose), transferred to a 14 mL tube and incubated for 2 hours at 30° C. at 200 rpm. The cells are then centrifuged for 1 minute at 5,000 rpm at room temperature. The supernatant is removed and the cells are resuspended in 1 mL of sterile water and centrifuged again for 1 minute and resuspended in 100 µL of sterile water and spread on YNBD (yeast nitrogen base dextrose)+2 mg/L doxycycline. The strain obtained is referenced: EQSC-007 (CEN.PK 1605 Δidh1::nat) (pV51TEF+pFL36+pCM185).

d) Adaptation and Evolution Phase of Strains EQSC-006 and EQSC-007

Adaptation of strains EQSC-006 and EQSC-007 to growth on YNB (yeast nitrogen base) liquid medium with glucose and $CO_2$.

Batch-mode cultures in Erlenmeyer flasks are carried out with the appropriate culture medium and a 10% exogenous $CO_2$ supply, in a shaking incubator (120 rpm, 30° C.), with inoculation at 0.05 OD 600 nm measured using an EON spectrophotometer (BioTek Instruments). The strain of interest is grown on YNB+CSM-LUW medium with 10 g/L glycerol and 7.5 g/L ethanol, +50 mg/L glutamate under conditions where PRK expression is not induced.

After obtaining a sufficient quantity of biomass, cultures with a volume greater than or equal to 50 mL in Erlenmeyer flasks of at least 250 mL are inoculated in order to adapt the strain to the use of the PRK/RuBisCO engineering. This adaptation is carried out on YNB+CSM-LUW culture medium with 20 g/L glucose, 50 mg/L glutamate and an exogenous $CO_2$ supply as described above.

After observation of a significant growth start, the strains are adapted to a minimum mineral medium free of all amino acids except those indicated below, and nitrogenous bases included in the CSM-LUW, i.e. only YNB with, in final concentrations, 20 g/L glucose, 1 g/L glutamate, 40 mg/L L-cysteine and 20 mg/L L-methionine and an exogenous $CO_2$ supply as described above.

e) Production of Citrate in Erlenmeyer Flasks

*Saccharomyces cerevisiae* strain EQSC-006, with a deletion in the glycolytic pathway at the PGK1 gene, in the oxidative part of the pentose phosphate pathway and in the Krebs cycle, is grown to produce citrate without $CO_2$ loss, using PRK and RuBisCO. This strain of interest is compared with a reference strain EQSC-007 producing citrate following inactivation of the IDH1 gene, without deletion of PGK1 or ZWF1 or addition of PRK and RuBisCO.

Strains EQSC-006 (CEN.PK 1605 Δzwf1::hph, Δidh1::nat, Δpgk1::kan, pFPP45+pFPP56+pFPP20) and EQSC-007 (CEN.PK 1605 Δidh1::nat, pV51TEF+pFL36+pCM185) were cultured in yeast nitrogen base (YNB) medium supplemented with 20 g/L D-glucose (YNB D20).

In order to establish the citrate to glucose mass yields, a pre-culture containing 20 mL of culture medium was inoculated at 0.05 $OD_{600nm}$ into a 250 mL baffled Erlenmeyer flask, shaken at 120 rpm at 30° C. From the first pre-culture, 50 mL of medium was inoculated at 0.05 $OD_{600nm}$ into a 250 mL Erlenmeyer flask and shaken at 120 rpm, at 30° C. The culture was carried out in Erlenmeyer flasks (500 mL, baffled) from the second pre-culture, inoculated at 0.05 $OD_{600nm}$ into 100 mL of the same medium, at 30° C., 120 rpm. Growth was monitored by measuring turbidity at 600 nm.

For citrate quantification, 500 µL of culture medium was collected, centrifuged at 5,000 g, 5 min, 4°C. The supernatant was filtered (Minicart RC4, Sartorius 0.45 µm) and stored in a flask at −20° ° C. before HPLC analysis (Thermo Scientific UltiMate 3000 HPLC) coupled to a single quadrupole mass spectrometer. Each sample (20 µL) was injected into an Aminex HPX-87H H$^+$ column, 300 mm×7.8 mm (Bio-Rad, 125-0140). An isocratic elution at a flow rate of 0.5 mL/min was carried out with an aqueous solution of 0.037% formic acid (v/v) whose pH was adjusted to 4.5 with ammonium hydroxide. The column oven temperature was 65° C. The mass spectrometry analytical conditions were: negative electrospray mode, source temperature 450° C., needle voltage 3 kV, cone voltage 50 V. A seven-point external calibration was performed using a commercial sodium citrate solution.

To quantify the glucose consumed by the strains, 500 µL of the culture medium was collected, at the same culture $OD_{600nm}$ as for citrate quantification, centrifuged at 5,000 g, 5 min at 4° C. The supernatant was filtered (Minicart RC4, Sartorius 0.45 µm) and stored in a flask at −20° C. The glucose contained in this sample was quantified by HPLC-RI UltiMate 3000 (Thermo Scientific) equipped with a pump, an 8° C. refrigerated autosampler and a refractive index (RI) detector (Precision Instruments IOTA 2). A Rezex ROA-Organic Acid H+ column (8%) 150×7.8 mm, 8 µm particle size (Phenomenex, 00H-0138-KO) was used with a Carbo-H 4×3.0 mm pre-column. The column oven temperature was 35° C. and the flow rate was set at 0.5 mL/min. A 30 min isocratic elution was performed with an aqueous mobile phase at 5 mM $H_2SO_4$. A volume of 20 µL was injected for each sample. The identification of the compounds was based on the comparison of retention times with standards. The external calibration included 10 points of variable glucose concentration (0 to 20 g/L).

The $Y_{citrate/Glc}$ mass yield was calculated in grams of citrate produced per gram of glucose consumed for both strains EQSC-006 and EQSC-007, $$Y_{citrate/Glc} = \frac{\text{citrate (mg/Laqueous)}}{\text{glucose (mg/Laqueous)}}.$$

TABLE 16

Mass yield, citrate to D-glucose

| Strains | $Y_{citrate/glucose}$ (×10$^{-3}$) (g/g) | Yield improvement |
|---|---|---|
| EQSC-006 | 2.1 | +19.5% |
| EQSC-007 | 1.8 | |

A 19.5% increase in the citrate to D-glucose mass yield was observed for strain EQSC-006 compared with control strain EQSC-007.

Example 4: Improvement of Glutamate Production in *E. coli*

Deletion of the alpha-ketoglutarate dehydrogenase gene increases glutamate production (Usuda et al. J Biotechnol. 2010 May 3; 147(1): 17-30. doi: 10.1016/j.jbiotec.2010.02.018).

In these examples, *Escherichia coli* strain K12 MG1655 with a deleted sucA gene was used. This strain is derived from a gene deletion bank (Baba et al. Mol Syst Biol. 2006; 2:2006.0008) in *Escherichia coli* and supplied by the *Coli* Genetic Stock Center under the name JW0715-2 and with reference 8786. (JW0715-2: MG1655 ΔsucA::Kan)

4A] Improvement of Glutamate Production by Inactivation of Glycolysis a) Removal of the Selection Cassette by Specific Recombination of FTR Regions by Flp Recombinase In order to be able to reuse the same deletion strategy as that used to construct strain JW0715-2 above (Rodriguez et al., 2016), the selection cassette was deleted using a recombinase.

Plasmid p707-Flpe (provided in the Quick & Easy *E. coli* Gene Deletion Red®/ET® Recombination Kit by Gene Bridges) is transformed by electroporation according to the kit protocol. The cells are selected on LB agar supplemented with 0.2% glucose, 0.0003% tetracycline and added with 0.3% L-arabinose. A counter-selection of the clones obtained is carried out by verifying that they are no longer able to grow on the same medium supplemented with 0.0015% kanamycin.

The strain obtained is called EQ.EC002: MG1655 ΔsucA b) Deletion of the Edd-Eda Operon Encoding the Entner-Doudoroff Metabolic Pathway The deletion of the edd-eda operon is performed by homologous recombination and the use of the Quick & Easy *E. coli* Gene Deletion Red®/ET® Recombination Kit (Gene Bridges) according to the supplier's protocol.

1. Oligonucleotides designed to amplify an FRT-PKG-gb2-neo-FRT resistance gene expression cassette and having a 5' sequence homologous over 50 nucleotides to the adjacent regions of the deletion locus, i.e. at positions 1932065-1932115 and 1934604-1934654 on the chromosome thus generating recombination arms of the cassette on the bacterial genome on either side of the entire operon.

2. The *Escherichia coli* K-12 strain EQ.EC002 is transformed by electroporation with plasmid pRedET according to the kit protocol. The colonies obtained are selected on rich complex medium LB agar with 0.2% glucose, 0.0003% tetracycline.

3. Transformation of the amplicon obtained in the first step in the presence of RedET recombinase, induced by 0.3% arabinose in liquid LB for 1 h. To that end, a second electroporation of the cells expressing RedET by the deletion cassette is performed and the colonies are selected on LB agar supplemented with 0.2% glucose, 0.0003% tetracycline and added with 0.3% L-arabinose and 0.0015% kanamycin.

4. Plasmid p707-Flpe (provided in the Quick & Easy *E. coli* Gene Deletion Red®/ET® Recombination Kit by Gene Bridges) is transformed by electroporation according to the kit protocol. The cells are selected on LB agar supplemented with 0.2% glucose, 0.0003% tetracycline and added with 0.3% L-arabinose. A counter-selection of the clones obtained is carried out by verifying that they are no longer able to grow on the same medium supplemented with 0.0015% kanamycin.

5. The strain obtained is called EQ.EC003: MG1655 ΔsucA Δedd-eda c) Deletion of the gapA Gene The deletion of the gapA gene is performed by homologous recombination and the use of the Quick & Easy *E. coli* Gene Deletion Red®/ET® Recombination Kit (Gene Bridges) according to the supplier's protocol.

1. Oligonucleotides designed to amplify an FRT-PKG-gb2-neo-FRT resistance gene expression cassette and having a 5' sequence homologous over 50 nucleotides to the adjacent regions of the deletion locus, i.e. the coding phase of the gene (gapA) (GenBank: X02662.1) thus generating recombination arms of the cassette on the bacterial genome.

2. The *Escherichia coli* K-12 strain EQ.EC003 is transformed by electroporation with plasmid pRedET according to the kit protocol. The colonies obtained are selected on rich complex medium LB agar with 0.2% glucose, 0.0003% tetracycline.

3. Transformation of the amplicon obtained in the first step in the presence of RedET recombinase which will be induced by 0.3% arabinose in liquid LB for 1 h. To that end, a second electroporation of the cells expressing RedET by the deletion cassette is performed and the colonies are selected on LB agar supplemented with 0.2% glycerol and 0.3% pyruvate, 0.0003% tetracycline and added with 0.3% L-arabinose and 0.0015% kanamycin.

Deletions are verified by genotyping and sequencing and the name of the strains obtained is EQ.EC002: MG1655 ΔsucA
EQ.EC003: MG1655 ΔsucA Δedd-eda
EQ.EC004: MG1655 ΔsucA Δedd-eda ΔgapA::kan d) Insertion of the Engineering Required for $CO_2$ Fixation For the recombinant expression of the different components of a type I RuBisCO in *E. coli*, the genes described in Table 17 below are cloned as a synthetic operon containing the genes described in Table 18 below.

TABLE 17

Genes encoding a PRK and type I RuBisCO system

| Genes | GenBank | Organism |
|---|---|---|
| rbcL | BAD78320.1 | *Synechococcus elongatus* |
| rbcS | BAD78319.1 | *Synechococcus elongatus* |
| rbcX | BAD80711.1 | *Synechococcus elongatus* |
| Prk | BAD78757.1 | *Synechococcus elongatus* |

TABLE 18

Composition of the expression cassettes

Structure of the synthetic operon in vector pZA11

| Plasmid | Gene A | RBS1 | Gene B | RBS2 | GeneC | RBS3 | Gene D | RBS4 | Gene E |
|---|---|---|---|---|---|---|---|---|---|
| pZA11 | | | | | | | | | |
| pEQEC005 | rbcS | D | rbcL | B | rbcX | F | | | |
| pEQEC006 | rbcS | D | rbcL | B | rbcX | F | prk | | |
| pEQEC008 | prk | | | | | | | | |

To control the expression level of these genes, ribosome binding sequences (RBS) presented in Table 19 below, with variable translation efficiencies (Levin-Karp et al., ACS Synth Biol. 2013 Jun. 21; 2(6):327-36. doi: 10.1021/sb400002n; Zelcbuch et al., Nucleic Acids Res. 2013 May; 41(9):e98) are inserted between the coding phase for each gene. The succession of each coding phase interspersed by an RBS sequence is constructed by successive insertions into a pZA11 vector (Expressys) that contains a PLtetO-1 promoter, a p15A origin of replication and an ampicillin resistance gene.

TABLE 19

RBS intercistronic sequences

| Name | RBS sequences |
|---|---|
| A (SEQ ID NO: 9) | AGGAGGTTTGGA |
| B (SEQ ID NO: 10) | AACAAAATGAGGAGGTACTGAG |
| C (SEQ ID NO: 11) | AAGTTAAGAGGCAAGA |
| D (SEQ ID NO: 12) | TTCGCAGGGGGAAG |
| E (SEQ ID NO: 13) | TAAGCAGGACCGGCGGCG |
| F (SEQ ID NO: 14) | CACCATACACTG |

Several strains are produced by electroporating the different vectors presented according to the above plan EQ.EC 005→(EQ.EC 003+pZA11): MG1655 ΔsucA Δedd-eda EQ.EC 006→(EQ.EC 004+pEQEC005): MG1655 ΔsucA Δedd-eda ΔgapA::kan (RuBisCO)

EQ.EC 007→(EQ.EC 004+pEQEC006):MG1655 ΔsucA Δedd-eda ΔgapA::kan (RuBisCO+PRK)

EQ.EC 009→(EQ.EC 004+pEQEC008): MG1655 ΔsucA Δedd-eda ΔgapA::kan (PRK)

Clones are selected on LB medium supplemented with 2 g/L glycerol and 5 g/L pyruvate and with 100 mg/L ampicillin. After obtaining a sufficient quantity of biomass, cultures with a volume greater than or equal to 50 mL in a minimum 250 mL Erlenmeyer flask are inoculated in order to adapt the strain to the use of the PRK/RuBisCO engineering. This adaptation is carried out on LB culture medium with 2 g/L glucose, and an exogenous $CO_2$ supply at 37° C. as described above.

e) Glutamate Production

For glutamate production, cells from 500 mL of LB culture are inoculated into 20 mL of MS medium (40 g/L glucose, 1 g/L $MgSO_4·7H_2O$, 20 g/L $(NH_4)_2SO_4$, 1 g/L $KH_2PO_4$, 10 mg/L $FeSO_4·7H_2O$, 10 mg/L $MnSO_4·7H_2O$, 2 g/L yeast extract, 30 g/L $CaCO_3$, 100 mg/L ampicillin at a pressure of 0.1 atmosphere $CO_2$.

Residual glutamate and glucose are measured with a bioanalyzer (Sakura Seiki). The carbon yield $Y_{p/s}$ is calculated in grams of glutamate produced per gram of glucose consumed.

This yield increases significantly by 10% for strains EQ.EC 007 (RuBisCO+PRK) compared with the control strains EQ.EC 005 (empty), EQ.EC 006 (RuBisCO only). The control strain EQ.EC 009 (PRK alone) is not viable.

4B] Improvement of Production by Inactivation of Glycolysis and of the Pentose Phosphate Oxidative Pathway a) Removal of the Selection Cassette by Specific Recombination of FTR Regions by Flp Recombinase This step is performed in the same way as example 4A] above.

The strain obtained is called EQ.EC002: MG1655 ΔsucA b) Deletion of the Zwf Gene The deletion of the zwf gene (GeneID: 946370) is performed by homologous recombination and the use of the Quick & Easy *E. coli* Gene Deletion Red®/ET® Recombination Kit (Gene Bridges) according to the supplier's protocol, as detailed in Example 4A].

The strain obtained is called EQ.EC010: MG1655 ΔsucA Δzwf c) Deletion of the gapA Gene The deletion of the gapA gene in the *Escherichia coli* K-12 strain EQ.EC010 is performed by homologous recombination and the use of the Quick & Easy *E. coli* Gene Deletion Red®/ET® Recombination Kit (Gene Bridges) according to the supplier's protocol, as detailed in Example 4A].

Deletions are verified by genotyping and sequencing and the name of the strains obtained is:

EQ.EC002: MG1655 ΔsucA

EQ.EC010: MG1655 ΔsucA Δzwf

EQ.EC011: MG1655 ΔsucA Δzwf ΔgapA d) Insertion of the Engineering Required for $CO_2$ Fixation For the recombinant expression of the different components of the functional PRK/RuBisCO system in *E. coli*, the genes described in Table 20 and encoding a type I RuBisCO, a phosphoribulokinase, a chaperone and a carbonic anhydrase are cloned as a synthetic operon containing the genes described above (Table 21).

TABLE 20

Genes encoding a type I RuBisCO, a phosphoribulokinase and a carbonic anhydrase

| Genes | GenBank | Organism |
|---|---|---|
| rbcL | BAD78320.1 | Synechococcus elongatus |
| rbcS | BAD78319.1 | Synechococcus elonyatus |
| rbcX | BAD80711.1 | Synechococcus elongatus |
| Prk | BAD78757.1 | Synechococcus elongatus |
| icfA | WP_011378036.1 | Synechococcus elongatus |

TABLE 21

Plasmid names and expression cassette composition

Structure of the synthetic operon in vector pZA11

| Plasmid | Gene A | RBS1 | Gene B | RBS2 | Gene C | RBS3 | Gene D | RBS4 | Gene E |
|---|---|---|---|---|---|---|---|---|---|
| pZA11 | | | | | | | | | |
| pEQEC006 | rbcS | D | rbcL | B | rbcX | F | prk | | |
| pEQEC007 | rbcS | D | rbcL | B | rbcX | F | prk | A | icfA |

To control the expression level of these genes, ribosome binding sequences (RBS) presented in Table 17 (see Example 4A]), with variable translation efficiencies (Levin-Karp et al., ACS Synth Biol. 2013 Jun. 21; 2(6):327-36. doi: 10.1021/sb400002n; Zelcbuch et al., Nucleic Acids Res. 2013 May; 41(9):e98) are inserted between the coding phase of each gene. The succession of each coding phase interspersed by an RBS sequence is constructed by successive insertions into a pZA11 vector (Expressys) that contains a PLtetO-1 promoter, a p15A origin of replication and an ampicillin resistance gene. The addition of a carbonic anhydrase (icfA) also allows an 15 inter-conversion of bicarbonate ions into available $CO_2$ molecules and improves the efficiency of RuBisCO.

Several strains are produced by electroporating the different vectors presented according to the plan below EQ.EC 012→(EQ.EC 002+pZA11): MG1655 ΔsucA EQ.EC 014→(EQ.EC 011+pEQEC006): MG1655 ΔsucA Δzwf ΔgapA (RuBisCO+PRK)

EQ.EC 015→(EQ.EC 011+pEQEC007): MG1655 ΔsucA Δzwf ΔgapA (RuBisCO+PRK+carbonic anhydrase)

After transformation, clones are selected on LB glycerol, pyruvate medium supplemented with 100 mg/L ampicillin. An adaptation and evolution phase of the strains with PRK and RuBisCO engineering is performed as described in Example 4A].

e) Glutamate Production

For glutamate production, cells from 500 mL of LB culture are inoculated into 20 mL of MS medium (40 g/L glucose, 1 g/L $MgSO_4 \cdot 7H_2O$, 20 g/L $(NH4)_2SO_4$, 1 g/L $KH_2PO_4$, 10 mg/L $FeSO_4 \cdot 7H_2O$, 10 mg/L $MnSO_4 \cdot 7H_2O$, 2 g/L yeast extract, 30 g/L $CaCO_3$, 100 mg/L ampicillin at a pressure of 0.1 atmosphere $CO_2$.

Residual glutamate and glucose are measured with a bioanalyzer (YSI Inc.). The carbon yield $Y_{p/s}$ is calculated in grams of glutamate produced per gram of glucose consumed.

This yield increases significantly by 15% for strains EQ.EC 014 (RuBisCO+PRK) and EQ.EC 015 (RuBisCO+PRK+carbonic anhydrase) compared with the control strains EQ.EC 012 (empty).

4C] Improvement of Production by Inactivation of Glycolysis and Oxidative Pentose Phosphate Pathway, and Overexpression of Pyruvate Decarboxylase and Glutamate Dehydrogenase.

a) Removal of the Selection Cassette by Specific Recombination of FTR Regions by Flp Recombinase This step is performed in the same way as example 4A] above.

The strain obtained is called EQ.EC002: MG1655 ΔsucA b) Deletion of the Zwf Gene The deletion of the zwf gene (GeneID: 946370) is performed by homologous recombination and the use of the Quick & Easy *E. coli* Gene Deletion Red®/ET® Recombination Kit (Gene Bridges) according to the supplier's protocol, as detailed in Example 4A]. The strain obtained is called EQ.EC010: MG1655 ΔsucA Δzwf c) Deletion of the gapA Gene The deletion of the gapA gene in the *Escherichia coli* K-12 strain EQ.EC010 is performed by homologous recombination and the use of the Quick & Easy *E. coli* Gene Deletion Red®/ET® Recombination Kit (Gene Bridges) according to the supplier's protocol, as detailed in Example 4A]. Deletions are verified by genotyping and sequencing and the name of the strains obtained is:

EQ.EC002: MG1655 ΔsucA

EQ.EC010: MG1655 ΔsucA Δzwf

EQ.EC011: MG1655 ΔsucA Δzwf ΔgapA d) Insertion of the Engineering Necessary for $CO_2$ Fixation For the recombinant expression of the different components of the functional PRK/RuBisCO system in *E. coli*, the genes described in Table 22 and encoding a type II RuBisCO, a phosphoribulokinase and a carbonic anhydrase are cloned as a synthetic operon containing the genes described above (Table 23).

TABLE 22

Genes encoding a type II RuBisCO, a phosphoribulokinase, a carbonic anhydrase, a glutamate dehydrogenase and a pyruvate carboxylase

| Genes | GenBank | Organism |
|---|---|---|
| cbbM | YP_427487.1 | Rhodospirillum rubrum |
| Prk | BAD78757.1 | Synechococcus elongatus |
| CA | YP_427143.1 | Rhodospirillum rubrum |
| gdhA | NP_416275.1 | Escherichia coli K-12 |
| pycA | NP_389369.1 | Bacillus subtilis |

TABLE 23

Plasmid names and expression cassette composition

Structure of the synthetic operon in vector pZA11

| Plasmid | Gene A | RBS1 | Gene B | RBS2 | Gene C | RBS3 | Gene D | RBS4 | Gene E |
|---|---|---|---|---|---|---|---|---|---|
| pZA11 | | | | | | | | | |
| pEQEC009 | cbbM | B | gdhA | c | pycA | E | prk | | |
| pEQEC010 | cbbM | B | gdhA | c | pycA | E | prk | D | CA |
| pEQEC011 | | B | gdhA | c | pycA | | | | |

To control the expression level of these genes, ribosome binding sequences (RBS) presented in Table 17 (see Example 4A]), with variable translation efficiencies, are inserted between the coding phase of each gene. The succession of each coding phase interspersed by an RBS sequence is constructed by successive insertions into a pZA11 vector (Expressys) that contains a PLtetO-1 promoter, a p15A origin of replication and an ampicillin resistance gene. The addition of a glutamate dehydrogenase (gdhA) and a pyruvate carboxylase (pycA) allows a better production of glutamic acid. The addition of a carbonic anhydrase (CA) also allows an interconversion of bicarbonate ions into available $CO_2$ molecules and improves the efficiency of RuBisCO.

Several strains are produced by electroporating the different vectors presented according to the plan below:

EQ.EC 016→(EQ.EC 002+pEQEC011): MG1655 ΔsucA (glutamate dehydrogenase+pyruvate carboxylase)

EQ.EC 017→(EQ.EC 011+pEQEC009): MG1655 ΔsucA Δzwf ΔgapA (RuBisCO+PRK+glutamate dehydrogenase+pyruvate carboxylase)

EQ.EC 018→(EQ.EC 011+pEQEC010): MG1655 ΔsucA Δzwf ΔgapA (RuBisCO+PRK+carbonic anhydrase+glutamate dehydrogenase+pyruvate carboxylase+carbonic anhydrase)

After transformation, clones are selected on LB glycerol, pyruvate medium supplemented with 100 mg/L ampicillin. An adaptation and evolution phase of the strains with PRK and RuBisCO engineering is performed as described in Example 4A].

e) Glutamate Production

For glutamate production, cells from 500 mL of LB culture are inoculated into 20 mL of MS medium (40 g/L glucose, 1 g/L $MgSO_4·7H_2O$, 20 g/L $(NH_4)_2SO_4$, 1 g/L $KH_2PO_4$, 10 mg/L $FeSO_4·7H_2O$, 10 mg/L $MnSO_4·7H_2O$, 2 g/L yeast extract, 30 g/L $CaCO_3$, 100 mg/L ampicillin at a pressure of 0.1 atmosphere $CO_2$.

Residual glutamate and glucose are measured with a bioanalyzer (YSI Inc.). The carbon yield $Y_{p/s}$ is calculated in grams of glutamate produced per gram of glucose consumed.

This yield increases significantly by 15% for strains EQ.EC 017 and EQ.EC 018 compared with the control strain EQ.EC 016.

Example 5: Improvement of Polyhydroxybutyrate Production in C. necator

The increase in reducing power obtained through the genetic modifications proposed according to the invention may also have a considerable gain over existing metabolic pathways.

This is the case for the bacterial strain Cupriavidus necator ATCC 17699 which naturally produces polyhydroxybutyrate (PHB). This bacterium is capable of developing under both autotrophic and heterotrophic conditions. The deletion of the gapA gene (glyceraldehyde-3-phosphate dehydrogenase NC_008313.1) diverts the metabolic flux to the pentose phosphate pathway and increases the pool of NADPH reduced nucleotides thus increasing the PHB production yield.

This C. necator H16 strain has a megaplasmid pHG1 and two chromosomes. The deletion of the gapA gene is performed by generating a vector containing the Bacillus subtilis suicide gene sacB for Gram-negative bacteria (Quandt et al., Gene. 1993 May 15; 127(1):15-21; Lindenkamp et al., Appl Environ Microbiol. 2010 August; 76(16):5373-82 and Appl Environ Microbiol. 2012 August; 78(15):5375-83).

a) Inactivation of the Entner-Doudoroff Metabolic Pathway

Two PCR amplicons corresponding to adjacent regions of the edd and eda genes (upstream of edd and downstream of eda) are cloned by restriction according to the procedure described in Srinivasan et al. (Appl Environ Microbiol. 2002 December; 68(12):5925-32), in plasmid pJQ200mp18Cm.

The modified plasmid pJQ200mp18Cm::Δedd-eda is then transformed into an E. coli strain S17-1 by the calcium chloride transformation method. The transfer of genetic material into C. necator is done by conjugation by depositing on agar a spot of C. necator culture on a dish containing a cell monolayer of S17-1 bacteria. Selection is made on nutrient broth (NT) medium at 30° C. in the presence of 10% sucrose for purposes of selection (Hogrefe et al., J Bacteriol. 1984 April; 158(1):43-8) and validated on a mineral medium containing 50 μg/mL chloramphenicol.

The deletions are validated by genotyping and sequencing. The resulting strain EQCN_002 therefore has deletions of the genes of the Entner-Doudoroff metabolic pathway edd-cda. EQCN_002: H16 Δedd-eda.

b) Inactivation of the Glycolysis Pathway

Two PCR amplicons corresponding to adjacent regions of the gapA gene are cloned by restriction according to the procedure described in Lindenkamp et al. 2012, in plasmid pjQ200mp18Tc.

The modified plasmid pjQ200mp18Tc::ΔgapA is then transformed into an E. coli strain S17-1 by the calcium chloride transformation method. The transfer of genetic material is done by conjugation by depositing on agar a spot of C. necator culture on a plate containing a cell monolayer of S17-1 bacteria. Selection is made on nutrient broth (NT) medium at 30° in the presence of 10% sucrose for purposes of selection (Hogrefe et al., J Bacteriol. 1984 April; 158(1): 43-8.) and validated on a mineral medium containing 25 ug/mL tetracycline.

The deletions are validated by genotyping and sequencing. The strain obtained, EQCN_003, therefore has a deletion of the gapA gene. EQCN_003: H16 Δedd-eda ΔgapA.

Strain EQCN_003, with a deletion in the glycolytic pathway at the gapA gene and in the Entner-Doudoroff pathway at the edd-eda genes, is grown to improve PHB production yield by fixing exogenous $CO_2$ via the use of the PRK and RuBisCO enzymes.

b) Production of PHB in a Bioreactor

The inoculum from a frozen stock is spread on solid medium at a rate of 50 to 100 µL from a cryotube incubated at 30° C. for 48 to 96 h in the presence of fructose. The expression of genes encoding RuBisCO and PRK are maintained in C. necator under heterotrophic aerobic conditions (Rie Shimizu et al., Sci Rep. 2015; 5: 11617. Published online 2015 Jul. 1.).

Batch cultures in Erlenmeyer flasks (10 mL in 50 mL, then 50 mL in 250 mL) are carried out with the appropriate culture medium, in 20 g/L fructose and a 10% exogenous $CO_2$ supply in a shaking incubator (100-200 rpm, 30° C.), with a minimum inoculation of 0.01.

The strain of interest EQCN_003 improving PHB production yield is compared with a reference strain H16 naturally accumulating PHB under heterotrophic conditions in the presence of a nutritional limitation.

The productivity of the strains is compared in bioreactors. Cultures carried out in bioreactors are seeded from solid and/or liquid amplification chains in Erlenmeyer flasks under the conditions described above. The bioreactors, of type My-control (Applikon Biotechnology, Delft, Netherlands) 750 mL or Biostat B (Sartorius Stedim, Göttingen, Germany) 2.5 L, are seeded at a density equivalent to 0.01 $OD_{620nm}$.

The accumulation of PHB is decoupled from growth. The culture is regulated at 30° C., aeration is between 0.1 VVM (gas volume/liquid volume/min) and 1 VVM in order to maintain a minimum dissolved oxygen concentration above 20% (30° C., 1 bar), shaking is adapted according to the scale of the bioreactor used. The inlet gas flow consists of air optionally supplemented with $CO_2$. $CO_2$ supplementation is between 1% and 10%. The pH is adjusted to 7 with a 14% or 7% ammonia solution. The fed-batch culture method allows a supply of non-limiting carbon substrate combined with a limitation of phosphorus or nitrogen, while maintaining a constant carbon/phosphorus or carbon/nitrogen ratio. PHB extraction and quantification are performed according to the method of Brandl et al. (Appl Environ Microbiol. 2013 July; 79(14):4433-9). The protocol consists in adding 1 mL of chloroform to 10 mg of lyophilized cells, followed by 850 µL of methanol and 150 µL of sulfuric acid. The mixture is heated for 2.5 h at 100° C., cooled and 500 ML of water is added. The two phases are separated by centrifugation and the organic phase is dried by adding sodium sulfate The samples are filtered and analyzed as described by Müller et al. (Appl Environ Microbiol. 2013 July; 79(14): 4433-9).

A comparison of wild-type C. necator H16 cultures and strain EQCN_003: H16 Δedd-eda ΔgapA shows a 5% increase in carbon yield, corresponding here to the ratio grams of PHB per gram of fructose consumed.

Example 6: Improvement of GABA Production in E. coli

An Escherichia coli K-12 strain, genetically modified to increase the yield of its glutamate production according to example 4B], can be modified to allow the constitutive expression of a glutamate decarboxylase gadB (Gene ID: 946058) and thus increase the production yield of γ-aminobutyric acid.

The deletion of the alpha-ketoglutarate dehydrogenase gene also increases glutamate production (Usuda et al. J Biotechnol. 2010 May 3; 147(1):17-30. doi: 10.1016/j.jbiotec.2010.02.018).

In this example, the following strains are used, obtained from example 4B]:
EQ.EC002: MG1655 ΔsucA
EQ.EC010: MG1655 ΔsucA Δzwf
EQ.EC011: MG1655 ΔsucA Δzwf ΔgapA a) Constitutive Overexpression of the gadB Gene Overexpression of the gadB gene is subcloned into a bacterial expression vector pZE21MCS (EXPRESSYS). This vector has a ColE1 origin of replication and a kanamycin antibiotic resistance gene.

Rapidly, the coding phase of the gadB gene (Gene ID: 946058) is amplified from the genome of strain MG1655 ΔsucA with primers homologous to the Escherichia coli K-12 genome covering positions 1570595 to U.S. Pat. Nos. 1,570,645 and 1,572,095 to 1572045. Each of these primers is coupled to floating sequences homologous over 18 nucleotides at the ends of the fragment obtained by amplifying vector pZE21MCS excluding the multiple cloning site. The two amplicons are combined according to the protocol of the In-Fusion® HD Cloning Kit User Manual—Clontech to form plasmid pEQEC030 allowing the constitutive overexpression of the gadB gene.

b) Insertion of the Engineering Required for $CO_2$ Fixation

For the recombinant expression of the different components of a functional type I RuBisCO in E. coli, the genes described in Table 17 (Example 4A]), are cloned as a synthetic operon following the construction structure described in Table 22.

Assembly of the Different Vectors

The coding sequences (CDS) of the genes described in Table 24 are amplified and assembled into blocks according to the protocol provided with the NEBuilder® HiFi DNA Assembly Master Mix Kit (E2321) so as to obtain three integration blocks described in Table 24. Each block is then amplified according to the protocol of the In-Fusion® HD Cloning Kit User Manual—Clontech to form the plasmids described below in Table 24.

TABLE 24

Composition of expression cassettes

| | Structure of the synthetic operon in vector pZA11 | | | | | | |
|---|---|---|---|---|---|---|---|
| | Block I | | Block II | | Block III | | |
| Plasmid | CDS A | RBS1 | CDS B | RBS2 | CDS C | RBS3 | CDS D |
| pZA11 | | | | | | | |
| pEQEC006 | rbcS | D | rbcL | B | rbcX | F | prk |

To control the expression level of these genes, ribosome binding sequences (RBS) presented in Table 19 (Example 4B]), with variable translation efficiencies (Levin-Karp et al., ACS Synth Biol. 2013 Jun. 21; 2(6):327-36. doi: 10.1021/sb400002n; Zelcbuch et al., Nucleic Acids Res. 2013 May; 41(9):e98) are inserted between the coding phase for each gene. The succession of each coding phase interspersed by an RBS sequence is constructed by successive insertions into a pZA11 vector (Expressys) that contains a PLtetO-1 promoter, a p15A origin of replication and an ampicillin resistance gene. The addition of a glutamate decarboxylase (gadB) also allows a conversion of glutamate to gamma-aminobutyrate (GABA).

Several strains are produced by electroporating the different vectors presented according to the plan below EQ.EC 013→(EQ.EC 002+pZA11+pEQ030): MG1655 ΔsucA+(gadB)

EQ.EC 020→(EQ.EC 011+pEQ030+pEQEC006): MG1655 ΔsucA Δzwf ΔgapA+(gadB)+(RuBisCO+PRK)

After transformation, clones are selected on LB glycerol, pyruvate medium supplemented with 100 mg/L ampicillin and 30 mg/L kanamycin. An adaptation and evolution phase of the strains with PRK and RuBisCO engineering is performed as described in Example 4A].

c) GABA Production

For the production of GABA, cells from 500 mL of LB culture are inoculated into 20 mL of MS medium (40 g/L glucose, 1 g/L $MgSO_4·7H_2O$, 20 g/L $(NH_4)_2SO_4$, 1 g/L $KH_2PO_4$, 10 mg/L $FeSO_4·7H_2O$, 10 mg/L $MnSO_4·7H_2O$, 2 g/L yeast extract, 30 g/L $CaCO_3$, 100 mg/L ampicillin and 30 mg/L kanamycin at a pressure of 0.1 atmosphere $CO_2$, at 30° C. at pH 3.5.

The GABA concentration is measured by high-performance liquid chromatography (HPLC), using an OptimaPak C18 column (4.6×150 mm, RS Tech Corporation, Daejeon, Korea). The samples are centrifuged at 12,000 rpm for 5 minutes, 100 μL of the supernatant transferred into a new Eppendorf tube. The following reagents are added to these tubes: 200 μL of 1 M sodium bicarbonate buffer (pH 9.8), 100 μL of 80 g/L dansyl chloride in acetonitrile and 600 μL of double-distilled water. The mixture is incubated at 80°C for 40 minutes. The reaction is stopped by adding 100 μL of 2% acetic acid. The mixture is centrifuged at 12,000 rpm for 5 minutes. The supernatant is then filtered through a 0.2 μm Millipore filter and analyzed by HPLC on an Agilent system using a UV detector. Derivatized samples are separated using a binary non-linear gradient using eluent A [tetrahydrofuran/methanol/sodium acetate 50 mM at pH 6.2 (5: 75: 420, by volume)] and eluent B (methanol). Residual glucose is measured with a bioanalyzer (YSI Inc.).

The carbon yield $Y_{p/s}$ is calculated in grams of GABA produced per gram of glucose consumed.

This yield increases significantly by 15% for strain EQ.EC 020 ΔsucA Δzwf ΔgapA (RuBisCO+PRK)+(GadB) compared with the control strains EQ.EC 013 ΔsucA (GadB).

Example 7: Improvement of Succinate and Oxalate Production in *E. coli*

An *Escherichia coli* K-12 strain, genetically modified to allow constitutive expression of a glyoxylate dehydrogenase FPGLOXDH1 (Gene ID: 946058) from Fomitopsis palustris, to reduce expression of the icd gene (Gene ID: 945702), and to inactivate the aceB (GeneID 948512) and sdhA (Gene ID: 945402) genes, would increase succinate and oxalic acid production yield.

The reduction in isocitrate dehydrogenase (icd) expression allows the metabolic flux to be redirected to the glyoxylic shunt. Inactivation of malate synthase (aceB) and succinate dehydrogenase (sdhA) prevents the glyoxylate and succinate, respectively, produced from being re-consumed. Deletion of the succinate dehydrogenase gene increases succinate production under aerobic conditions (Yang et al., Microbiol res. 2014 May-June; 169(5-6):432-40). Deletion of the malate synthase gene allows the accumulation of glyoxylate which will be converted to oxalate by the constitutive expression of glyoxylate dehydrogenase.

In this example, an *Escherichia coli* K-12 strain MG1655 in which the sdhA gene has been deleted is used. This strain is derived from a gene deletion bank (Baba et al. Mol Syst Biol. 2006; 2:2006.0008) in *Escherichia coli* K-12 and supplied by the *Coli* Genetic Stock Center under the name JW0715-2 and with reference 8302. (JW0713-1: MG1655 ΔsdhA::Kan).

a) Removal of the Selection Cassette by Specific Recombination of FTR Regions by Flp Recombinase In order to be able to reuse the same deletion strategy as that used to construct strain JW0715-2 above (Rodriguez et al., 2016), the selection cassette is deleted using a recombinase.

Plasmid p707-Flpe (provided in the Quick & Easy *E. coli* Gene Deletion Red®/ET® Recombination Kit by Gene Bridges) is transformed by electroporation according to the kit protocol. The cells are selected on LB agar supplemented with 0.2% glucose, 0.0003% tetracycline and added with 0.3% L-arabinose. A counter-selection of the clones obtained is carried out by verifying that they are no longer able to grow on the same medium supplemented with 0.0015% kanamycin.

The strain obtained is called EQ.EC040: MG1655 AsdhA b) Deletion of the aceB Gene The deletion of the aceB gene (GeneID 948512) is performed by homologous recombination and the use of the Quick & Easy *E. coli* Gene Deletion Red®/ET® Recombination Kit (Gene Bridges) according to the supplier's protocol.

Oligonucleotides designed to amplify an FRT-PKG-gb2-neo-FRT resistance gene expression cassette and having a 5' sequence homologous over 50 nucleotides to the adjacent regions of the deletion locus, i.e. at positions 4215428 to 4215478. and 4217129. to 4217079 on the chromosome thus generating recombination arms of the cassette on the bacterial genome on either side of the aceB gene coding sequence.

The *Escherichia coli* K-12 strain EQ.EC040 is transformed by electroporation with plasmid pRedET according to the kit protocol. The colonies obtained are selected on rich complex medium LB agar with 0.2% glucose, 0.0003% tetracycline.

Transformation of the amplicon obtained in the first step in the presence of RedET recombinase, induced by 0.3% arabinose in liquid LB for 1 h. To that end, a second transformation of the deletion cassette is performed by electroporation in cells expressing RedET and the colonies are selected on LB agar supplemented with 0.2% glucose, 0.0003% tetracycline and added with 0.3% L-arabinose and 0.0015% kanamycin.

Plasmid p707-Flpe (provided in the Quick & Easy *E. coli* Gene Deletion Red®/ET® Recombination Kit by Gene Bridges) is transformed by electroporation according to the kit protocol. The cells are selected on LB agar supplemented with 0.2% glucose, 0.0003% tetracycline and added with 0.3% L-arabinose. A counter-selection of the clones obtained is carried out by verifying that they are no longer able to grow on the same medium supplemented with 0.0015% kanamycin.

The strain obtained is called EQ.EC041: MG1655 AsdhA AaceB c) Change in the Icd Gene Promoter i. Strategy The replacement of the native promoter of the icd gene (Gene ID: 945702) by a weaker promoter is performed by homologous recombination and the use of the Quick & Easy *E. coli* Gene Deletion Red®/ET® Recombination Kit (Gene Bridges) according to the supplier's protocol.

ii. Introduction of the Weak Promoter P Oxb1

The icd gene promoter is replaced by a cassette coupling the promoter $P_{oxb1}$, characterized as weak, and an antibiotic resistance gene cassette to allow the selection of the insertion of the $P_{oxb1}$ cassette with an antibiotic resistance gene.

Oligonucleotides designed to amplify an FRT-PKG-gb2-neo-FRT resistance gene expression cassette and having a 5' sequence homologous over 50 nucleotides to the left adjacent region of the $P_{icd}$ promoter locus (Genomic target LA) for the sense oligo, i.e. at positions 1194911 to 1194961 on the genome, and the Spacer R sequence (Table 23) for the reverse oligo allow amplification of a fragment allowing assembly with the $P_{oxb1}$ fragment.

Oligonucleotides designed to amplify the $P_{oxb1}$ promoter from plasmid PSF-OXB1 (Sigma #OGS553) and having a 5' sequence homologous over 50 nucleotides to the right adjacent region of the Pied promoter locus (Genomic target RA) for the reverse oligo, i.e. at positions 1195173 to 1195123 on the genome, and the Spacer S sequence (Table 25) for the oligo produce amplification of the $P_{oxb1}$ fragment.

The amplification of a fusion fragment using the NEBuilder® HiFi DNA Assembly Master Mix Kit (E2321) allows the replacement promoter to be combined with an antibiotic selection cassette.

TABLE 25

Primer sequences for amplifying the OXB1 gene promoter

| Name | Sequences of homology with vector PSF-OXB1 |
| --- | --- |
| POXB1-S (SEQ ID NO: 15) | TCGTTGCGTTACACACAC |
| POXB1-R (SEQ ID NO: 16) | TGTGTCGAGTGGATGGTAG |
| Spacer S (SEQ ID NO: 17) | GCATGAATTCG |
| Spacer R (SEQ ID NO: 18) | CGAATTCATGC |

The *Escherichia coli* K-12 strain EQ.EC041 is transformed by electroporation with plasmid pRedET according to the kit protocol. The colonies obtained are selected on rich complex medium LB agar with 0.2% glucose, 0.0003% tetracycline.

Transformation of the amplicon obtained in the first step in the presence of RedET recombinase, induced by 0.3% arabinose in liquid LB for 1 hour. To that end, a second transformation of the deletion cassette is performed by electroporation in cells expressing RedET and the colonies are selected on LB agar supplemented with 0.2% glucose, 0.0003% tetracycline and added with 0.3% L-arabinose and 0.0015% kanamycin.

Plasmid p707-Flpe (provided in the Quick & Easy *E. coli* Gene Deletion Red®/ET® Recombination Kit by Gene Bridges) is transformed by electroporation according to the kit protocol. The cells are selected on LB agar supplemented with 0.2% glucose, 0.0003% tetracycline and added with 0.3% L-arabinose. A counter-selection of the clones obtained is carried out by verifying that they are no longer able to grow on the same medium supplemented with 0.0015% kanamycin.

The strain obtained is called EQ.EC042: MG1655 ΔsdhA ΔaceB $P_{icd}$::$P_{oxb1}$ d) Deletion of the zwf Gene The deletion of the zwf gene (GeneID: 946370) is performed by homologous recombination and the use of the Quick & Easy *E. coli* Gene Deletion Red®/ET® Recombination Kit (Gene Bridges) according to the supplier's protocol.

Oligonucleotides designed to amplify an FRT-PKG-gb2-neo-FRT resistance gene expression cassette and having a 5' sequence homologous over 50 nucleotides to the adjacent regions of the deletion locus, i.e. at positions 1934789 to U.S. Pat. Nos. 1,934,839 and 1,936,364 to 1936314 on the chromosome thus generating recombination arms of the cassette on the bacterial genome on either side of the entire operon.

The *Escherichia coli* K-12 strain EQ.EC042 is transformed by electroporation with plasmid pRedET according to the kit protocol. The colonies obtained are selected on rich complex medium LB agar with 0.2% glucose, 0.0003% tetracycline.

Transformation of the amplicon obtained in the first step in the presence of RedET recombinase, induced by 0.3% arabinose in liquid LB for 1 h. To that end, a second transformation of the deletion cassette is performed by electroporation in cells expressing RedET and the colonies are selected on LB agar supplemented with 0.2% glucose, 0.0003% tetracycline and added with 0.3% L-arabinose and 0.0015% kanamycin.

Plasmid p707-Flpe (provided in the Quick & Easy *E. coli* Gene Deletion Red®/ET® Recombination Kit by Gene Bridges) is transformed by electroporation according to the kit protocol. The cells are selected on LB agar supplemented with 0.2% glucose, 0.0003% tetracycline and added with 0.3% L-arabinose. A counter-selection of the clones obtained is carried out by verifying that they are no longer able to grow on the same medium supplemented with 0.0015% kanamycin.

The strain obtained is called EQ.EC043: MG1655 ΔsdhA ΔaceB $P_{icd}$::$P_{oxb1}$ Δzwf e) Deletion of the gapA Gene The deletion of the gapA gene is performed by homologous recombination and the use of the Quick & Easy *E. coli* Gene Deletion Red®/ET® Recombination Kit (Gene Bridges) according to the supplier's protocol.

Oligonucleotides designed to amplify an FRT-PKG-gb2-neo-FRT resistance gene expression cassette and having a 5' sequence homologous over 50 nucleotides to the adjacent regions of the deletion locus, i.e. the coding phase of the gene (gapA) (GenBank: X02662.1) thus generating recombination arms of the cassette on the bacterial genome.

The *Escherichia coli* K-12 strain EQ.EC043 is transformed by electroporation with plasmid pRedET according to the kit protocol. The colonies obtained are selected on rich complex medium LB agar with 0.2% glucose, 0.0003% tetracycline.

Transformation of the amplicon obtained in the first step in the presence of RedET recombinase is induced by 0.3% arabinose in liquid LB for 1 h. To that end, a second electroporation of the cells expressing RedET by the deletion cassette is performed and the colonies are selected on LB agar supplemented with 0.2% glycerol and 0.3% pyruvate, 0.0003% tetracycline and added with 0.3% L-arabinose and 0.0015% kanamycin.

Plasmid p707-Flpe (provided in the Quick & Easy *E. coli* Gene Deletion Red®/ET® Recombination Kit by Gene Bridges) is transformed by electroporation according to the kit protocol. The cells are selected on LB agar supplemented with 0.2% glucose, 0.0003% tetracycline and added with 0.3% L-arabinose. A counter-selection of the clones obtained is carried out by verifying that they are no longer able to grow on the same medium supplemented with 0.0015% kanamycin.

The strain obtained is called EQ.EC044: MG1655 ΔsdhA ΔaceB P$_{icd}$::P$_{oxb1}$ Δzwf ΔgapA f) Constitutive Overexpression of the FPGLOXDH1 and aceA Genes The coding sequences (CDS) of the FPGLOXDH1 (Gene ID: 946058) and aceA (Gene ID: 948517) genes subcloned into a bacterial expression vector pZE21MCS (EXPRESSYS) as synthetic operons according to the structure described in Table 24. This vector has a ColE1 origin of replication and a kanamycin antibiotic resistance gene.

Each of these primers is coupled to floating sequences homologous over 18 nucleotides at the ends of the fragment obtained by amplifying vector pZE21MCS excluding the multiple cloning site. The two amplicons are combined according to the protocol of the In-Fusion® HD Cloning Kit User Manual—Clontech to form plasmid pEQEC035 allowing the constitutive overexpression of the FPGLOXDH1 and aceA genes.

g) Insertion of the Engineering Required for $CO_2$ Fixation

For the recombinant expression of the different components of a functional type I RuBisCO in *E. coli*, the genes described in Table 17 (Example 4A]), are cloned in the form of a synthetic operon.

The coding sequences (CDS) of the genes described in the Table 2 are amplified and assembled into blocks according to the protocol provided with the NEBuilder® HiFi DNA Assembly Master Mix Kit (E2321) to obtain three integration blocks described in Table 26. Each block is then amplified according to the protocol of the In-Fusion® HD Cloning Kit User Manual-Clontech to form the plasmids described below in Table 24.)

After transformation, clones are selected on LB glycerol, pyruvate medium supplemented with 100 mg/L ampicillin and 30 mg/L kanamycin. An adaptation and evolution phase of the strains with PRK and RuBisCO engineering is performed as described in Example 4A].

h) Production of Succinate and Oxalate

For the production of succinate and oxalate, cells from 500 mL of LB culture are inoculated into 20 mL of MS medium (40 g/L glucose, 1 g/L MgSO$_4$·7H$_2$O, 20 g/L (NH$_4$)$_2$SO$_4$, 1 g/L KH$_2$PO$_4$, 10 mg/L FeSO$_4$·7H$_2$O, 10 mg/L MnSO$_4$·7H$_2$O, 2 g/L yeast extract, 30 g/L CaCO$_3$, 100 mg/L ampicillin and 30 mg/L kanamycin at a pressure of 0.1 atmosphere CO$_2$, at 30° C. at pH 3.5.

The succinate concentration is measured by high-performance liquid chromatography (HPLC), culture samples are centrifuged at 12,000 g for 5 min.

i. Succinate Determination

The culture supernatant is filtered through a 0.2 μm Millipore filter and analyzed on an Agilent HPLC system (series 1100) equipped with a cation-exchange column. (Aminex HPX87-H, Bio-Rad, Hercules, CA, USA), a UV absorbance detector (Agilent Technologies, G1315D) and a refractive index (RI) detector (Agilent Technologies, HP1047A). The samples are separated on a 5 mM H$_2$SO$_4$ mobile phase at a flow rate of 0.4 mL/min. The column oven temperature is 65° C.

Residual glucose is measured with a bioanalyzer (Ysi Inc.) or by HPLC-refractometry with an Aminex HPX87-H column.

The carbon yield Y$_{p/s}$ is calculated in grams of succinate produced per gram of glucose consumed.

This yield increases significantly by 6% for the engineering strain EQ.EC046 compared with the control strain EQ.EC045 (empty).

TABLE 26

Composition of expression cassettes

| | | Structure of the synthetic operon | | | | | | |
|---|---|---|---|---|---|---|---|---|
| | | Block I | | | Block II | | Block III | |
| Plasmid | Vector type | CDS A | RBS1 | CDS B | RBS2 | CDS C | RBS3 | CDS D |
| pZA11 | pZA11 | | | | | | | |
| pEQEC006 | pZA11 | rbcS | D | rbcL | B | rbcX | F | prk |
| pZE21MCS | pZE21MCS | | | | | | | |
| pEQEC035 | pZE21MCS | FPGLOXDH1 | D | aceA | | | | |

To control the expression level of these genes, ribosome binding sequences (RBS) presented in Table 19 (Example 4B]), with variable translation efficiencies (Levin-Karp et al., ACS Synth Biol. 2013 Jun. 21; 2(6):327-36. doi: 10.1021/sb400002n; Zelcbuch et al., Nucleic Acids Res. 2013 May; 41(9):e98) are inserted between the coding phase for each gene. The succession of each coding phase interspersed by an RBS sequence is constructed by successive insertions into a pZA11 vector (Expressys) that contains a PLtetO-1 promoter, a p15A origin of replication and an ampicillin resistance gene.

Several strains are produced by electroporating the different vectors presented according to the plan below EQ.EC045→(EQ.EC042+pZA11+pZE21MCS): MG1655 ΔsdhA ΔaceB P$_{icd}$::P$_{oxb1}$ EQ.EC046→(EQ.EC045+pEQEC006+pEQEC035): MG1655 ΔsdhA ΔaceB P$_{icd}$::P$_{oxb1}$ Δzwf ΔgapA+(FPGLOXDH1+aceA)+(RuBisCO+PRK)

ii) Oxalate Determination

The pellets are washed twice with 10 mM potassium phosphate buffer (pH 7.5) containing 2 mM EDTA and stored at −20° C. Samples (1 mL) are transferred into a tube pre-cooled with 0.75 g of glass beads (425-600 μm) and introduced into a Fast Prep homogenizer (Thermo Scientific, Erembodegem, Netherlands) and subjected to 4 bursts of 20 s at speed control 6. The lysates are centrifuged for 20 min at 4° C. and 36,000 g. Total protein determinations are performed according to the Lowry method (Lowry et al., 1951). Oxaloacetate acetyl hydrolase (EC 3.7.1.1.1) activity is measured using a modification of the direct optical determination of oxaloacetate (OAA) at 255 nm as described in (Lenz et al., 1976). The disappearance of the OAA enol tautomer is checked at 255 nm at 25° C. in a Hitachi Model 100-60 spectrophotometer (Hitachi, Tokyo, Japan), using quartz cuvettes. The 1 mL reaction mixture contains 100 mM imidazole-HCl (pH 7.5), 0.9 mM MnCl$_2$·2H$_2$O, 1 mM OAA, 20 μL cell extract (controls with different volumes of cell extracts confirm the linear relationship between enzyme activity and the amount of cell extract). The reaction is started by adding the cell extract.

The carbon yield $Y_{p/s}$ is calculated in grams of doxalate produced per gram of glucose consumed.

This efficiency increases significantly by 3% for the engineering strain EQ.EC046 compared with the control strain EQ.EC045 (empty).

Example 8: Improvement of Citrate Production in *Aspergillus niger* a) Strategy

The inactivation of the pgkA gene (Locus tag An08g02260), leading to the non-functionality of the glycolysis pathway, and that of the gsdA gene (Locus tag An02g12140), inhibiting the oxidative part of the pentose phosphate pathway, are used to integrate the six genes for the functional expression of the PRK and RuBisCO enzymes, namely RbcS, RbcL, RbcX, GroES, GroEL and PRK for $CO_2$ fixation.

b) DNA Constructs i) Guide RNA Sequences for Targeting the Gene to be Inactivated In each of these two genes, a sequence of 20 nucleotides punctuated by an NGG motif (CRISPR target sequence underlined) was determined (Table 27). In both cases, this sequence is specific to the targeted gene but also unique in the *Aspergillus niger* genome. These sequences are used to express a guide RNA (gRNA) which, by forming a heteroduplex with the homologous region of the *Aspergillus niger* genome, directs the action of the CAS9 endonuclease to induce a double-stranded break specifically on the chosen locus.

TABLE 27 gRNA target sequence

| Locus | Gene | Reference genome | Locus tag | CRISPR sequences |
|---|---|---|---|---|
| 1 | pgkA | *A. niger* CBS 513-88 | An08g02260) | CAACAAGGCCACTGGT GGCCAGG (SEQ ID NO: 19) |
| 2 | gsdA | *A. niger* CBS 513-88 | An02g12140) | CATTTCCGGTCAATAT GACAAGG (SEQ ID NO: 20) |

Plasmid pFC332 (Addgene #87845) described in Sarkari et al. (Bioresour Technol. 2017 December; 245(Pt B):1327-1333) contains a gRNA expression cassette, a cassette allowing the functional expression of the Cas9 endonuclease and an Hph cassette allowing the selection of this plasmid. The plasmid also contains the fragment AMA1_2.8 which allows transient propagation of the plasmid. Finally, an origin of replication for *E. coli* is also present.

In order to target another gene, the gRNA cassette between FS A and FS B can be easily exchanged. This plasmid is modified by amplifying the different parts of this plasmid, in order to eliminate the antibiotic selection cassette and modify the 20 nucleotides allowing the specificity of gRNA in favor of the sequences described in Table 27 to form plasmids pEQ0610 to target pgkA and pEQ0611 to target gsdA.

Donor Plasmid
Regions of Homologies with the Genome

The donor plasmid consists of an In-Fusion® HD Cloning Kit User Manual—Clontech assembly between plasmid pUC19 (GenBank: M77789.2) and the genomic targeting sequences (LA and RA) of approximately 1500 bp each, homologous to the locus chosen for integration. The LA and RA sequences are adjacent at 5' and 3' respectively to the locus sequence targeted by the guide RNA. The genomic DNA/guide RNA heterodimer is recognized by the Cas9 endonuclease for double-stranded cleavage (locus 1: pgkA; locus 2: gsdA) (Table 28). The RA and LA fragments are amplified with primers for the pgkA gene and the gsdA gene (Table 29). The amplicon sequences are given in the sequence listing (SEQ ID NO: 55 to SEQ ID NO: 58). An extension of 18 nucleotides on all forward primers of the three fragments is added according to the protocol of the In-Fusion® HD Cloning Kit User Manual—Clontech, to allow a functional assembly of the plasmids (pEQ0600 or pEQ0601) and the introduction of two restriction sites for type II restriction endonucleases (restriction enzymes I-Ceul and I-Sce)I which have large asymmetric recognition sites (12 to 40 base pairs). These are recognition sequences of 18 base pairs, so rare. The fact that the cleavage is asymmetric at the reconnaissance site allows the release of a fragment lacking sequences from bacterial vector pUC19. These two enzymes allow the integration block to be extracted by restriction after amplification by cloning in *E. coli*.

TABLE 28

Amplification of regions of homologies for the pgkA gene

| Amplicon | Alias | Primer position | Primer sequence |
|---|---|---|---|
| 5'pgkA_*A. niger* | LA1 | Forward | GGATCGCAGATACGGTCG C (SEQ ID NO: 21) |
| | | Reverse | CCTCGGTGAAGCAACGC TG (SEQ ID NO: 22) |
| 3'pgkA_*A. niger* | RA1 | Forward | CTCCTTGAGAACCTGCGT TTCC (SEQ ID NO: 23) |
| | | Reverse | CTGAAGTACGTTTTCCCA AGCC (SEQ ID NO: 24) |

TABLE 29

Amplification of regions of homologies for the gsdA gene

| Amplicon | Alias | Primer position | Primer sequence |
|---|---|---|---|
| 5'gsdA_*A. niger* | LA2 | Forward | CGTTATCACAAAGAAGCC AGGTCC (SEQ ID NO: 25) |
| | | Reverse | GCTGCTCTTCGATTTCCT TGGT (SEQ ID NO: 26) |
| 3'gsdA_*A. niger* | RA2 | Forward | TCATCAACCTCAACAAGC ACCTC (SEQ ID NO: 27) |
| | | Reverse | GTGAAGACAGCGGCGGTC C (SEQ ID NO: 28) |

Engineering Expression Cassettes

The promoters and terminators are identified on the basis of GenBank data. The selected promoters are determined from the +1 transcription point and go up 1.4 kb upstream in order to cover both the "core" sequences (TATA box) and the trans-activating sequences allowing the optimal functionality of the promoter concerned.

For the terminators, the cut-off is made 500 bp after the stop codon of the gene.

The structure of each integration block of four expression cassettes is defined as follows: the first level consists of simple elements, namely promoters, coding sequences (CDS) and terminators. The promoter (Table 30) and terminator (Table 31) elements, whose sequences are provided in the sequence listing (SEQ ID NO: 59 to 62), are amplified and assembled with the engineering CDS according to Table 32. The CDS, whose sequences are provided in the sequence listing (SEQ ID NO: 63 to 66), are amplified according to the protocol provided with the NEBuilder® HiFi DNA Assembly Master Mix Kit (E2321) to obtain the functional expression cassettes compiled in the table. Each integration block of four genes is organized to include four different pairs (promoter/terminator) in order to limit trans interference. Each integration block of six genes is organized to include six different pairs (promoter/terminator) in order to limit transcriptional interference Donor Fragment for Insertion into the Target Locus of the Genome The different multiple expression cassettes (RbcS, RbcL and RbcX) or (GroES, GroEL and PRK) are amplified and assembled around an antibiotic selection cassette (Table), according to the protocol of the In-Fusion® HD Cloning Kit User Manual—Clontech, to form donor plasmids (pEQ0602 or pEQ0603).

TABLE 30

Native location of *Aspergillus niger* promoters used in genomic combinatorics to insert the six genes of the $CO_2$ fixation engineering into the *Aspergillus niger* genome.

| Promoters | Organism | Gene ID | Reverse primer | Forward primer |
|---|---|---|---|---|
| PmbfA | A. niger CBS 513-88 | An02g12390 | TTTGAAGATGGATGAGAAGTCGG (SEQ ID NO: 33) | GCCATGAAATCCAATCATTTCC (SEQ ID NO: 29) |
| PcoxA | A. niger CBS 513-88 | An07g07390 | FGTCCTGGTGGGTGGGTTG (SEQ ID NO: 34) | GACGGCATTTGAGCAACATC (SEQ ID NO: 30) |
| PsrpB | A. niger CBS 513-88 | An16g08910 | CTCGAACGAGAATGGGAACC (SEQ ID NO: 35) | TTGGCAGGGTCACGTAGCC (SEQ ID NO: 31) |
| PtvdA | A. niger CBS 513-88 | An04g01530 | GGCGGAATGAGATGCGACAG (SEQ ID NO: 36) | TTAGTCCATTCAGCAAGCTGCC (SEQ ID NO: 32) |

TABLE 31

Native location of *Aspergillus Niger* terminators used in genomic combinatorics to insert the six genes of the $CO_2$ fixation engineering into the *Aspergillus niger* genome.

| Terminators | Organism | Gene ID | Forward primer | Reverse primer |
|---|---|---|---|---|
| TtrpC | A. nidulans FGSC A4 | AN0648 | TGATTTAATAGCTCCATGTCAAC AAG (SEQ ID NO: 37) | GGGTAAACGACTCATAGGAGAGTTG (SEQ ID NO: 41) |
| TniaD | A. nidulans FGSC A4 | AN1006 | ACGGGTTCGCATAGGTTTGG (SEQ ID NO: 38) | GGGATATTTGACACGATTCTGAGG (SEQ ID NO: 42) |
| TglaA | A. niger CBS 513-88 | An03g06550 | CGACCGCGACGGTGACTGAC (SEQ ID NO: 39) | CCGGAGATCCTGATCATCCG (SEQ ID NO: 43) |
| TgpdA | A. niger CBS 513-88 | An16g01830 | GAATCAGGACGGCAAACTGAAT (SEQ ID NO: 40) | CGTGGTCTAGCTGCCCTCC (SEQ ID NO: 44) |

TABLE 32

Assembly of expression cassettes

| Expression cassette | Gene | GenBank | Codon optimization | Promoter | Terminator |
|---|---|---|---|---|---|
| CAS 1 | RbcL | BAD78320.1 | Yes | PmbfA$_p$ | trpct |
| CAS 2 | RbcS | BAD78319.1 | Yes | PcoxA$_p$ | TniaD |
| CAS 3 | RbcX | BAD80711.1 | Yes | PsrpB$_p$ | glaAt |

TABLE 32-continued

Assembly of expression cassettes

| Expression cassette | Gene | GenBank | Codon optimization | Promoter | Terminator |
|---|---|---|---|---|---|
| CAS 4 | Hph | pUG75(P30671) | No | $picdA_p$ | TgpdA |
| CAS 5 | GroES | U00096 | No | $PmbfA_p$ | trpct |
| CAS 6 | GroEL | AP009048 | No | $PcoxA_p$ | TniaD |
| CAS 7 | PRK | BAD78757.1 | Yes | $PsrpB_p$ | glaAt |
| CAS 8 | Ble | pUG66(P30116) | No | $picdA_p$ | TgpdA |

TABLE 33

Plasmid assembly

| Plasmid | Genomic sequence | Promoter | Gene | Terminator | Genomic sequence | ori | Selection marker |
|---|---|---|---|---|---|---|---|
| pEQ0600 | LA1 | | | | RA1 | coli | Ampicillin |
| pEQ0601 | LA2 | | | | RA2 | coli | Ampicillin |
| pEQ0602 | LA2 | $PmbfA_p$ | RbcL | trpct | RA2 | coli | Ampicillin and |
|  |  | $PcoxA_p$ | RbcS | TniaD |  | coli | hydromycin B |
|  |  | $PsrpB_p$ | RbcX | glaAt |  | coli |  |
|  |  | $picdA_p$ | Hph | TgpdA |  | coli |  |
| pEQ0603 | LA1 | $PmbfA_p$ | GroES | Trpct | RA1 | coli | Ampicillin and |
|  |  | PcoxAp | GroEL | TniaD |  | coli | bleomycin |
|  |  | PsrpBp | PRK | glaAt |  | coli |  |
|  |  | picdAp | Blue | TgpdA |  | coli |  | c) Transformation of *Aspergillus niger*

The transformation of DNA in *Aspergillus niger* is constrained by the presence of the fungal cell wall, and is extremely ineffective compared with yeast or *Escherichia coli*. Nevertheless, the transformation of protoplasts prepared from fungal hyphae or conidiospores to germination by treatment with cell wall degrading enzymes such as the cocktail consisting of Lysing Enzyme® from *Trichoderma harzianum*, chitinase from *Streptomyces griseus* and ß-glucuronidase from *Helix pomatia* (de Bekker et al., J Microbiol Methods. 2009 March; 76(3):305-6) allows transformants to be produced.

The *A. niger* strain CBS 513-88 is grown at 30° C. in a 1 L Erlenmeyer flask with 250 mL of transformation medium (Kusters-van Someren et al., Curr Genet. 1991 September; 20(4):293-9). After growth for 16 h at 250 rpm, the mycelium is collected by filtration on Miracloth (Calbiochem) and washed with deionized water. Protoplasts are prepared in the presence of 5 g/L lysis enzymes from *Trichoderma harzianum* (Sigma Saint Louis, MO, USA), 0.075 Uml-1 chitinase from *Streptomyces griseus* (Sigma) and 460 Uml-1 glucuronidase from *Helix pomatia* (Sigma) in KMC (0.7 M KCl, 50 mM $CaCl_2$), 20 mM Mes/NaOH, pH 5.8) for 2 hours at 37° C. and 120 rpm. Protoplasting is monitored every 30 minutes with a microscope. The protoplasts are filtered through a Miracloth filter and collected by centrifugation at 2000×g and 4° C. for 10 minutes. The protoplasts are washed with cold STC (1.2 M sorbitol, 10 mM Tris/HCl, 50 mM $CaCl_2$, pH 7.5) and then resuspended in 100 pi of STC and used directly for the transformation.

In order to integrate a metabolic pathway into the *A. niger* genome, co-transformation of a plasmid and a linear fragment is required. Plasmid pEQ0610 is co-transformed with a donor fragment to integrate part of the engineering into the genome while inactivating the pgkA gene. Similarly, plasmid pEQ0611 is co-transformed with a donor fragment to integrate the other part of the engineering into the genome while inactivating the gsdA gene. These sequences serve both as matrices for homologous recombination and as selection markers: during integration with functional expression of the antibiotic resistance genes Hph or Ble. The strains are directly selected on minimal medium plates with an addition of hygromycin B or bleomycin allowing direct selection on the integration event. Due to the presence of the origin of replication AMA1_2.8, plasmid pCAS_pyrG2 is easily lost causing only transient expression of the Cas9 protein, thus reducing the risk of non-targeted adverse effects.

Linear cassettes (10 µg) and plasmid (5 µg) are mixed with 100 µL of STC solution containing at least 107 protoplasts and 330 µL of freshly prepared polyethylene glycol (PEG) solution (25% PEG 6000, 50 mM $CaCl_2$), 10 mM Tris/HCl, pH 7.5) and kept on ice for 20 minutes. After mixing with an additional 2 mL PEG solution and incubating at room temperature for 10 minutes, the protoplast mixture is diluted with 4 mL of STC.

The selection of transformants is carried out on MM plates with 150 µg/ml hygromycin B added or MM plates with 50 µg/mL bleomycin added. All transformants are purified by isolating single colonies from the selection medium at least twice. The insertion of the fragments is verified by sequencing the target locus with the appropriate control primers.

Genomic DNA from fungal cells is isolated with a modified protocol, using the Wizard® Genomic DNA Purification Kit (Promega, Wisconsin, USA). The mycelium is cultured overnight in CM (30° C., 150 rpm) in 290 µl of 50 mM EDTA solution and 10 pi of lyticase (10 mg/mL) to remove the cell wall. After 90 minutes of incubation at 37° ° C., the suspension is centrifuged and the supernatant is discarded. The mycelium pellet is resuspended in 300 µL of nuclei lysis solution and 100 µL of protein precipitation solution. The samples are incubated on ice for 5 minutes and centrifuged. The DNA is precipitated with isopropanol and washed with 70% ethanol. The DNA pellet is rehydrated with a DNA rehydration solution containing RNase (100 μg/mL). The successful transformation and integration of the expression cassettes was verified by PCR.

TABLE 34

Strains used for the yield study

| Strains | Genome | Genetic modification |
|---|---|---|
| EQ1500 | A. niger CBS 513-88 | |
| EQ1501 | A. niger CBS 513-88 | gsdA :: PmbfA$_p$-RbcL-trpc; PcoxA$_p$-RbcS-TniaD; picdA$_p$-Hph-TgpdA; PsrpB$_p$-RbcX-glaAt |
| EQ1502 | A. niger CBS 513-88 | gsdA :: PmbfA$_p$-RbcL-trpc; PcoxA$_p$-RbcS-TniaD; picdAp-Hph-TgpdA; PsrpB$_p$-RbcX-glaAt pgkA:: PmbfA$_p$-GrES-trpc; PcoxA$_p$-GroEL-TniaD; picdA$_p$-Ble-TgpdA; PsrpB$_p$-PRK-glaAt |

Conidia (108/L) from strains EQ1500 and EQ1502 are inoculated and cultured at 30° C. on a rotary shaker (180 rpm) in shaker flasks containing Vogel medium without MnSO$_4$ with a total glucose content of 15% and a total nitrogen content of 0.2% and 10% CO$_2$. The determination of glucose and organic acids was performed as described above (Blumhoff et al., 2013; Steiger et al., 2016) on an HPLC (Shimadzu, Kyoto; Japan) equipped with an Aminex HPX-87 H column (300×7.8 mm, Bio-Rad, Hercules, CA). A refractive index detector (RID-10 A, Shimadzu) is used for the detection of glucose and citric acid, while a PDA detector (SPD-M20A, Shimadzu) at 300 nm is used to detect cis-aconitic and trans-aconitic acid. The column is used at 60° C. at a flow rate of 0.6 mL/min and with a 0.004 M H$_2$SO$_4$ aqueous solution as mobile phase. The culture was carried out in three biological replicates.

d) Analytical Method

For the quantification of extracellular metabolites, a culture sample is centrifuged at 14,000×g for 5 min. The supernatant is filtered through a filter with a 0.45 pm pore size. The filtrate is maintained at −20° C. until analysis. The concentration of citrate and of oxalate is detected and quantified with ultraviolet light at 210 nm using an Amethyst C18-H column (250×4.6 mm, Sepax Technologies, Newark, DE, USA). Elution is carried out at 30° C. with 0.03% H$_3$PO$_4$ at a flow rate of 0.8 mL/min. Reducing sugar is detected with the 3,5-dinitrosalicylic acid method. Biomass determination: 5 mL of sample is filtered through Miracloth (Calbiochem, San Diego, CA, USA) to collect hyphae and washed with distilled water. The hyphae are heated to 105° C. in a "Miracloth". For the calculation of the dry cell weight (DCW), the weight of Miracloth is measured beforehand and subtracted from the total weight to give the net weight, then the net weight per unit volume is calculated as DCW.

After complete analysis, the comparison of citric acid production yield as a function of glucose consumption is 18% higher in the engineered strain EQ1502 than in the wild-type strain EQ1500.

Example 9: Improvement of Itaconate Production in Aspergillus terreus a) Strategy Inactivation of the pgkA gene (Locus tag (ATEG_00224), leading to the non-functionality of the glycolysis pathway, and that of the gsdA gene (Locus tag ATEG_01623), inhibiting the oxidative part of the phosphate pentose pathway, are used to integrate the six genes allowing the functional expression of the PRK and RuBisCO enzymes, namely rbcS, rbcL, rbcX, groES, groEL and prk allowing CO$_2$ fixation.

b) DNA Constructs i) RNA Guide Sequences to Target the Gene to be Inactivated

In each of these two genes, a sequence of 20 nucleotides punctuated by an NGG motif (CRISPR target sequence underlined) was determined (Table 35). In both cases, this sequence is specific to the targeted gene but also unique in the Aspergillus terreus genome. These sequences are used to express a guide RNA (gRNA) which, by forming a heteroduplex with the homologous region of the Aspergillus terreus genome, directs the action of the CAS9 endonuclesae to induce a double-stranded break specifically on the selected locus. For pgkA, the sequence identified in the second intron, the first 20 nucleotides have a unique pattern in the genome, even allowing two mismatches. For gsdA, the sequence identified in the fourth intron, the first 20 nucleotides have a unique pattern in the genome, even allowing two mismatches.

TABLE 35

Guide RNA target sequence

| Locus | Gene | Reference genome | Locus tag | CRISPR sequences |
|---|---|---|---|---|
| 3 | pgkA | A. terreus NIH262 | (ATEG 00224) | CTGCGTCGGCAAGGAAGTT GAGG (SEQ ID NO: 45) |
| 4 | gsdA | A. terreus NIH2624 | (ATEG 01623) | CATCAGCGGCCAATATGAC AAGG (SEQ ID NO: 46) |

Plasmid pFC332 (Addgene #87845) described in Sakari et al. (Bioresour technol. 2017; 245(Pt B):1327-1333) contains a gRNA expression cassette, a cassette for the functional expression of the Cas9 endonuclease and an Hph cassette for the selection of this plasmid. The plasmid also contains the fragment AMA1_2.8 which allows transient propagation of the plasmid. Finally, an origin of replication for E. coli is also present.

In order to target another gene, the gRNA cassette between FS A and FS B can be easily exchanged. Thus, this plasmid is modified by amplifying the different parts of this plasmid in order to eliminate the antibiotic selection cassette and to modify the 20 nucleotides allowing the specificity of gRNA in favor of the sequences described in Table 35 to form plasmids pEQ0615 to target pgkA and pEQ0616 to target gsdA in the Aspergillus terreus genome.

ii) Donor Plasmid

Regions of Homology with the Genome

The donor plasmid consists of an In-Fusion® HD Cloning Kit User Manual—Clontech assembly between plasmid pUC19 (GenBank: M77789.2) and genomic targeting sequences (LA and RA) of approximately 1500 bp each homologous to the locus chosen for integration. The LA and RA sequences are adjacent at 5' and 3' respectively to the locus sequence targeted by the guide RNA. The genomic DNA/guide RNA heterodimer is recognized by the Cas9 endonuclease for double-stranded cleavage (locus 1: pgkA; locus 2: gsdA) (Table 35). The RA and LA fragments are amplified with the primers described in Table 36, for the pgkA gene, and Table 37, for the gsdA gene. The amplicon sequences are in the sequence listing (SEQ ID NO: 67 to 70).

An extension of 18 nucleotides on all forward primers of the three fragments is added according to the protocol of the In-Fusion® HD Cloning Kit User Manual—Clontech to allow a functional assembly of the plasmids (pEQ0604 or pEQ0605) (33) and the introduction of two restriction sites for type II restriction endonucleases (restriction enzymes I-CeuI and I-SceI) which have large asymmetric recognition sites (12 to 40 base pairs). These are recognition sequences of 18 base pairs, therefore rare and not present in the described assembly. The fact that the cleavage is asymmetric at the reconnaissance site allows a fragment devoid of sequences to be released from the bacterial vector pUC19. These two enzymes allow the integration block to be extracted by restriction after amplification by cloning in E. coli.

TABLE 36

Amplification of regions of homologies for the pgkA gene

| Amplicon | Primer position | Primer sequence |
|---|---|---|
| 5'pgkA_Aterreus | Forward | CTTGGGGAATTGGGACACG (SEQ ID NO: 47) |
| | Reverse | TCTTGCCGATGAGCTTCTCC (SEQ ID NO: 48) |
| 3'pgkA_Aterreus | Forward | CAGATCATCCTCCTGGAGAACC (SEQ ID NO: 49) |
| | Reverse | ACGGCACGAATGTTCACCTG (SEQ ID NO: 50) |

TABLE 37

Amplification of regions of homologies for the gsdA gene

| Amplicon | Primer position | Primer sequence |
|---|---|---|
| 5'gsdA_Aterreus | Forward | ATTGGAAGCTGGCTCTATCTCACC (SEQ ID NO: 51) |
| | Reverse | GCTGTTCTTCGATTTCCTTGGTG (SEQ ID NO: 52) |
| 3'gsdA_Aterreus | Forward | TCAACCTCACCAAGCACCTCG (SEQ ID NO: 53) |
| | Reverse | CAAACAGCCCGTCGCAACTG (SEQ ID NO: 54) |

Engineering Expression Cassettes

Promoters and terminators are identified on the basis of GenBank data. The selected promoters are determined from the +1 transcription point and go up 1.4 kb upstream in order to cover both the "core" sequences (TATA box) and the trans-activating sequences allowing the optimal functionality of the promoter concerned.

For the terminators, the cut-off is made 500 bp after the stop codon of the gene.

The structure of each integration block of four expression cassettes is defined as follows: the first level consists of simple elements, namely promoters, coding sequences (CDS) and terminators. The promoter (Table 30) and terminator Table 31) elements are amplified and assembled with the engineering CDS according to Table 32. The CDS are amplified according to the protocol provided with the NEBuilder® HiFi DNA Assembly Master Mix Kit (E2321) in order to obtain the functional expression cassettes compiled in the table. Each integration block of four genes is organized to include four different terminator promoter pairs in order to limit trans interference Each integration block of six genes is organized to include six different terminator promoter pairs in order to limit transcriptional interference.

Donor Fragment for Insertion into the Target Locus of the Genome

The different multiple expression cassettes (RbcS, RbcL and RbcX or GroES, GroEL and PRK are amplified and assembled around an antibiotic selection cassette (Table 38), according to the protocol of the In-Fusion® HD Cloning Kit User Manual—Clontech, to form donor plasmids (pEQ0606 or pEQ0607).

TABLE 38

Plasmid assembly

| Plasmids | Genomic sequence | Promoter | Gene | Terminator | Genomic sequence | ori | Selection marker |
|---|---|---|---|---|---|---|---|
| pEQ0604 | LA4 | | | | RA4 | coli | Ampicillin |
| pEQ0605 | LA3 | | | | RA3 | coli | Ampicillin |
| pEQ0606 | LA4 | PmbfA$_p$ | rbcL | trpct | RA4 | coli | Ampicillin and |
| | | PcoxA$_p$ | rbcS | TniaD | | coli | hydromycin B |
| | | PsrpB$_p$ | rbcX | glaAt | | coli | |
| | | picdA$_p$ | Hph | TgpdA | | coli | |
| pEQ0607 | LA3 | PmbfA$_p$ | groES | trpct | RA3 | coli | Ampicillin and |
| | | PcoxA$_p$ | groEL | TniaD | | coli | bleomycin |
| | | PsrpB$_p$ | prk | glaAt | | coli | |
| | | picdA$_p$ | Ble | TgpdA | | coli | | c) Transformation of *Aspergillus terreus*

The transformation of *Aspergillus terreus* DNA is carried out in accordance with the strategy applied for *Aspergillus niger* (Example 8) using *A. terreus* strain NIH262.

TABLE 39

Strains used for the yield study

| Strains | Genome | Genetic modification |
|---|---|---|
| EQ1600 | A. terreus NIH262 | |
| EQ1601 | A. terreus NIH262 | gsdA:: PmbfA$_p$-RbcL-trpc; PcoxA$_p$-RbcS-TniaD; picdA$_p$-Hph-TgpdA; PsrpB$_p$-RbcX-glaAt |
| EQ1602 | A. terreus NIH262 | gsdA:: PmbfA$_p$-RbcL-trpc; PcoxA$_p$-RbcS-TniaD; picdAp-Hph-TgpdA; PsrpB$_p$-RbcX-glaAt pgkA:: PmbfA$_p$-GrES-trpc; PcoxA$_p$-GroEL-TniaD; picdA$_p$-Ble-TgpdA; PsrpB$_p$-PRK-glaAt |

Culture of *A. terreus* strains EQ1600 and EQ1602 on 3% glucose.

The optimized media composition described by Hevekerl et al. (Appl Microbiol Biotechnol. 2014; 98:6983-6989) is used. It contains 0.8 g $KH_2PO_4$, 3 g $NH_4NO_3$, 1 g $MgSO_4 \cdot 7H_2O$, 5 g $CaCl_2)_2 \cdot 2 H_2O$, 1.67 mg $FeCl_3 \cdot 6H_2O$, 8 mg $ZnSO_4 \cdot 7H_2O$ and 15 mg $CuSO_4 \cdot 7H_2O$ per liter. To mimic the typical sugar concentration obtained from wheat straw hydrolysate (150 g/L) pretreated with dilute acid (0.75% v/v, 160° ° C., 10 min) and enzymatically saccharified (pH 5.0, 45° C., 72 h), an adequate amount of glucose up to 30 g/L is used. Sugars and all other components are added from sterile stock solutions. The pH of the medium without $CaCl_2$) is adjusted to 3.1 with 0.5 M $H_2SO_4$ before inoculating the spore preparation for strains EQ1600 and EQ1602. The culture is carried out under shaking with 25 mL of medium in 125 mL Erlenmeyer flasks at 33° C. in a rotary shaker at 200 rpm for 7-10 days in an environment of 10% $CO_2$. The pH is not checked during fermentation. Shaking of the flasks is maintained during sampling for time studies to ensure a continuous supply of oxygen. All experiments are carried out in triplicate. All media components are obtained from Sigma Chemical, St. Louis, Missouri. For these experiments, each sugar was dissolved in deionized water and passed through a column (440×45 mm) of Dowex 50-X8 (100/200 mesh) cation-exchange resin (Bio-Rad Laboratories, Hercules, CA) to remove manganese, if necessary.

d) Analytical Procedures

The concentration of the cell mass is determined from the dry cell weight. The cell mass present in the fermentation broth is collected by centrifugation at 10,000 g for 10 minutes and carefully rinsed three times with deionized water. The rinsed cell mass was completely dried at 80° C. until a constant weight was obtained. The fermentation broth after centrifugation (10,000 g, 10 min) is stored at −20° C. before analysis of glucose, itaconic acid and by-products (succinic acid, α-ketoglutaric acid, malic acid, cis-aconitic acid, and trans-aconitic acid) using high-performance liquid chromatography (HPLC). A Shimadzu Prominence HPLC system (Shimadzu America, Inc., Columbia, MD) is used. Two columns (Aminex HPX-87P column, 300×7.8 mm with ash removal cartridge and Carbo-P protection cartridge, and one Aminex HPX 87H column, 300×7.8 mm with Microguard Cation H cartridge (Bio-Rad)) are used for the analysis of sugars and organic acids, respectively. The Aminex HPX 87P column is maintained at 85° C. and glucose is eluted with Milli-Q acidified deionized water (Millipore, Bedford, MA) at a flow rate of 0.6 mL/min.

The Aminex HPX 87H column is maintained at 65° C. and sugars and organic acids are eluted with 5 mM $H_2SO_4$ prepared using Milli-Q deionized filtered water at a rate of 0.5 mL/min. Detection is carried out using a refractive index detector for sugars and a 210 nm UV detector for organic acids. Propionic acid (1%, weight/volume) is used as internal standard to estimate the liquid lost during aerobic fermentation for 7-10 days at 33° C. under 10% $CO_2$. All HPLC standards, including organic acids, are purchased from Sigma. The manganese concentration (ppb level) is determined using an Optima 7000DV (Perkin-Elmer, Waltham, MA) inductively coupled plasma optical emission spectrometer (ICP-OES) by the procedure described by Bakota et al. (Eur J Lipid Sci Technol. 2015; 117:1452-1462.

Based on the results of the production of itaconic acid from glucose, a mass yield increment of itaconic acid from glucose of 15% is observed for the engineered strain EQ1602 compared with the reference strain EQ1600.

The invention claimed is:

1. Genetically modified microorganism expressing a functional RuBisCO enzyme and a functional phosphoribulokinase (PRK), and in which glycolysis pathway is inhibited by inhibiting the expression of a gene encoding glyceraldehyde 3-phosphate dehydrogenase and/or a gene encoding phosphoglycerate kinase, and oxidative branch of pentose phosphate pathway of said microorganism is also inhibited by inhibiting the expression of a gene encoding glucose-6-phosphate dehydrogenase or 6-phosphogluconolactonase or 6-phosphogluconate dehydrogenase, said microorganism being genetically modified so as to produce an exogenous molecule of interest and/or to overproduce an endogenous molecule of interest, other than the RuBisCO or phosphoribulokinase enzyme.

2. The genetically modified microorganism of to claim 1, said microorganism being genetically modified to express a recombinant RuBisCO enzyme and/or PRK.

3. The genetically modified microorganism of to claim 1, said microorganism being genetically modified to inhibit the oxidative branch of the pentose phosphate pathway upstream of ribulose-5-phosphate production.

4. The genetically modified microorganism of to claim 1, wherein the exogenous molecule and/or the endogenous molecule is selected from the group consisting of amino acids, peptides, proteins, vitamins, sterols, flavonoids, terpenes, terpenoids, fatty acids, polyols and organic acids.

5. The genetically modified microorganism of claim 1, said microorganism being a eukaryotic cell selected from yeasts, fungi, microalgae, and a prokaryotic cell.

6. The genetically modified microorganism of claim 1, said microorganism being a yeast of the genus *Saccharomyces cerevisiae* genetically modified to express a functional type I or II RuBisCO and a functional phosphoribulokinase (PRK), and in which the expression of the TDH1, TDH2 and/or TDH3 gene is inhibited.

7. The genetically modified microorganism of claim 1, said microorganism being a *Saccharomyces cerevisiae* yeast genetically modified to express a functional type I or II RuBisCO and a functional phosphoribulokinase (PRK), and in which the expression of the PGK1 gene is inhibited.

8. The genetically modified microorganism of claim 6, wherein the expression of the ZWF1 gene is inhibited.

9. The genetically modified microorganism of claim 1, said microorganism being a filamentous fungus of the genus *Aspergillus* genetically modified to express a functional type I or II RuBisCO and a functional phosphoribulokinase (PRK), and in which the expression of the pgk and gsdA genes is inhibited.

10. The genetically modified microorganism of claim 1, said microorganism being an *E. coli* bacterium genetically modified to express a functional type I or II RuBisCO and a functional phosphoribulokinase (PRK), and in which the expression of the gapA and/or pgk gene is inhibited.

11. A process for producing an amino acid, peptide, protein, vitamin, sterol, flavonoid, terpene, terpenoid, fatty acid, polyol or organic acid comprising (i) inserting at least one sequence encoding an enzyme involved in the synthesis or bioconversion of said amino acid, peptide, protein, vitamin, sterol, flavonoid, terpene, terpenoid, fatty acid, polyol or organic acid into the genetically modified microorganism of claim 1, (ii) culturing said microorganism under conditions allowing expression of said enzyme and optionally (iii) recovering and/or purifying said amino acid, peptide, protein, vitamin, sterol, flavonoid, terpene, terpenoid, fatty acid, polyol or organic acid.

* * * * *

SEQUENCE LISTING

<160> NUMBER OF SEQ ID NOS: 71

<210> SEQ ID NO 1
<211> LENGTH: 76
<212> TYPE: DNA
<213> ORGANISM: artificial sequence
<220> FEATURE:
<223> OTHER INFORMATION: oligonucleotide CB101 (forward)

<400> SEQUENCE: 1
acagatcatc aaggaagtaa ttatctactt tttacaacaa atataaaaca atgggtaagg    60
aaaagactca cgtttc                                                   76

<210> SEQ ID NO 2
<211> LENGTH: 81
<212> TYPE: DNA
<213> ORGANISM: artificial sequence
<220> FEATURE:
<223> OTHER INFORMATION: oligonucleotide CB102 (reverse)

<400> SEQUENCE: 2
gggaaagaga aaagaaaaaa attgatctat cgatttcaat tcaattcaat ttagaaaaac    60
tcatcgagca tcaaatgaaa c                                             81

<210> SEQ ID NO 3
<211> LENGTH: 65
<212> TYPE: DNA
<213> ORGANISM: artificial sequence
<220> FEATURE:
<223> OTHER INFORMATION: oligonucleotide Sdzwf1

```
<400> SEQUENCE: 3
aagagtaaat ccaatagaat agaaaaccac ataaggcaag atgggtaaaa agcctgaact      60
caccg                                                                 65

<210> SEQ ID NO 4
<211> LENGTH: 63
<212> TYPE: DNA
<213> ORGANISM: artificial sequence
<220> FEATURE:
<223> OTHER INFORMATION: oligonucleotide Rdzwf1

<400> SEQUENCE: 4
atttcagtga cttagccgat aaatgaatgt gcttgcattt ttttattcct ttgccctcgg      60
acg                                                                   63

<210> SEQ ID NO 5
<211> LENGTH: 76
<212> TYPE: DNA
<213> ORGANISM: artificial sequence
<220> FEATURE:
<223> OTHER INFORMATION: oligonucleotide Sdpgk1

<400> SEQUENCE: 5
acagatcatc aaggaagtaa ttatctactt tttacaacaa atataaaaca atgggtaagg      60
aaaagactca cgtttc                                                     76

<210> SEQ ID NO 6
<211> LENGTH: 81
<212> TYPE: DNA
<213> ORGANISM: artificial sequence
<220> FEATURE:
<223> OTHER INFORMATION: oligonucleotide Rdpgk1

<400> SEQUENCE: 6
gggaaagaga aaagaaaaaa attgatctat cgatttcaat tcaattcaat ttagaaaaac      60
tcatcgagca tcaaatgaaa c                                               81

<210> SEQ ID NO 7
<211> LENGTH: 75
<212> TYPE: DNA
<213> ORGANISM: artificial sequence
<220> FEATURE:
<223> OTHER INFORMATION: oligonucleotide Sdidh1

<400> SEQUENCE: 7
tctccctatc ctcattcttc tcccttttcc tccataattg taagagaaaa atgggtacca      60
ctcttgacga cacgg                                                      75

<210> SEQ ID NO 8
<211> LENGTH: 78
<212> TYPE: DNA
<213> ORGANISM: artificial sequence
<220> FEATURE:
<223> OTHER INFORMATION: Oligonucleotide Rdidh1

<400> SEQUENCE: 8
aatttgaaca cacttaagtt gcagaacaaa aaaaggggga attgttttca ttaggggcag      60
ggcatgctca tgtagagc                                                   78

<210> SEQ ID NO 9
<211> LENGTH: 12
```

```
<212> TYPE: DNA
<213> ORGANISM: artificial sequence
<220> FEATURE:
<223> OTHER INFORMATION: ribosome binding sequence

<400> SEQUENCE: 9
aggaggtttg ga                                                               12

<210> SEQ ID NO 10
<211> LENGTH: 22
<212> TYPE: DNA
<213> ORGANISM: artificial sequence
<220> FEATURE:
<223> OTHER INFORMATION: ribosome binding sequence

<400> SEQUENCE: 10
aacaaaatga ggaggtactg ag                                                    22

<210> SEQ ID NO 11
<211> LENGTH: 16
<212> TYPE: DNA
<213> ORGANISM: artificial sequence
<220> FEATURE:
<223> OTHER INFORMATION: ribosome binding sequence

<400> SEQUENCE: 11
aagttaagag gcaaga                                                           16

<210> SEQ ID NO 12
<211> LENGTH: 14
<212> TYPE: DNA
<213> ORGANISM: artificial sequence
<220> FEATURE:
<223> OTHER INFORMATION: ribosome binding sequence

<400> SEQUENCE: 12
ttcgcagggg gaag                                                             14

<210> SEQ ID NO 13
<211> LENGTH: 18
<212> TYPE: DNA
<213> ORGANISM: artificial sequence
<220> FEATURE:
<223> OTHER INFORMATION: ribosome binding sequence

<400> SEQUENCE: 13
taagcaggac cggcggcg                                                         18

<210> SEQ ID NO 14
<211> LENGTH: 12
<212> TYPE: DNA
<213> ORGANISM: artificial sequence
<220> FEATURE:
<223> OTHER INFORMATION: ribosome binding sequence

<400> SEQUENCE: 14
caccatacac tg                                                               12

<210> SEQ ID NO 15
<211> LENGTH: 18
<212> TYPE: DNA
<213> ORGANISM: artificial sequence
<220> FEATURE:
<223> OTHER INFORMATION: oligonucleotide POXB1-S

<400> SEQUENCE: 15
```

-continued tcgttgcgtt acacacac                                                 18

<210> SEQ ID NO 16
<211> LENGTH: 19
<212> TYPE: DNA
<213> ORGANISM: artificial sequence
<220> FEATURE:
<223> OTHER INFORMATION: oligonucleotide POXB1-R

<400> SEQUENCE: 16
tgtgtcgagt ggatggtag                                                19

<210> SEQ ID NO 17
<211> LENGTH: 11
<212> TYPE: DNA
<213> ORGANISM: artificial sequence
<220> FEATURE:
<223> OTHER INFORMATION: oligonucleotide Spacer S

<400> SEQUENCE: 17
gcatgaattc g                                                        11

<210> SEQ ID NO 18
<211> LENGTH: 11
<212> TYPE: DNA
<213> ORGANISM: artificial sequence
<220> FEATURE:
<223> OTHER INFORMATION: oligonucleotide Spacer R

<400> SEQUENCE: 18
cgaattcatg c                                                        11

<210> SEQ ID NO 19
<211> LENGTH: 23
<212> TYPE: DNA
<213> ORGANISM: artificial sequence
<220> FEATURE:
<223> OTHER INFORMATION: gRNA target sequence for CRISPR pgkA

<400> SEQUENCE: 19
caacaaggcc actggtggcc agg                                           23

<210> SEQ ID NO 20
<211> LENGTH: 23
<212> TYPE: DNA
<213> ORGANISM: artificial sequence
<220> FEATURE:
<223> OTHER INFORMATION: gRNA target sequence for CRISPR gsdA

<400> SEQUENCE: 20
catttccggt caatatgaca agg                                           23

<210> SEQ ID NO 21
<211> LENGTH: 19
<212> TYPE: DNA
<213> ORGANISM: artificial sequence
<220> FEATURE:
<223> OTHER INFORMATION: primer LA1 forward

<400> SEQUENCE: 21
ggatcgcaga tacggtcgc                                                19

<210> SEQ ID NO 22
<211> LENGTH: 20
<212> TYPE: DNA
<213> ORGANISM: artificial sequence
<220> FEATURE:
<223> OTHER INFORMATION: primer LA1 reverse

<400> SEQUENCE: 22
cctcggtgaa gacaacgctg                                                      20

<210> SEQ ID NO 23
<211> LENGTH: 22
<212> TYPE: DNA
<213> ORGANISM: artificial sequence
<220> FEATURE:
<223> OTHER INFORMATION: primer RA1 forward

<400> SEQUENCE: 23
ctccttgaga acctgcgttt cc                                                   22

<210> SEQ ID NO 24
<211> LENGTH: 22
<212> TYPE: DNA
<213> ORGANISM: artificial sequence
<220> FEATURE:
<223> OTHER INFORMATION: primer RA1 reverse

<400> SEQUENCE: 24
ctgaagtacg ttttcccaag cc                                                   22

<210> SEQ ID NO 25
<211> LENGTH: 24
<212> TYPE: DNA
<213> ORGANISM: artificial sequence
<220> FEATURE:
<223> OTHER INFORMATION: primer LA2 forward

<400> SEQUENCE: 25
cgttatcaca aagaagccag gtcc                                                 24

<210> SEQ ID NO 26
<211> LENGTH: 22
<212> TYPE: DNA
<213> ORGANISM: artificial sequence
<220> FEATURE:
<223> OTHER INFORMATION: primer LA2 reverse

<400> SEQUENCE: 26
gctgctcttc gatttccttg gt                                                   22

<210> SEQ ID NO 27
<211> LENGTH: 23
<212> TYPE: DNA
<213> ORGANISM: artificial sequence
<220> FEATURE:
<223> OTHER INFORMATION: primer RA2 forward

<400> SEQUENCE: 27
tcatcaacct caacaagcac ctc                                                  23

<210> SEQ ID NO 28
<211> LENGTH: 19
<212> TYPE: DNA
<213> ORGANISM: artificial sequence
<220> FEATURE:
<223> OTHER INFORMATION: primer RA2 reverse

<400> SEQUENCE: 28
gtgaagacag cggcggtcc                                                       19

```
<210> SEQ ID NO 29
<211> LENGTH: 22
<212> TYPE: DNA
<213> ORGANISM: artificial sequence
<220> FEATURE:
<223> OTHER INFORMATION: primer

<400> SEQUENCE: 29
gccatgaaat ccaatcattt cc                                              22

<210> SEQ ID NO 30
<211> LENGTH: 20
<212> TYPE: DNA
<213> ORGANISM: artificial sequence
<220> FEATURE:
<223> OTHER INFORMATION: primer

<400> SEQUENCE: 30
gacggcattt gagcaacatc                                                 20

<210> SEQ ID NO 31
<211> LENGTH: 22
<212> TYPE: DNA
<213> ORGANISM: artificial sequence
<220> FEATURE:
<223> OTHER INFORMATION: primer

<400> SEQUENCE: 31
ttagtccatt cagcaagctg cc                                              22

<210> SEQ ID NO 32
<211> LENGTH: 22
<212> TYPE: DNA
<213> ORGANISM: artificial sequence
<220> FEATURE:
<223> OTHER INFORMATION: primer

<400> SEQUENCE: 32
ttagtccatt cagcaagctg cc                                              22

<210> SEQ ID NO 33
<211> LENGTH: 23
<212> TYPE: DNA
<213> ORGANISM: artificial sequence
<220> FEATURE:
<223> OTHER INFORMATION: primer

<400> SEQUENCE: 33
tttgaagatg gatgagaagt cgg                                             23

<210> SEQ ID NO 34
<211> LENGTH: 19
<212> TYPE: DNA
<213> ORGANISM: artificial sequence
<220> FEATURE:
<223> OTHER INFORMATION: primer

<400> SEQUENCE: 34
tgtcctggtg ggtgggttg                                                  19

<210> SEQ ID NO 35
<211> LENGTH: 20
<212> TYPE: DNA
<213> ORGANISM: artificial sequence
<220> FEATURE:
<223> OTHER INFORMATION: primer
```

<400> SEQUENCE: 35
ctcgaacgag aatgggaacc                                        20

<210> SEQ ID NO 36
<211> LENGTH: 20
<212> TYPE: DNA
<213> ORGANISM: artificial sequence
<220> FEATURE:
<223> OTHER INFORMATION: primer

<400> SEQUENCE: 36
ggcggaatga gatgcgacag                                        20

<210> SEQ ID NO 37
<211> LENGTH: 26
<212> TYPE: DNA
<213> ORGANISM: artificial sequence
<220> FEATURE:
<223> OTHER INFORMATION: primer

<400> SEQUENCE: 37
tgatttaata gctccatgtc aacaag                                 26

<210> SEQ ID NO 38
<211> LENGTH: 20
<212> TYPE: DNA
<213> ORGANISM: artificial sequence
<220> FEATURE:
<223> OTHER INFORMATION: primer

<400> SEQUENCE: 38
acgggttcgc ataggtttgg                                        20

<210> SEQ ID NO 39
<211> LENGTH: 20
<212> TYPE: DNA
<213> ORGANISM: artificial sequence
<220> FEATURE:
<223> OTHER INFORMATION: primer

<400> SEQUENCE: 39
cgaccgcgac ggtgactgac                                        20

<210> SEQ ID NO 40
<211> LENGTH: 22
<212> TYPE: DNA
<213> ORGANISM: artificial sequence
<220> FEATURE:
<223> OTHER INFORMATION: primer

<400> SEQUENCE: 40
gaatcaggac ggcaaactga at                                     22

<210> SEQ ID NO 41
<211> LENGTH: 25
<212> TYPE: DNA
<213> ORGANISM: artificial sequence
<220> FEATURE:
<223> OTHER INFORMATION: primer

<400> SEQUENCE: 41
gggtaaacga ctcataggag agttg                                  25

<210> SEQ ID NO 42

```
<211> LENGTH: 24
<212> TYPE: DNA
<213> ORGANISM: artificial sequence
<220> FEATURE:
<223> OTHER INFORMATION: primer

<400> SEQUENCE: 42
gggatatttg acacgattct gagg                                              24

<210> SEQ ID NO 43
<211> LENGTH: 20
<212> TYPE: DNA
<213> ORGANISM: artificial sequence
<220> FEATURE:
<223> OTHER INFORMATION: primer

<400> SEQUENCE: 43
ccggagatcc tgatcatccg                                                   20

<210> SEQ ID NO 44
<211> LENGTH: 19
<212> TYPE: DNA
<213> ORGANISM: artificial sequence
<220> FEATURE:
<223> OTHER INFORMATION: primer

<400> SEQUENCE: 44
cgtggtctag ctgccctcc                                                    19

<210> SEQ ID NO 45
<211> LENGTH: 23
<212> TYPE: DNA
<213> ORGANISM: artificial sequence
<220> FEATURE:
<223> OTHER INFORMATION: sequence for CRISPR pgkA

<400> SEQUENCE: 45
ctgcgtcggc aaggaagttg agg                                               23

<210> SEQ ID NO 46
<211> LENGTH: 23
<212> TYPE: DNA
<213> ORGANISM: artificial sequence
<220> FEATURE:
<223> OTHER INFORMATION: sequence for CRISPR gsdA

<400> SEQUENCE: 46
catcagcggc caatatgaca agg                                               23

<210> SEQ ID NO 47
<211> LENGTH: 19
<212> TYPE: DNA
<213> ORGANISM: artificial sequence
<220> FEATURE:
<223> OTHER INFORMATION: primer

<400> SEQUENCE: 47
cttggggaat tgggacacg                                                    19

<210> SEQ ID NO 48
<211> LENGTH: 20
<212> TYPE: DNA
<213> ORGANISM: artificial sequence
<220> FEATURE:
<223> OTHER INFORMATION: primer

<400> SEQUENCE: 48
```
tcttgccgat gagcttctcc                                               20

<210> SEQ ID NO 49
<211> LENGTH: 22
<212> TYPE: DNA
<213> ORGANISM: artificial sequence
<220> FEATURE:
<223> OTHER INFORMATION: primer

<400> SEQUENCE: 49
cagatcatcc tcctggagaa cc                                            22

<210> SEQ ID NO 50
<211> LENGTH: 20
<212> TYPE: DNA
<213> ORGANISM: artificial sequence
<220> FEATURE:
<223> OTHER INFORMATION: primer

<400> SEQUENCE: 50
acggcacgaa tgttcacctg                                               20

<210> SEQ ID NO 51
<211> LENGTH: 24
<212> TYPE: DNA
<213> ORGANISM: artificial sequence
<220> FEATURE:
<223> OTHER INFORMATION: primer

<400> SEQUENCE: 51
attggaagct ggctctatct cacc                                          24

<210> SEQ ID NO 52
<211> LENGTH: 23
<212> TYPE: DNA
<213> ORGANISM: artificial sequence
<220> FEATURE:
<223> OTHER INFORMATION: primer

<400> SEQUENCE: 52
gctgttcttc gatttccttg gtg                                           23

<210> SEQ ID NO 53
<211> LENGTH: 21
<212> TYPE: DNA
<213> ORGANISM: artificial sequence
<220> FEATURE:
<223> OTHER INFORMATION: primer

<400> SEQUENCE: 53
tcaacctcac caagcacctc g                                             21

<210> SEQ ID NO 54
<211> LENGTH: 20
<212> TYPE: DNA
<213> ORGANISM: artificial sequence
<220> FEATURE:
<223> OTHER INFORMATION: primer

<400> SEQUENCE: 54
caaacagccc gtcgcaactg                                               20

<210> SEQ ID NO 55
<211> LENGTH: 1881
<212> TYPE: DNA

<213> ORGANISM: artificial sequence
<220> FEATURE:
<223> OTHER INFORMATION: amplicon 5'pgkA A. niger

<400> SEQUENCE: 55

```
ggatcgcaga tacggtcgca cagttaatca cggctttcaa ggctcgtgga ggacgcaggc      60
cctctgacag taacgatctt atttcaattg agatccatga cctcgataaa gagaagccgc     120
ctgctcttgg agagctggga catgctagac atatgccgcc gcccttcgac ttcgagcgcc     180
tgactcgctt tatgtcgtac ggtttcttca tggccccggt tcagttccat tggttcggtt     240
tcttgtccag ggcgttcccc cttaccaaga ggaacccgtc gattcccgcg ctgaagagag     300
tgtgcgtgga tcagctgatg ttcgctcctt ttggtatgaa ctgtctccga aggaagaaga     360
aagctctttt ctcttagcta atattattac caggtctggc gtgcttcttc tccttcatga     420
cggttgcaga gggaggagga aggagagcct tgacgcgcaa gttccaggac gtctatctgc     480
caaccctcaa ggccaacttt gtcctttggc ccgctgttca gattctgaac ttccgtgtcg     540
tacctatcca gttccagatt gtgagtacta ttgtgataaa actcttgtgc actgttatac     600
tgatatttct tttttcttcc agcccttcgt gtcttccgtc ggaatcgcct ggactgcgta     660
tctgtcgctg accaactctt cggaggagga gtaatggtag tagcgggctc atattttggc     720
tcccacaagg ttcccaatcg tttcttctgt caattgtctg tcattcttcc ttcccctgcg     780
tcgtttcgtg cttactgggc gctgtaaatg aacttcgggg gttctgttat tcttcctctc     840
atgggtggtg tataggtctt cgtccagcag tgtgggtaca ccggagtcaa ttgcattgat     900
cgataaacca tgtcgacaaa atgaattata caccattgtt tttcgggttt gaaccaggca     960
cgaatgatgg aatgtctcct gtaggcgggg ttgtccccac gagcgagccg gcatccatag    1020
acgagaaata tcggaacgat tgcttgatag atccacccc ggacgcagca gaagctccca    1080
tcgcagcaat gatccgaggc taaggggctc cgaacggggc ataacaggca taatgttcac    1140
ccctgaggcc ccggacccctt ccgtcatcga ttcgcgggcg ctgacatcag tcccgcatca    1200
gcccgaggcg cccgcgattt caacttctct caccggctgc cccaccacca gcccatacca    1260
cttttacccc gccgccgaac cgaatgaagt cgtagcttcc agtgaccaga ctcgctcacc    1320
gcggacctat taagtaggca ttttttcccaa tctcctcatc ccccgtggtg ctactaatac    1380
tacgtctctc cccctcccaa tttctccttt ctctctttt ttgtcacccc acttccctat    1440
cttcccctca catcctctaa ccccgtccga ctgtcgtaga accgtcgttc atcatgtctc    1500
ttaccaacaa gctcgctatc accgatgtcg acctcaagga caagcgtgtc ctgatccggg    1560
tatgttgttg ccccggaaac ccccaccttt tcatcagtca ccgtcgtggg gtttaagatg    1620
agccttcaat gctaactagt ctgctcactg gacaggtcga cttcaacgtc cccctcaatg    1680
acaagaagga gatcaccaac aaccagcgta tcgtcggtgc tctgcccacc atcaagtacg    1740
ctatcgagaa tggtgccaag gccgttgtcc tcatgtccca cctgggccgc cccgacggca    1800
agaagaacga caagtacagc ctgaagcccg ttgttgccga gctggagaag ctgcttggcc    1860
gcagcgttgt cttcaccgag g                                              1881
```

<210> SEQ ID NO 56
<211> LENGTH: 1883
<212> TYPE: DNA
<213> ORGANISM: artificial sequence
<220> FEATURE:
<223> OTHER INFORMATION: amplicon 3'pgkA A. niger

<400> SEQUENCE: 56

```
ctccttgaga acctgcgttt ccacgctgag gaggagggca gctccaagga tgccgagggc     60
aagaaggtca aggccgacaa ggagaaggtc gctgagttcc gcaagggtct gactgctctt    120
ggtgatgtct acatcagtaa gtcatccttt tctcacacct tccatcttgg gaggccacta    180
gtttatgagc tgtgtactaa tattccacac cacagacgac gctttcggca ctgcccaccg    240
tgctcactct ccatggtcg gtgttgacct tcctcagaag gcttccggtt tcctcgtgaa     300
gaaggagctc gagtacttcg ccaaggctct cgagagcccc cagcgcccct tccttgccat    360
cctgggtggt gccaaggtct ctgacaagat ccagctgatc gacaacctgc tgcccaaggt    420
caacagcctg atcatcaccg tgccatggc tttcactttc aagaagaccc tcgagggtgt     480
caagatcgga aacagtctct tcgacgaggc tggcagcaag atcgttggcg aggtcgtcga    540
gaaggccaag aagcacgacg tcaagatcgt tctgcccgtc gactacgtca ctgccgacaa    600
gttcgctgct gatgccaaga ccggcactgc taccgacgct gagggtattc ccgacggcta    660
catgggtctg gatgttggcg agaagagtgt tgagctctac aagcagacca ttgctgaggc    720
caagaccatc ctctggaacg gtccccccgg tgtcttcgag ttggagccct cgccaacgg     780 caccaagaag accctcgatg ccgtcgtctc cgctgctcag tccggctcca tcgtcatcat    840
cggaggtggt gacactgcca ccgttgccgc caagtacggt gtcgaagaca agcttagcca    900
cgtctccacc ggtggtggtg cctctctgga gctcctggag ggcaaggagc tgcccggtgt    960
tgctgccctg tcgagtaagt aaatttgaac aaacatatta ccactctgga tatgcggaga   1020
tgctgcaaga caaatccgt ccatgtttct ttggaggagg atgagctgtg gttgagcttc    1080
catgctcggg actagtggac aggcggcttg tgtagtacct gtcagccttc ccggcgcccc   1140
ttcaagacag ggaacaattt tacgaatgta atgtacaaag aatgataatt aatctcaaca   1200
aaatacgcgt ttaccttcat tatcaagatg atgcaatctc atgactagtg acgggtccga   1260
agctgtgagt ctagttttat caaatgcgag ctacgaagag ggggccacaa gttgatgggc   1320
ggtggacttg atccttcag taatgggtgt gtaaataatc gtagaaagta cataatgtgc    1380
tcatgcagca catacaccgc ttccagcgaa gtgctagcct gtaccagatc tcccaccata   1440
gacgacttat cctctgcaga cgaatcctcc acaaccacgc agctgggcta gccaccggtc   1500
cggcaccgcc aaagcagacg aatctcttac tcaaacaagt ctatctagct ccaacattgt   1560
tcatcgtctc gctaccgagc cgcgtgaggg taaagctgca cgtgtaatca agtgattaat   1620
gcttcgtgga atttgcgtgt gttcatctca attaaaccga taaccgtca tctaacataa    1680 tctattgatt agacgccccg accttcttca gctcctctct gtagtttgaa gcaaacatgt   1740
tagtccaatt tgagctttag atgaggtgta gatcaatggt aacatattgc gctcatagca   1800
ttgaccgatg aggtttggtt tggttcggtt tggttcggtt tggtttggtt cggtttggct   1860
tggcttggga aaacgtactt cag                                           1883
```

<210> SEQ ID NO 57
<211> LENGTH: 1814
<212> TYPE: DNA
<213> ORGANISM: artificial sequence
<220> FEATURE:
<223> OTHER INFORMATION: amplicon 5'gsdA A. niger

<400> SEQUENCE: 57

```
cgttatcaca aagaagccag gtcctgagct gacctacctg catgaatggg ctggggctg      60 ctccacaatt gccagtaaac tcgaggtgcg cgtgccccgc gcatataacc aatgtagtac    120
```

```
agcgtcagac cgcaagaaac tcggcacctc tgcatttgcg gctttccttt gttttaattc    180
cagaggataa aactgtcaga tcagggtcgg agggttaata ttactgggat aagttgacgc    240
gggggggttcc gcatgcaaca gtaaggtgta ccttaagatg ggcatcatcc gttccatgtg   300
tggttctcag tggagctggg aggagattta cagcggacct ggctcggata aatcagtccg    360
tctagaaaag aaagggctgt tagttcaaac gatcatgctt ctgaaagaca gatagagtaa    420
gtcgagtgga ggatgcttca tcgtaagcac tgatttagag atatctagat tgtctcaagt    480
ggtagatagt agagtaagac tcatcgcgtt acctagcgat gatataagag atgggttgcc    540
acaacgggct ccgaaagaga gaaggagtac tacagtatga gtgggaacgg aggacctgac    600
aatttagggg atgaatgcta gggatgaaaa aggaagcatt tcccggagta atcataccag    660
ggaaatactg gataagttga ggtaaactag caggcagtgt gtcttgagtg atgtaaaata    720
accccgaata atagaattgg ataacaacta ctactcactc ctcacggggt cccgcggcag    780
caatcgacgt agtggaagaa cccaagccgg gcttcccagt aacaaagtag taacaaagct    840
gccccacccg ggctcactca cttttgccca ccctgcagcc agcagctcct ctcctcgacg    900
agaggccctc cggtcttaaa aagtacttgc tccgccggaa ctgttgggat ttttccaaca    960
aacctctctg tccttgctgt ctccctgtat cctctttatt tcctcctctt ccctcctcca   1020
ccgaatctct caccttttcct tcccatctcg tggttgttca cacatcagta aaacatggcc  1080
agcacaatag cacgcactga ggaacgcag aatgctgggt gagttttgcg gtctccctct    1140
ctgacatcac accctcctc ccactcccgt ccctcctgcc cgccgccag acgtgaggat     1200
tcaccaccca cgactctcca taacaagccc cgtcgcccaa acattcactg gcaggcttcc   1260
cgctttccat tattcttcaa ttcgtcacca ggattactcc ttcgggctta acgaaaggac   1320
tatccttctg actcaccacc aaccctcact gcccctcctg catgctgtag cggactgcgg   1380
gcaccgacct gcatcatcga tctacacccg atccctgtga cattatattc gtcaagctat   1440
agcctagcta acatggatgt tttacgtagc accatggagc tcaaagatga cactgtcatc   1500
atagtactgg gtgcctccgg agatcttgca agaagaaga ccgtcagtga cgaccccctg    1560
attcatgttg acctgacaga aagctaacct tttacagttc ccggccctttt tcggccttgt  1620
atgtcctctc ccagatccaa ttgcagtttg actcaccagt atggttgctg atttgcgctt   1680
ccagtatcgc aacaagttcc tccccaaggg aatcaagatc gtcggatatg cccggacaaa   1740
catggaccat gaggagtacc tgaggcgtgt gcgctcatac atcaagaccc ctaccaagga   1800
aatcgaagag cagc                                                    1814

<210> SEQ ID NO 58
<211> LENGTH: 1837
<212> TYPE: DNA
<213> ORGANISM: artificial sequence
<220> FEATURE:
<223> OTHER INFORMATION: amplicon 3'gsdA A. niger

<400> SEQUENCE: 58
tcatcaacct caacaagcac ctcgaggaga ttgagaaggg ccagaaggag cagaacagaa     60
tctactacat ggccctcccc cccagcgttt tcaccaccgt ttccgaccaa cttaagcgca   120
actgctaccc caagaacggc gttgcccgta tcatcgtgag tcaatcctgg gctggtatca   180
ccctgccatt ggtcattatt cttactcgct tgttttccta tttcacaggt agagaagcct   240
ttcggcaagg accttcagag ctcgcgcgat ctccaaaaag ccctggagcc taactggaag   300
gaagaggaga tcttccgtat cgaccactac ctgggtaagg agatggtcaa gaacatcctt   360
```

```
atcatgcgct tcggaaacga attcttcaac gccacctgga accgtcacca catcgataac      420
gttcaggtac gaccttgcgc tatccaattg gcctattgat ttacttgcta aattgtcgct      480
tctatcatta gatcacattc aaggagccct tcggcactga gggacgtggt ggttacttcg      540
atgaattcgg catcatccgt gatgtcatgc agaaccgtac gttcaaagtc acgctcgaca      600
tctccgacat gatgctgata aaatctctc ctagaccttc tccaggtgtt gacgctgctc       660
gctatggagc gccccatttc cttctccgcc aggacatcc gtgacgagaa ggtacagtgt       720
gcgcttgact attggttgtg ctgggttact gacacttaac caggttcgtg tcctccgtgc      780
gatggacgcc attgagccca agaacgtcat tattggccag tacggaaagt ctctggatgg      840
cagcaagccc gcctacaagg aggacgagac cgttccccag gattcccgct gccccacctt      900
ctgcgctatg gtcgcctaca tcaagaacga gaggtgggac ggtgttcctt tcatcatgaa      960
ggctggcaag ggtatgtacc tctttccaag cgatcatagc accgattggt atactaataa      1020
ttcgcagcct tgaacgagca gaagaccgag atccgtatcc agttccgtga cgttacctcc      1080
ggaattttca aggacatccc tcgcaacgag ctcgttatcc gcgtccagcc caacgagtcc      1140
gtgtacatca agatgaactc caagctgcct ggcctgtcca tgcagacggt tgtgactgag      1200
ctcgacctca cctaccgccg ccgcttctcc gacctcaaga tccccgaagc ctacgagtct      1260
ctgatcctgg atgctctgaa gggcgaccac tccaacttcg tccgtgacga tgagctggat      1320
gccagctgga ggatcttcac ccctctcctg cactacctgg atgacaacaa ggagatcatc      1380
cccatggaat acccctacgg tacgtgcact tcttgcaatt tgtctaaatc gcttacatac      1440
tgaccaacgc gcaggctccc gcggacccgc cgtccttgat gacttcaccg cgtccttcgg      1500
ctacaagttc agcgatgctg ctggctacca gtggcccttg acttccaccc caaccgtct       1560 gtaaataagg gcggtcggca ggttatgacg gatgaggatg aaaaaaaaat tattgccaaa      1620
aaaggctaaa aaaagatgt taatgcgatt gattttcggt cgagaatcat ggtatgacgg       1680
ggcatctggg atgatatgac agaaatgaag cactcggac tatttatcgg tcggctgggc       1740
aataactgga gttatctatt cgcaaccct ttttagaaac gaatgcagag aacgtaacga       1800 accaccccg gtcggttggg accgccgctg tcttcac                               1837
```

<210> SEQ ID NO 59
<211> LENGTH: 1494
<212> TYPE: DNA
<213> ORGANISM: artificial sequence
<220> FEATURE:
<223> OTHER INFORMATION: promoter PmbfA

<400> SEQUENCE: 59

```
gccatgaaat ccaatcattt ccttctggcc gccctcgggc aagagatagt gccgcagagg       60
tctctcacag catctacatc tgcgaccgca acagccacca agcgaggcgc acatgagctt      120
gtcctcctcc catgccaaag tttggccctc ttcgtttctg tgatgctgaa ggaagtcaaa      180
ctcgtcgatg ataggaccag atggtttgtc aagggtcaac gctttccatg ccttctggca      240
ccggtagtaa tgctcttctg caagggagac ttgacgtttc ggatccgcgg gccccgggac      300
atgctggaag ggattttctg gctcaatacc acgtctgtat ttgaccccttt ccagacagtt     360 aatccgctgc aggagggcga actgtagctc ctcgttctcc ttgtagcgct tgatccagtc      420
tttttggatg ttgcacttgc ttggcctatg cttctcatat aatcttgccc tgtcatagag      480
acgacgtctg agattgtagc gttcgtcttt gatcacccgg agccagatag gcctgagtat      540
```

```
atctgacatt agatcaaagg gtctgtggat agtctccttc agcatcagcg acgcatgtga    600
ctcgcaagtc ggagagagct tgtgggtggt catctttgat ggcgtcctct gctttccctt    660
gattttcgtt gattgttttt cgaaagttaa gtctggcagt caagagaatc cttctgccag    720
acattatatt tacgtatact gacgtagtag aaacagcgtc aggatgagga catggtgtgt    780
gctggaccac ggaatcatag ttcatcagta tattgggttg acaaataac gctgagcatg     840 tatatgtctt tacacactat aaaagccagc gaacgccaat aaaatagggc atattgatgt    900
gaaaatatga caccagttaa aagcagtgta ttgattttat ctctcttcac ctcggaccta    960
tactaccgta tacaagactc aacttacttc cagatatagt aatatacacc ctatggacga    1020
accagcacaa taattacagc caaacaacac cacccaaatg gcatattcct aatcagcact    1080
aagcacaaat accactgtca tcacagcata atcaataaga atcccagaca accgactcac    1140
tctgactcac cttacacaaa cccccaagca aagcgcagcc cagaacctca gccaacaatc    1200
gggcaacgta cggggaaaga ttggccgatc catgatgtca gcagccctaa cccaaagcgg    1260
actagcgcat accgcccctc tgactccgcc atcccagggc tcgagaagct tccgtggcgt    1320
cgatataaat tcagcgggcc ttgaacatcc ctccttacga cacacctcac gcgatcgatt    1380
ttgacactca cgcaccgcca ccctcacatc ctccacccac accacacccc ttaatcaacc    1440
caccatcacc gctagaacgt ctatctcatc accgacttct catccatctt caaa          1494
```

<210> SEQ ID NO 60
<211> LENGTH: 1498
<212> TYPE: DNA
<213> ORGANISM: artificial sequence
<220> FEATURE:
<223> OTHER INFORMATION: promoter PcoxA

<400> SEQUENCE: 60

```
gacggcattt gagcaacatc atgcgaacgc gaccgtgtta tcagcagcca ctcagcaacc    60
gtcagttcat gatatgtcgc agagcgttgt cctcggcccg ccccagatgc tcccacgaca    120
ccttccagtg cagtatccac ctgccagctt cgaaatcccc cctatccagc gcgagaaaaa    180
acgccatcac tcggagaccg aagaggatgg gaaccccgac catggcctgc ggccgcagct    240
atcagtcctc tcagctgacg cccctcacga accctcgcac tctcccgaaa tgctcttcgg    300
tgtccatggc gcatcatctc agcagcatcc catgtcaaac catggctttg ggcccacgga    360
ctctgtggcc ctgccgcaac atcaccatca ccatcgactc ccgccccatg cagcgctgcg    420
cgccccaggg cgtcatggag tgaatgtgga atctcctcct ttgccctcgg gcccgccgag    480
tgtggtgggc cagcctggaa tgcctgatcc agcccccagg cctcgaggac caaaactgaa    540
gtttactccc gaagaggacg ctctactggt gtagttgaag gaaaacaaga acttgacgtg    600
gaagcaaatt gcagacttct tcccgggccg aacgagcggt accttgcaag tccgatactg    660
caccaagctg aaggctaagg atgtagcttg gagtgacgaa atggttcgat ttgctcctga    720
tgtatttcta cgcctgtctc acacatgcta atgaaggaa taggtacaaa ggctgcagcg     780
ggcaatgcac gagtacgaga acgatcggtg gcgcatcatt gcaggaagg ttggaaatgg     840 cttcaccccca gctgcttgcc gcgagaaagc catgcagctc catgagtaaa agcgttgggg   900
aattttcata tttatatcta ctgtcgccag attcggccct gcttggaccc tctgatctcc    960
ttactctcca tattggttca aatgtcgggt ctccgatagg gctggtggtg caggcttgtt    1020
gtaggcacgg gaggatgatc agcataactc tgagtcacta tagggacggg ttgatgtaag    1080
gtattaagtg atgtatgata attcatttta gcccggggga acatatggcg ccggcatttg    1140
```

```
ttcgttcgca atgaaccgac actagcgtcc gctctcgcag tttagcaccg gctgatcccg    1200
ggctgaacgc ggccattgct cggccggggc atgtgttcct tatctacggc agaccgcaga    1260
agaccactgg agcagattat agaccctaag ccctaagccg acacccaat cgagtaggtc     1320 tgcggaccag gtcactgcgg gcagccgag aagctccgca accaatcaat ccccggcgct     1380
gactaagggc aggcgaccac gggccgaagc ggcttcaaac tcacctcaac ctccaaactc    1440
cctcatctcc aaacgtcctt gccttgtctg ccgtcattgc aacccaccca ccaggaca     1498
```

<210> SEQ ID NO 61
<211> LENGTH: 1490
<212> TYPE: DNA
<213> ORGANISM: artificial sequence
<220> FEATURE:
<223> OTHER INFORMATION: promoter PsrpB

<400> SEQUENCE: 61

```
ttggcagggt cacgtagccg taattatttt cggggaaggt tggaatgcaa tggaaggaga      60
tttccgtagc tagggctttg atcgatgcgg ggagcactgc cggtaggagg tctgggtga     120 atggggtgat atgcaggcgc ttcgtatcgg acggtgtggt cgtcatttgc ccaatagata    180
gttagataga tacctgagta cggtagcagt gcaggtgacg gctaagaagt cggagggaaa    240
aaggtgcagt cacaagcgca ttcagcctaa caagtgtctt tgatactcgg tgagaaacaa    300
acttgagtag aataagacag aaagttcttg tgaatggtca caatgggctt ccaacgaagc    360
atcaagcaga ccctgttgca atagatattc caagaccgaa aaattaatga taggatcagt    420
tattggccga gggattttcc gggccgccaa gaccgggtta tggagatgtg gcgcaggcat    480
gccatcctca gccacaggtt tctgtgacat cccaaaagca ttgatcgaag ttggtataag    540
tttcattcta tctaccatgg tgacaaggaa gtacgggtgt agaaaagaaa aatctggtag    600
gaatagctca gcaacaaatg gcggaatgat tgatgtaaga ctcgatgtat ccactggaac    660
gagatgcaag ttgcaacagc aataaatgga tttcagcctc cattacaatg taacagtcgg    720
gccgatactc agccggagca ggatttggcg ggtgaatagt ggatccggag agaaacgacc    780
aggtaatctt tcgtacggga ccagacccga cccggcctgc ttttagtta ccagctgtta     840 cttgtgtaat ccccgtaaaa cgatcagtaa ctgccattga tcttcctgct cttttccctt    900
attccctttt cccctttga aacttatttt cttcttcctc ttcatcgctt aactacttaa     960
gtactaggat tctcactcgc cactcttccc caatatctaa agtagtctt gctacgaaga     1020 tcccttcccc ctacattact cctcctcctt caacacaccc accccccct gatcggccc      1080 cataccagtc ttcccgcggc taactaaagc ccgcacgtct gatctcatcg ccgcttccag    1140
cttcgacctc agtcgctcac atggccactc ggattcctta gcatcatctc ttttttccc    1200 atcccctccc cgccctacca actgagggtc ctctgaagtg tgctccacat ttccttccct    1260
tcacttattt tggatcctca tttttctttct tcctctgttt cggggcgttc ttcaacatcg    1320
ctacttagtc acttctctcc tctcattacc ggacgggaac ttcgctccct tctccgcttt    1380
cttatccgga ccgcctcttg ccaatctcac catcgatcct aacccgtcat aatccagtca    1440
ctcaacccta ctattgtcga catacacgtc ggttcccatt ctcgttcgag                1490
```

<210> SEQ ID NO 62
<211> LENGTH: 1500
<212> TYPE: DNA
<213> ORGANISM: artificial sequence
<220> FEATURE:

<223> OTHER INFORMATION: Ppromoter PtvdA

<400> SEQUENCE: 62

| | | | | | |
|---|---|---|---|---|---|
| ttagtccatt | cagcaagctg | ccgttgggat | ccttggcttc | agccgtcaag | ggctggcctc | 60 |
| gcttgagcgg | ctctttgctg | aggaacacgg | agaaaaagag | gttagctgtc | tgccagcaga | 120 |
| gaaccaggag | gcctcctgaa | atcaaggttc | gcacgataac | tccgaggatt | ggcgggataa | 180 |
| tgccgggagg | ggatgcagcg | gatctcggga | aatcccagaa | tagctttgca | aagtacagtg | 240 |
| tagtgctcca | tgccgggcgc | cggaggacga | aggcgtatgc | gaatgggcaa | agaatggaaa | 300 |
| ccaagatact | ccgtttcatc | ccatctttga | tgagctgcgg | caatgctgac | tggaggcgtt | 360 |
| tagagatcga | ttgctcctgc | cggctatctt | catcagcgga | gccagcgacc | ctcctggcaa | 420 |
| cgggaagagg | gacgcgatcg | tagtcgtagt | aaagatgaac | cactgactgc | gcgactgcca | 480 |
| ggagaaagtg | gtaggtataa | aggtagattg | ctctttcgtt | taagcttgct | cgttcgtgag | 540 |
| gtctagcata | actagttagg | cgagttcaag | agaaccgctt | gagctcgtcg | tcgcaggaaa | 600 |
| catacctagc | tcggttcacc | aattccaggt | gtgcgctact | tgaagaagac | cacctgtaga | 660 |
| tttcagtgaa | ccaccaggcg | gagaacaagt | accagccaaa | agtctgtata | acgtcgaggg | 720 |
| gaacgaggta | tttgaaggtg | ctaagcgggg | aggaggttgt | cctggcaccg | atgtgcatct | 780 |
| gaccaacacg | gaggacgaag | acaacgagac | tgcagaggaa | gagaagaact | gtgcgaactc | 840 |
| cacatcctcc | aatggggaac | caagcccaca | agactatcga | gatatcacag | ctggttagcg | 900 |
| atcacagctt | gtcaaacgcc | gctcggtgtt | ggtgtaaact | tacaagatga | cttatcgcca | 960 |
| atagcaaatg | ccactacata | gcagaccaga | agcgccagtg | ccgacgcatg | aacgaatcgt | 1020 |
| ctgtgcagcg | cagaggtcaa | gatgcgccga | tacgggcgag | gctgtgctgc | agccatggtg | 1080 |
| caaggtggaa | gagggactgt | gagatctcta | gggagagaag | agacaaagca | atttcactgc | 1140 |
| atgatcagat | gacaggagga | attgaggtat | ccggtcagcc | tgtcagaacg | gaaagctccg | 1200 |
| aaggggggca | agtggagctt | caaggaggag | tgtcggcgtc | ggatgcgaca | ataaagtgaa | 1260 |
| gcttttcggg | caaagcatca | aaacacgcac | cagccacaaa | cggcatgtca | tgtgacaccc | 1320 |
| caccagccat | cgatggcgtc | aggtgagtgg | cagcctgcga | atcatggcat | ctgtgcggcc | 1380 |
| aggcaaccgt | cgacacctga | cagcgataac | gtactactac | tttagcaggg | agagagccgg | 1440 |
| ccggttgcat | cggccgaatg | atcccacctt | catccatcca | ctgtcgcatc | tcattccgcc | 1500 |

<210> SEQ ID NO 63
<211> LENGTH: 1064
<212> TYPE: DNA
<213> ORGANISM: artificial sequence
<220> FEATURE:
<223> OTHER INFORMATION: terminator TglaA

<400> SEQUENCE: 63

| | | | | | |
|---|---|---|---|---|---|
| cgaccgcgac | ggtgactgac | acctggcggt | agacaatcaa | tccatttcgc | tatagttaaa | 60 |
| ggatggggat | gagggcaatt | ggttatatga | tcatgtatgt | agtgggtgtg | cataatagta | 120 |
| gtgaaatgga | agccaagtca | tgtgattgta | atcgaccgac | ggaattgagg | atatccggaa | 180 |
| atacagacac | cgtgaaagcc | atggtctttc | cttcgtgtag | aagaccagac | agacagtccc | 240 |
| tgatttaccc | ttgcacaaag | cactagaaaa | ttagcattcc | atccttctct | gcttgctctg | 300 |
| ctgatatcac | tgtcattcaa | tgcatagcca | tgagctcatc | ttagatccaa | gcacgtaatt | 360 |
| ccatagccga | ggtccacagt | ggagcagcaa | cattccccat | cattgctttc | ccaggggcc | 420 |
| tcccaacgac | taaatcaaga | gtatatctct | accgtccaat | agatcgtctt | cgcttcaaaa | 480 |

```
tctttgacaa ttccaagagg gtccccatcc atcaaaccca gttcaataat agccgagatg    540
catggtggag tcaattaggc agtattgctg gaatgtcggg gccagttggc ccggtggtca    600
ttggccgcct gtgatgccat ctgccactaa atccgatcat tgatccaccg cccacgaggc    660
gcgtctttgc tttttgcgcg gcgtccaggt tcaactctct ctgcagctcc agtccaacgc    720
tgactgacta gtttacctac tggtctgatc ggctccatca gagctatggc gttatcccgt    780
gccgttgctg cgcaatcgct atcttgatcg caaccttgaa ctcactcttg ttttaatagt    840
gatcttggtg acggagtgtc ggtgagtgac aaccaacatc gtgcaaggga gattgatacg    900
gaattgtcgc tcccatcatg atgttcttgc cggctttgtt ggccctattc gtgggatgcg    960
atgccctcgc tgtgcagcag caggtactgc tggatgagga gccatcggtc tctgcacgca   1020
aacccaactt cctcttcatt ctcacggatg atcaggatct ccgg                    1064

<210> SEQ ID NO 64
<211> LENGTH: 549
<212> TYPE: DNA
<213> ORGANISM: artificial sequence
<220> FEATURE:
<223> OTHER INFORMATION: terminator TniaD

<400> SEQUENCE: 64
acgggttcgc ataggtttgg ggttgtatct tggcgttggg acggactggg tatggtgttt     60
cttttggata tatgacatga tatgtacacg gccgtgaatc tttaacttta tatcattata    120
gaaatgcact tgcacatttc aacacgctgc gagcagaatc tcgaagattg ttccgcaagt    180
attagatcat gagagcattt tcatttcctt tcaggcagtg ggagtaggcc atcctgaaaa    240
caaggcggcc actgtagact agtaataacct cttcatatcc aaccttacca gaagatgatc    300
aaacacattc gcagatccac ctctcgccgc gaaagccatc ccggcccttc cggtacccaa    360
tgcctttgat gacgatgcca ccgcccccct ggcaccatct aggctacgca ataccccaac    420
aaaagcggcc atttgcttcc taaacactgc atacaaccgc ttgaccatgg cttcactctc    480
gtgcctcacg ccatgtgtcc catccttgcg cgacagaggc gcaaacctca gaatcgtgtc    540
aaatatccc                                                            549

<210> SEQ ID NO 65
<211> LENGTH: 580
<212> TYPE: DNA
<213> ORGANISM: artificial sequence
<220> FEATURE:
<223> OTHER INFORMATION: terminator TgpdA

<400> SEQUENCE: 65
gaatcaggac ggcaaactga attcagaagt gtgctgtgag tgagactgat tgccgagcgc     60
agacgactct cgtggaaccc ggcttgtgga gaagcttgag aaggtcttaa ctcctagcgt    120
aaaagctcat gatgacgtac aatttaatga aatgatacaa tgttcatatt tcccgttcaa    180
atttccggcc ttggtcagtg cgtaagatgt ccacgattga atactaactc agtatgggtt    240
tggtagcatt ggcaatgtag ttataagcat gcaccggttg aagacgtcgg ccccagatgc    300
aatgctgcgg tggtgactaa gctctgcagt gaatggaatg cgtttctttg atcgacttcg    360
gcgtgccgcg ggatttttctc ggcgcttcta ctggtgcaga aggacgata ccactggctt    420 tcggtccatg ccacatccca gtctcccggg aaattcattg catactttaa gaaacaaact    480
gatctccata atttccgtct ttagagttca cttggtactt tgggtggat cgaggggtgt    540
```

-continued

| ccgcggccat ccaagtcacg tggagggcag ctagaccacg | 580 |

```
<210> SEQ ID NO 66
<211> LENGTH: 528
<212> TYPE: DNA
<213> ORGANISM: artificial sequence
<220> FEATURE:
<223> OTHER INFORMATION: terminator TtrpC

<400> SEQUENCE: 66
```

| tgatttaata gctccatgtc aacaagaata aaacgcgttt cgggtttacc tcttccagat | 60 |
| acagctcatc tgcaatgcat taatgcattg gacctcgcaa ccctagtacg cccttcaggc | 120 |
| tccggcgaag cagaagaata gcttagcaga gtctattttc attttcggga gacgagatca | 180 |
| agcagatcaa cggtcgtcaa gagacctacg agactgagga atccgctctt ggctccacgc | 240 |
| gactatatat ttgtctctaa ttgtactttg acatgctcct cttctttact ctgatagctt | 300 |
| gactatgaaa attccgtcac cagcccctgg gttcgcaaag ataattgcac tgtttcttcc | 360 |
| ttgaactctc aagcctacag gacacacatt catcgtaggt ataaacctcg aaaatcattc | 420 |
| ctactaagat gggtatacaa tagtaaccat ggttgcctag tgaatgctcc gtaacaccca | 480 |
| atacgccggc cgaaactttt ttacaactct cctatgagtc gtttaccc | 528 |

```
<210> SEQ ID NO 67
<211> LENGTH: 1713
<212> TYPE: DNA
<213> ORGANISM: artificial sequence
<220> FEATURE:
<223> OTHER INFORMATION: amplicon 5'pgkA A. terreus

<400> SEQUENCE: 67
```

| cttggggaat tgggacacgc caggaaccta ccgcccccgt ttgattttga gcggttgacc | 60 |
| cgtttcatgt cgtacggttt cttcatggcc ccggtgcagt tccagtggtt cgggttccta | 120 |
| tcgaggacct tccctctcac caagaagaac ccgaccatcc cggctctgaa gcgggtggcg | 180 |
| gttgatcagc ttatgttcgc tccgttcggt atggacctga tgttgtgcca cgagaaaaag | 240 |
| gatatcccgc taatagaaat gaatataggt ctggtctgtt tcttcacctt catgacaatt | 300 |
| gctgagggtg gcggacggag agccttgact cgcaagttcc aggatgtgta cctgccgaca | 360 |
| ctcaaggcga actttgtgct ctggcctgcg gtgcaaatcc tgaacttccg ggtggttccc | 420 |
| atccaattcc agattgtgag tttgctcttc tcccgtgacc cgacgcgttt tcattagtta | 480 |
| ttgtatactg attgcttttt cttttcacagc catttgtgtc gtcggtgggt atcgcatgga | 540 |
| ccgcatacct gtctctgacc aactcttccg aggaggagta aggtaaggta cgggttttct | 600 |
| cgttgcattg gatggttatc acttgatacc tatgttacc tggtcggccc ttggctttgg | 660 |
| aaatcttctt tgtggattct ttcttctttc cttgtgttgc gtggggtatg tttacggcgt | 720 |
| tttcaatgct gttttggggg gttctgtttc tcattggtgg tgtccggtct gtcacagggt | 780 |
| actctcaaag gtttcttcgt taggtattca aaaggcgcac aaatgctgga tttagatcat | 840 |
| caacccaagc ggaagagact attcaaagga gtctccattc gcagggatat ggaactgcca | 900 |
| ttctatgacg ctttcgggag aaatttccag gattttcgta ggtcgagaca cccacagagg | 960 |
| cacatgtagg gaccgcgggg gacgatgatc ctatgaatgc ccgtacgacg agaattccga | 1020 |
| agcggctgtt tccaattccc gcgagagatc cgaggctatc gagaacgcat agggacaatg | 1080 |
| ttcacccctg agagcccgga cccttccgtc atcgatcgcg gtggactgac atcagtcccg | 1140 |
| catcagcccg atgcgtcagc gaatctctca ccggacgccc caccaaacac tgctgctacc | 1200 |

```
ccgccgctgg gccgaagtta tcatatgggc tcaccgtgaa cggattgagc attttccct    1260 ccttcttcca attcacctca ccatctctcc tgcgaggtac tgctccctat ttctatccct    1320
ctagacccct gtggtatcgc tgacccgacg ccagctcctc cctctccaac ttcttcacca    1380
tgtctcttag caacaagctt gccatcactg acgtcgacct caaggacaag cgtgtcttga    1440
tccgggtatg tcacctccaa tggctgtggt atgatcggtc aatgctaacc acgctcacct    1500
cccaggtcga cttcaacgtc cctctcgatg acaacaagaa cgtcaccaac ccccagcgta    1560
tcgttggtgc tctccccacc atcaagtacg ctgtcgagaa tggcgccaag gccgttgtcc    1620
tcatgtccca cctcggtcgt cctgacggca agaagaaccc caagtacagc ctgaagcccg    1680
tcgtgcccgt cctggagaag ctcatcggca aga                                 1713
```

<210> SEQ ID NO 68
<211> LENGTH: 1820
<212> TYPE: DNA
<213> ORGANISM: artificial sequence
<220> FEATURE:
<223> OTHER INFORMATION: amplicon 3'pgkA A. terreus

<400> SEQUENCE: 68

```
cagatcatcc tcctggagaa cctgcgtttc cacgccgagg aggagggcag ctccaaggac      60
gccgagggca agaaggtcaa ggccgacaag gccgccgtcg aggagttccg caagggactg     120
accgctcttg gtgacatcta catcagtaag tctatttccc ctttggccca tggaccgtaa     180 ttgggttttgt ccatactaac gataccatcc agacgatgcc tttggaaccg cccaccgtgc    240
ccacagctcc atggtcggcg tcgacctccc tcagaaggct tccggcttcc tggtgaagaa     300
ggagcttgac tacttcgcca aggccctcga gaacccctct cgtcccttcc tggccatcct     360
cggtggcgct aaggtctccg acaagatcca gctgattgat aacctcctcc ccaaggtcaa     420
cagtctgatc atcaccggag ccatggcctt taccttcaag aagaccctgg agaacgtcaa     480
gatcggcaag agtcttttcg acgaggccgg cagcaagatc gtccccgaga tcgtcgagaa     540
ggctaagaag aacaacgtga agatcgtcct tcctgtcgac tacgtcactg ccgacaattt     600
cgctgccgac gccaagaccg gctacgctac cgatgccgac ggcatccctg acggcttcat     660
gggtctggat gtcggcgaga gagtgtcga gctgtacaag cagactatcg ccgaggccaa      720
gacgatcctc tggaacggcc cctgcggtgt cttcgagatg gagcccttcg ccaacggcac     780
caagaagacc ctcgacaacg tcgttgccgc cgctcagtcc ggctccattg tcatcatcgg     840
tggtggtgac actgctaccg tggccgccaa gtacaacgcc gaggacaagc tcagccacgt     900
ctccactggc ggtggtgcct ctctggagct tctggagggc aaggagctgc tggtgtcac      960 tgctctgtca agtaagtaaa cttttacgac catgtaatgt gttggaggga cgagttgcag    1020
aatgagatcg tgcttgtcca tgtgtattgg gcgagccatg gctgcatcag gccgtgtttt    1080
tttagcgtcc ctctccatcc cgtcgaggga tggccttttc tatgatgtaa tgtacaggca    1140
ttaaaattaa tcaaaataag cgaaatgatt ttgtttctcg attcaagaag ggttctgatg    1200
aagtaatggc tactagtgac gggatctaaa ctgtgagatc agacgcttgt cgttcccatt    1260
gaaatggata ttcttattgc gtagagcttc tcttatcttt tctatcaaac aattgttttc    1320
ataggatgtc cggagccat acaccgccag cgtccgtcac gatcatatat gcctggtaga     1380
tctgggccaa ggaccccggt cgcttctcca gtgggctggg cgccgttccc cttgacgaac    1440
gaacggccat gacgatccca ggtgaacgca aggccgggcg aactaccacc atagaacgga    1500
```

| | |
|---|---|
| catgatgtcc taataaagaa gaatgtagca tcttgatgat atagcttgtg ttccatcatg | 1560 |
| gaaaaagagg gcaaaaatag ataattctta tcgttcgttc attcgcgttc gggatattca | 1620 |
| gagtaccaca tgtccatccg tccattagtg agatgcctcg acctttttcca gttcctctct | 1680 |
| gtagcacgaa gagaaatacg ttagtgttgc gtaggcgtca gaggaagaag gggagcaacc | 1740 |
| gcactttagc tgtttcgaaa agtcctccgc cgcatcgtcg tcgtcccagc tctcctccca | 1800 |
| caggtgaaca ttcgtgccgt | 1820 |

```
<210> SEQ ID NO 69
<211> LENGTH: 1817
<212> TYPE: DNA
<213> ORGANISM: artificial sequence
<220> FEATURE:
<223> OTHER INFORMATION: amplicon 5'gsdA A. terreus

<400> SEQUENCE: 69
```

| | |
|---|---|
| attggaagct ggctctatct caccccctcct gacgaagacc tcagcagtgt acggtacact | 60 |
| ggagttaagc tgtccgtctc cgcggacacc tgacgagctt agatagaggg tgggttggat | 120 |
| tatggaccac accccggccg cctttatatt tcttttttctc cttttttgat gtcctggcct | 180 |
| tcgcctatca gaggagaatc ccactagatc ctaaactgac tgggcgtaag attactagta | 240 |
| ccatgtagca tttggcgcgg ggctaggagg tcagcatatc caagatgtgc ctctagagat | 300 |
| gcgtctccgg tccatgtacg gttcccggtg gagctcactg ggttgaaatt ccagcggag | 360 |
| taggctcgga taaaactagt gttaagaagc agttgagcag aagggttcgg atgattgggg | 420 |
| acggtagtaa tacaaggtac aagcaccggc atcgggaagg atttccttcg tgtcctctat | 480 |
| atccgagtgg gagggagtat gaacgggctg actgagtacc taggcaggcg tgagagggat | 540 |
| gatataatac cagtagctgt cgccacggcg gtggattcta gggagtaact actacgtaga | 600 |
| tgatgaaaag gaaaaagaac tgataaaaga tgacagatta tctatctccg gaaaaagggc | 660 |
| gggcacccga ggctatagtt atactacgaa gcataaataa aataataaaa acacctaatt | 720 |
| aaatccaaca cgaagatatc ctaggttccc aaagcccagt tgtatgtaat ttctctccag | 780 |
| ttaggttttt tcttacccag gccaccggac ggggctcgcg gcaacaatcg acgcccacc | 840 |
| gtgtactgta atcgagagtc accctgcagc aactgcagct cctcgactgc tgctacgact | 900 |
| aagcagagtc cctctcacgg cgttaaaaag tacttgctcc gccggaactg ttggggattt | 960 |
| ttccaacaaa cctcttctct ttcctcctct actccctcgt ctctccttca ttccaagctt | 1020 |
| catttcccctt cctaacagt ccgttgttca tttttggtgc ctgcacaaac tcccgtccgt | 1080 |
| caccatgacc agcacaatag cccgcactga ggaacgccag aacgctgggt gagtcttgac | 1140 |
| tgccgccgcc gctccctct ctgacatcac accccctcctc cgtcccccctc tacgtctttc | 1200 |
| ttttcttccc accgtctgc cacctgctcg atcgccttcc tcaggacagt caatatcagt | 1260 |
| caattcgacc ccagatttcc cacttcccctt cgttgaatgc cccgagctct tccaatttgc | 1320 |
| ttttagaaaa ttgtcgagca gctctagttt tcaattcccc cttcttccga tcgcgctggc | 1380 |
| aaatccctgt gatcgacatc atacagcttc ccctgctcag ccagtaacct tcgattcgct | 1440 |
| actaacatgg atgtctcgcg tagcaccatt gaactgaaag atgacacggt catcgtggtc | 1500 |
| ctcggtgcct ccggagatct cgcaaagaag aagacggtag gtgttctacc ctaaaaaggc | 1560 |
| ttggccggtg aagccgatcg gagactgact aggttccata gttccctgca ctgttcggtc | 1620 |
| ttgtaagtat acgatgacgg tccgagtaaa gtatcgtcgc gtcggttggc attgaccatg | 1680 |
| catttagtac cgtaacaaat tcctcccccaa ggggatcaag atcgtcggat atgctcggac | 1740 |

```
gaacatggac cacgaagaat atctgagacg ggtgcgctcg tacatcaaga ccccaccaa    1800 ggaaatcgaa gaacagc                                                  1817

<210> SEQ ID NO 70
<211> LENGTH: 1825
<212> TYPE: DNA
<213> ORGANISM: artificial sequence
<220> FEATURE:
<223> OTHER INFORMATION: amplicon 3'gsdA A. terreus

<400> SEQUENCE: 70
tcaacctcac caagcacctc gaggacgtcg agaagggcca taaggaacag aacagagtct     60
tctacatggc gctgcctcct agcgtcttca ttaccgtgtc ggatcaattg aagagaaact    120
gctaccccaa gaacggcatt gcccgtatta ttgtgagtcg ccaacacaaa gctttgttt    180 ctaccgaggc atatgcttac gcgtgttttc tttgtgtcta caggtcgaga agcccttcgg    240
caaggatctc cagagttctc gtgacctcca gaaggcccct gagcccaact ggaaggagga    300
ggagatcttc cgtattgacc actacctggg taaggagatg gtcaagaaca ttctcatcat    360
gcgcttcgga aacgagttct tcaacgctac ctggaaccgt caccacattg ataacgtgca    420
ggtatgagtt gaatgttttc aggacgaccg gtgcagatgc taagctcttg tcgcagatca    480
cattcaagga gccgttcggc acggagggcc gtggaggtta ctttgatgag ttcggcatca    540
ttcgtgatgt catgcagaac cgtatgtcca acaaaaaaat gaccttgacg gctaatgatg    600
gcaagtgcta atgtccttat ctagaccttc tgcaggtgtt gacgcttctt gccatggagc    660
gtcccatctc tttctctgct gaagacattc gtgatgagaa ggtattttg ccgatccctt    720 atcccaccgg cggcaactaa cgtaagtgac aggtgcgtgt tctgcgcgcg atggacccca    780
ttgagccaaa gaacgtcatc atcggccagt acggaaagtc gctcgacggt agcaagcccg    840
cctacaagga ggatgatact gtccctcaag actcgcgctg cccgactttc tgcgccatgg    900
ttgcgtacat caagaacgag agatgggatg gcgttcccctt catcatgaag gccggtaaag    960
gtatgtatcc tgttctctat ggcagcacgc cctggacttg gtgtactcac atcttcgaca   1020
gccctgaacg agcagaagac cgagatccgt atccagttcc gtgacgtcac ttccggcatc   1080
ttcaaggaca tcccccgcaa cgaacttgtt attcgcgtcc agcccaacga gtcggtgtac   1140
attaagatga actccaagct gccgggtctc tccatgcaga cggtcgttac cgagcttgac   1200
cttacctacc gccgccgttt ctccgacctc aagatcccgg aggcttacga gtctctgatt   1260
ctggatgctc tgaagggtga ccactcgaac tttgtccgtg acgatgaact tgactcgagc   1320
tggaagatct tcacccctct gctgcactac ctggacgaca caaggagat catcccccatg   1380 gaatacccct acggtaagcg gcgaatgcgc catctgcgaa acaaaatatt tcttttgagt   1440
tccagtactg acaatgttat caggctctcg cggacctgct gtgctcgacg acttcaccgc   1500
atcgttcggg tacaagttca gtgatgctgc tggctaccag tggcccctga cttcggcccc   1560
caacagactg taaatgaaaa atattatgat cgtttaagca atgaaaaggg aaagaaggaa   1620
aatgggttaa tgtgagcact accgggtttc atagcatgat cggatggtcc tcgaggttgg   1680
gatggcacga tatttggaga cgggttttcc agatcggcca tggtggacca gacgctcccc   1740
tgggtcccta gaaacgaatg aagtgactgt tacgaatcaa acacgatgat attgattccc   1800
tcttgcagtt gcgacgggct gtttg                                         1825

<210> SEQ ID NO 71
```

```
<211> LENGTH: 1731
<212> TYPE: DNA
<213> ORGANISM: artificial sequence
<220> FEATURE:
<223> OTHER INFORMATION: alpha-farnesene synthase

<400> SEQUENCE: 71
atggaattca gagtccactt acaagccgat aacgaacaaa agatattcca aaaccaaatg      60
aaaccagaac cagaagcctc ctacttaatt aatcaaagaa gatcagctaa ctacaagcca     120
aacatctgga agaacgattt cttggatcaa tcattgatct ctaagtacga tggtgacgaa     180
tacagaaagt tatcagaaaa gttgatcgaa gaagttaaga tctatatttc tgctgaaact     240
atggatttgg ttgcaaagtt ggaattgatc gattctgtta gaaagttggg tttagctaat     300
ttgttcgaaa aggaaattaa agaagcattg gattcaatcg ctgcaatcga atctgataat     360
ttgggtacta gagatgattt gtacggtaca gctttgcatt tcaagatttt gagacaacat     420
ggttacaaag tttcacaaga tatcttcggt agattcatgg atgaaagggg tactttggaa     480
aaccatcatt tcgctcattt gaagggcatg ttggaattgt tcgaagcatc taatttgggt     540
ttcgaaggtg aagatatctt ggatgaagct aaagcatcat tgacattagc tttgagagat     600
tctggtcata tctgttaccc agattcaaat ttgtctagag atgttgttca ttcattagaa     660
ttgccatctc atagaagagt tcaatggttc gatgttaagt ggcaaattaa tgcttacgaa     720
aaggatatct gtagagttaa cgctactttg ttggaattgg caaagttgaa cttcaatgtt     780
gttcaagcac aattgcaaaa gaatttgaga gaagcttcta gatggtgggc aaatttgggt     840
atcgctgata atttgaagtt cgctagagat agattggttg aatgttttgc ttgtgcagtt     900
ggtgttgcat tcgaaccaga acattcttct tttagaatct gtttgacaaa agttattaat     960
ttggttttga ttattgatga tgtttatgat atctatggtt cagaagaaga attgaagcat    1020
ttcactaatg ctgttgatag atgggattct agagaaacag aacaattgcc agaatgtatg    1080
aagatgtgtt tccaagtttt gtacaacact acatgtgaaa tcgcaagaga aatcgaagaa    1140
gaaaatggtt ggaaccaagt tttgccacaa ttgactaagg tttgggcaga tttttgtaaa    1200
gctttgttgg ttgaagcaga atggtacaat aagtcacata tcccaacatt ggaagaatac    1260
ttgagaaacg gttgtatctc ttcatctgtt tctgttttgt tggttcattc tttcttttct    1320
atcactcatg aaggtacaaa ggaaatggct gatttcttgc ataagaacga agatttgttg    1380
tacaacatct cattaattgt tagattgaat aatgatttgg gtacttcagc tgcagaacaa    1440
gaaagaggtg actctccatc atctatcgtt tgttacatga gagaagttaa tgcttctgaa    1500
gaaacagcaa gaaagaatat caagggtatg atcgataacg cttggaagaa agttaacggt    1560
aaatgtttca ctacaaacca agttccattt ttatcatctt ttatgaataa tgcaacaaat    1620
atggctagag ttgcacattc tttgtacaaa gatggtgacg gttttggtga ccaagaaaaa    1680
ggtccaagaa cccacatatt atcattatta ttccaaccat tagtaaactg a              1731
```